US008530153B1

United States Patent
Kung

(10) Patent No.: US 8,530,153 B1
(45) Date of Patent: Sep. 10, 2013

(54) LENTIVIRAL TRANSDUCED DENDRITIC CELLS FOR RNAI

(75) Inventor: Sam Kam Pun Kung, Manitoba (CA)

(73) Assignee: Technologiy Transfer Office, University of Manitoba, Manitoba (CA)

( * ) Notice: Subject to any disclaimer, the term of this patent is extended or adjusted under 35 U.S.C. 154(b) by 0 days.

(21) Appl. No.: 13/045,297

(22) Filed: Mar. 10, 2011

Related U.S. Application Data

(60) Provisional application No. 61/312,457, filed on Mar. 10, 2010.

(51) Int. Cl.
*C12Q 1/68* (2006.01)

(52) U.S. Cl.
USPC .............................. 435/6; 435/325; 435/375

(58) Field of Classification Search
None
See application file for complete search history.

(56) References Cited

U.S. PATENT DOCUMENTS

2006/0182726 A1 * 8/2006 Thomas et al. ............ 424/93.21

OTHER PUBLICATIONS

Li et al. (Journal of Immunology 2007, vol. 178:5480-5487).*
An et al. (Human Gene Therapy 2003, vol. 14:1207-1212).*
Karimi et al. (Cellular Immunology 2009, vol. 259L 74-81).*
Hill et al. (Journal of Immunology 2003, vol. 171:691-696).*
Wang, H., et al., "Emerging applications of lentiviral vectors in dendritic cell-based immunotherapy", Immunotherapy, 2(5), (Sep. 2010), 685-95.
Zhang, L., et al., "Functional analysis of the quantitative expression of a costimulatory molecule on dendritic cells using lentiviral vector-mediated RNA interference.", J Immunol Methods., 344(2), (May 31, 2009), 87-97.

* cited by examiner

*Primary Examiner* — Kimberly Chong
(74) *Attorney, Agent, or Firm* — Schwegman Lundberg & Woessner, P.A.

(57) ABSTRACT

The invention provides methods to prepare and use lentivirus transduced mammalian dendritic cells with altered levels of T cell co-stimulatory molecules.

11 Claims, 13 Drawing Sheets

CD40 type I transcript NM_011611
ATGgtgtctttgcctcggctgtgcgcgctatggggctgcttgttgacagcggtccatctagggcagtgtgttacgtgcagtgacaaac
agtacctccacgatggccagtgctgtgatttgtgccagccaggaagccgactgacaagccactgcacagctcttgagaagacccaatg
ccacccatgtgactcaggcgaattctcagcccagtggaacagggagattcgctgtcaccagcacagacactgtgaacccaatcaagg
gcttcggggttaagaaggagggcaccgcagaatcagacactgtctgtacctgtaaggaaggacaacactgcaccagcaaggattgcga
ggcatgtgctcagcacacgccctgtatccctggctttggagttatggagatggccactgagaccactgataccgtctgtcatccctgccc
agtcggcttcttctccaatcagtcatcacttttcgaaaagtgttatccctggacaagctgtgaggataagaacttggaggtcctacagaaa
ggaacgagtcagactaatgtcatctgtggtttaaagtcccggatgcgagccctgctggtcattcctgtcgtgatgggcatcctcatcacca
ttttcggggtgtttctctatatcaaaaaggtggtcaagaaaccaaaggataatgagatcttaccccctgcggctcgacggcaagatcccc
aggagatggaagattatcccggtcataacaccgctgctccagtgcaggagacgctgcacgggtgtcagcctgtcacacaggaggatg
gtaaagagagtcgcatctcagtgcaggagcggcaggtgacagacagcatagccttgaggcccctggtctgaagcagggactttgga
gtgacttgtggcttcagcaggagccctgtgatttggctcttctgatctcgccctgcgatggtgtctttgcctcggctgtgcgcgctatggggg
ctgcttgttgacagcggtccatctagggcagtgtgttacgtgcagtgacaaacagtacctccacgatggccagtgctgtgatttgtgcca
gccaggaagccgactgacaagccactgcacagctcttgagaagacccaatgccacccatgtgactcaggcgaattctcagcccagtg
gaacagggagattcgctgtcaccagcacagacactgtgaacccaatcaaggggcttcggggttaagaaggagggcaccgcagaatcag
acactgtctgtacctgtaaggaaggacaacactgcaccagcaaggattgcgaggcatgtgctcagcacacgccctgtatccctggcttt
ggagttatggagatggccactgagaccactgataccgtctgtcatccctgcccagtcggcttcttctccaatcagtcatcacttttcgaaaa
gtgttatccctggacaagctgtgaggataagaacttggaggtcctacagaaaggaacgagtcagactaatgtcatctgtggtttaaagt
cccggatgcgagccctgctggtcattcctgtcgtgatgggcatcctcatcaccattttcggggtgtttctctatatcaaaaaggtggtcaa
gaaaccaaaggataatgagatcttacccctgcggctcgacggcaagatccccaggagatggaagattatcccggtcataacacc
gctgctccagtgcaggagacgctgcacgggtgtcagcctgtcacacaggaggatggtaaagagagtcgcatctcagtgcaggagcg
gcaggtgacagacagcatagccttgaggcccctggtcTGAaccctggaactgctttggaggcgatggctcggctcgggagcagg
ggcctggctctgaggactgcttgctgacctttgaagtttgagatgagccaagacagagcccagtgcagctaactctcatgcctgccccc
tatcatttctcaacttgcttttaaggatggagggagagctcgggcatcggggggtccacagtgatacctaccaagtgcagcagtgcagg
acccagagtcgtcttgctgcggcgttcactgtaaggagtcatggacacaggagtccgtggcccacagcttgtgctgctagagggcacc
tggttgcccatcag**cagggtactggctaaataaatctgtaattatttatacaatgacatctcagaaactctagcaggtggggcagaaaa
caggtagtagaatgatgggtagagaaatagcttttaaaacacattccaaggcaggtaagatggcttttgtgagtaaaggagcttgctgcc
caaacccggttacctgattttgatccctgggacttcatggtaaaagggagagaaccaaatccagagggttgtcatttgacctccatgtgtg
ctctgtggtaatgtaccccgtgtgtgcacatgtgcacatatcctaaaatggatgtggtggtgtattgtagaaattatt**taatcccgccctg
gggtttctacctgtgtgttaccatttagttcttgaataaaagacacactcaacctttatatttacaataa

*FIG. 1*

LENTIVIRAL TRANSDUCED DENDRITIC CELLS FOR RNAI

CROSS-REFERENCE TO RELATED APPLICATIONS

This application claims the benefit of the filing date of U.S. application Ser. No. 61/312,457, filed on Mar. 10, 2010, the disclosure of which is incorporated by reference herein in its entirety.

BACKGROUND

Dendritic cells (DC) are professional antigen-presenting cells of the immune system. They have the ability to take up, process and present antigens (Ag) to resting lymphocytes in draining lymph nodes. The importance of DC in initiation of T cell immunity and tolerance is firmly established (Steinman et al., 2003). Functionally mature DC are highly efficient at priming adaptive immune responses against viruses, pathogens and endogenous tumors (Banchereau and Steinman, 1998); whereas steady state "immature" DC are capable of uptaking and presenting self-Ag to tolerize autoreactive T cells (Wilson et al., 2003; Bonifaz et al., 2002; Hawiger et al., 2001; Scheinecker et al., 2002; Steinman et al., 2000). Phenotypic analysis of surface expression of co-stimulatory molecules has been routinely used in defining mature and "immature" DC. The ability to use DC in the induction of antigen (Ag)-specific tolerance, Ag-specific immunity or specific differentiation of T helper subsets holds great promises in DC-based immunotherapy of various diseases such as cancer, viral infections, allergy, as well as autoimmunity. The increasing number of co-stimulatory molecules identified to date, however, highlights the complex regulation of co-stimulatory signals.

RNA interference (RNAi) is an innate cellular process that involves multiple RNA-protein interactions (Fire, 1999; Hannon, 2002). Its gene silencing activity is activated when a double-stranded RNA (dsRNA) molecule of greater than 19 duplex nucleotides enters the cells, causing degradation of both the dsRNA and single stranded RNA (endogenous mRNA) of identical sequences (Fire, 1999; Hannon, 2002). Transient transfection of short synthetic dsRNA in DC demonstrated the feasibility of applying this technique in studying DC functions (Li et al., 2004; Gu et al., 2006; Hill et al., 2003; Laderach et al., 2003; Liu et al., 2004; Orabona et al., 2005; Li et al., 2007). A single lentiviral vector system has been established to stably express short hairpin RNA (shRNA) to induce RNA interference (RNAi) in cell lines and primary T cells (An et al., 2003; Qin et al., 2003).

SUMMARY OF THE INVENTION

The increasing number of co-stimulatory molecules identified on dendritic cells (DC) to date highlights the complex regulation of co-stimulatory signals in T cell activation. As described herein, a single lentiviral vector system to stably express short hairpin RNA (shRNA) to induce RNA interference (RNAi) was employed to regulate different levels of surface expression of a co-stimulatory molecule stably and reproducibly in dendritic cells. First, as described herein, it was demonstrated that lentiviral vectors induced RNA interference in DC without functional impairments. Then CD40 was employed as a target co-stimulatory molecule to demonstrate the feasibility of using lentiviral vectors in delivering different shRNA target sequences to genetically modify DC so as to express different levels of CD40. Functional data demonstrated that quantitative expression of CD40 on LPS-stimulated DC had different functional outcomes on Ag-specific T cell responses in vitro and in vivo. Collectively, this system allows the examination of functional significance(s) of the quantitative and/or qualitative expression of a single or multiple co-stimulatory molecule(s) on DC, provides a platform to genetically modify primary DC to express defined, quantitative expression levels of a protein of interest, and allows the genetic engineering of DC to define their functional properties (such as tolerance, Th1 inducing or Th2 inducing) in DC-based therapies.

The invention provides methods of making lentivirus transduced DC, e.g., primary DC, mature DC or immature DC, useful in the immunotherapy of a large number of immune and inflammatory disorders (e.g., AIDS, cancers, allergy, autoimmune diseases, and graft rejections in transplantation), such in suppression of immune responses in autoimmune disease, allergy or transplantation, as well as in anti-cancer and anti-viral immunotherapies.

In one embodiment, the invention provides a recombinant lentivirus having a genome with sequences, e.g., sequences useful to generate short hairpin RNA (shRNA), selected to alter the expression of a co-stimulatory molecule on DC. Co-stimulatory molecules for DC include but are not limited to ICAM-1, ICOS-L, B7.1 (CD80), B7.2 (CD86), B7RP1, 4-1BB-L, PD-L, OX40L or CD40, or other molecules that bind to molecules on T cells, molecules such as LFA-1, CD28, ICOS, CTLA-4, PD-1, 4-1BB (CD137), OX40 (CD134), or CD40L. In one embodiment, the lentivirus vector comprises a plurality of different sequences for one co-stimulatory molecule, e.g., each sequence with sequence similarity to different regions of the gene of the co-stimulatory molecule. In one embodiment, the lentivirus vector comprises a plurality of different sequences for different co-stimulatory molecules, e.g., each sequence has sequence similarity to a different co-stimulatory molecule gene. In one embodiment, the stable dendritic cells, when presenting antigen, alter the induction of Th1 cells. In one embodiment, the stable dendritic cells, when presenting antigen, alter the induction of Th2 cells.

In one embodiment, a recombinant, e.g. helper-free, lentivirus expresses sequences in DC that yield shRNA sequences specific for CD40 nucleic acid sequences, e.g., human CD40 sequences, which is turn induce RNAi in those cells, thereby altering the expression of CD40. In one embodiment, the shRNA sequences correspond to sequences in the coding region of the co-stimulatory molecule gene, e.g., CD40 gene. In another embodiment, the shRNA sequences correspond to sequences in the 3' non-coding region of the co-stimulatory molecule gene, e.g., CD40 gene.

In one embodiment, the expression of the shRNA sequences decreases surface expression of the co-stimulatory molecule. In one embodiment, the decreased expression of the co-stimulatory molecule results in DC that, when exposed to an antigen and antigen-specific T cells, suppresses the proliferation of those T cells. In one embodiment, the antigen is an auto-antigen. In one embodiment, the antigen is an allo-antigen. In one embodiment, the antigen is an allo-antigen specific for a tissue or organ to be transplanted. In one embodiment, the antigen is an allergy specific antigen. In one embodiment, the antigen is an auto-antigen associated with an autoimmune disease. In one embodiment, the antigen is an exogenous antigen. As used herein, an "exogenous" antigen is one not normally encoded by the genome of and expressed in a mammal.

In one embodiment, the decreased expression of the co-stimulatory molecule results in DC that, when exposed to an antigen and antigen-specific T cells, tolerizes those T cells. In one embodiment, the decreased expression of the co-stimulatory molecule results in DC that, when exposed to an antigen and antigen-specific T cells, results in apoptosis of those T cells. In one embodiment, the administration of the dendritic cells of the invention to a mammal results in T cell tolerization, the down regulation of priming or activity of T cells, the inhibition of at least one symptom of an indication or disease, or any combination thereof.

In one embodiment, the expression of the sequences in the lentivirus vector in DC increases surface expression of a co-stimulatory molecule. In one embodiment, the increased expression of the co-stimulatory molecule results in DC that, when exposed to an antigen and antigen-specific T cells, enhances the proliferation of those T cells. In one embodiment, the antigen is a tumor specific antigen. In one embodiment, the antigen is a pathogen specific antigen, e.g., a viral, bacterium or fungal specific antigen The invention provides a method of making stably transduced mammalian dendritic cells. The method includes providing a population of mammalian dendritic cells and stably transducing the cells with a recombinant helper-free lentivirus comprising a genome having a transcription cassette comprising nucleic acid sequences for a T cell co-stimulatory molecule, the expression of which is capable of inducing RNAi in the dendritic cells and altering the immune properties of the dendritic cells. In one embodiment, the co-stimulatory molecule comprises CD40, ICOS-L, ICAM-1, B7.1 (CD80), B7.2 (CD86), B7RP1, 4-1BB-L, PD-L, or OX40L. In one embodiment, the cells are human cells. In one embodiment, the nucleic acid sequences encode short hairpin RNA, e.g., of lengths of about 15 to about 1000 nucleotides in length, or any integer between 15 and 1000, e.g., 20, 30, 40, 50, 60, 70 or 100 nucleotides. In one embodiment, the stably transduced dendritic cells have decreased levels of one or more T cell co-stimulatory molecules relative to corresponding cells that are not transduced by the recombinant helper-free lentivirus, e.g., when cells are contacted with an agent that stimulates expression of the co-stimulatory molecules.

Further provided is a population of isolated stably lentivirus transduced mammalian dendritic cells comprising a recombinant lentivirus comprising a transcription cassette comprising nucleic acid sequences for a T cell co-stimulatory molecule, the expression of which is capable of inducing RNAi in the dendritic cells and altering the immune properties of the dendritic cells. In one embodiment, the co-stimulatory molecule comprises CD40, ICOS-L, ICAM-1, B7.1 (CD80), B7.2 (CD86), B7RP1, 4-1BB-L, PD-L, or OX40L. In one embodiment, the cells are human cells. In one embodiment, the nucleic acid sequences encode short hairpin RNA, e.g., of lengths of about 15 to about 1000 nucleotides in length, or any integer between 15 and 1000, e.g., 20, 30, 40, 50, 60, 70 or 100 nucleotides. In one embodiment, the stably transduced dendritic cells have decreased levels of the T cell co-stimulatory molecule relative to corresponding cells that are not transduced by the recombinant helper-free lentivirus.

BRIEF DESCRIPTION OF FIGURES

FIG. 1. RNAi sequences against mouse CD40 gene (NM_011611) (SEQ ID NO:11). pLKOCD40 clones (66243, nucleotide 2136-2156, GCAGGGTACTGGCTAAATAAA; SEQ ID NO:1), (66244, nucleotide 1606-1626, CCAAAGGATAATGAGATGTTA; SEQ ID NO:2) were obtained from Open Biosystems (Huntsville, Ala.); FG12-siCD40#1, nucleotide 2502-2522, TACCATTTAGTTCTTGAATAA; SEQ ID NO:3; FG12-siCD40#2, nucleotide 1590-1610, AAAGGTG-GTCAAGAAACCAAA; SEQ ID NO:4; FG12-siCD40#3, nucleotide 2449-2469 GTGGTGTATTGTAGAAATTAT; SEQ ID NO:5; FG12-siCD40#4, nucleotide 1431-1451, CTGGACAAGCTGTGAGGATAA; SEQ ID NO:6.

DETAILED DESCRIPTION OF THE INVENTION

Figure 2A:
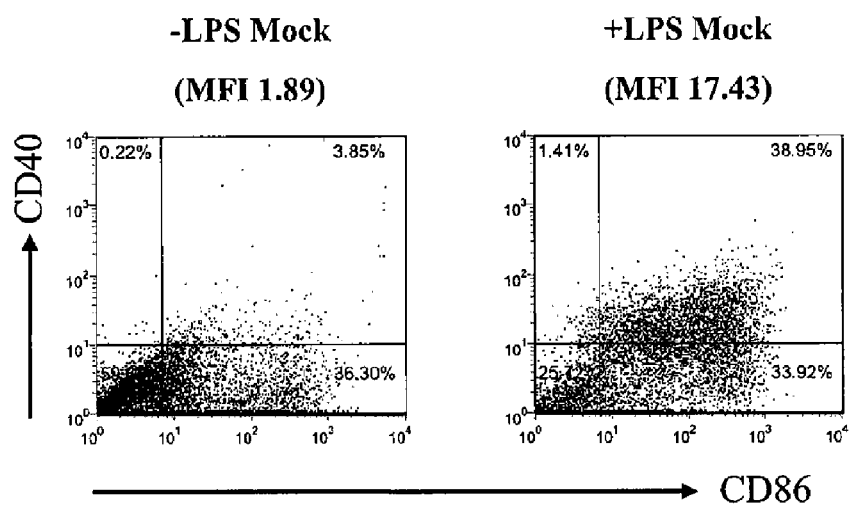
FIG. 2. Efficient lentiviral vectors transduction in bone marrow-derived dendritic cell. A) Phenotype of bone marrow-derived dendritic cells before and after LPS stimulation. Mean Fluorescence Intensity (MFI) of CD40 was indicated. B) Lentiviral vectors were highly efficient in transducing DC. Over 85% of CD11c$^+$ was transduced and expressed EGFP reporter gene. Percentages of EGFP-expressing cells were maintained upon LPS stimulation. C) The shRNA-expressing lentiviral vectors that down-regulate CD40 expression at different levels specifically. The CD40-silencing constructs, FG12H1Si#4 and 66243, were capable of mediating 2 to 4-fold down-regulation of the Mean Fluorescence Intensity of surface CD40 expression respectively when compared to the mock and irrelevant FG12H1SiLuc control. The MFI of CD40 was indicated for each DC group. The gene silencing of CD40 was specific because surface expression of C086 was not affected in these transduced DC.

In contrast to transient transfection studies, the lentiviral vector system supports stable and long-term expression of shRNA in the modified cells that might prove useful in development of stable, genetically defined DC to study the role of co-stimulatory molecules in functional definition of DC in vivo. As the sequence encoded in the dsRNA contributes to the potency of the dsRNA in degradation of target mRNA (Reynolds et al., 2004), the choice of shRNA target sequences in the lentiviral vector system may allow regulation of different levels of surface expression of a co-stimulatory molecule stably and reproducibly. For instance, inhibiting expression of certain co-stimulatory molecules in dendritic cells when those cells are presenting antigen to T cells, may suppress an immune response and/or tolerize those T cells, which may be useful in diseases such as autoimmune diseases or aberrant immune responses to exogenous antigens, e.g., those causing allergic disorders.

The invention thus provides a population of isolated stably lentivirus transduced mammalian dendritic cells comprising a recombinant lentivirus comprising a transcription cassette comprising nucleic acid sequences for a T cell co-stimulatory molecule, the expression of which is capable of inducing RNAi in the dendritic cells and altering the immune properties of the dendritic cells. In one embodiment, the co-stimulatory molecule comprises CD40, ICOS-L, ICAM-1, B7.1 (CD80), B7.2 (CD86), B7RP1, 4-1BB-L, PD-L, or OX40L. In one embodiment, the cells are human cells. In one embodiment, the nucleic acid sequences encode short hairpin RNA, e.g., of lengths of about 15 to about 1000 nucleotides in length, or any integer between 15 and 1000, e.g., 20, 30, 40, 50, 60, 70 or 100 nucleotides. In one embodiment, the stably transduced dendritic cells have decreased levels of the T cell co-stimulatory molecule relative to corresponding cells that are not transduced by the recombinant helper-free lentivirus.

The invention also provides a method to induce suppression of antigen specific T cells in a mammal. The method includes administering to a mammal having or suspected of having antigen specific T cells, an effective amount of a population of isolated stably lentivirus transduced mammalian dendritic cells comprising a recombinant lentivirus comprising a transcription cassette comprising nucleic acid sequences for a T cell co-stimulatory molecule, the expression of which is capable of inducing RNAi in the dendritic cells, which population is exposed to the antigen. In one embodiment, the antigen is an auto-antigen. In one embodiment, the antigen is an exogenous antigen.

The invention provides a method to induce allo-specific T cell proliferation or suppression. The method includes contacting dendritic cells with an effective amount of a recombinant DNA having a nucleic acid sequence for a co-stimulatory molecule. In one embodiment, the expression of the recombinant DNA in dendritic cells induces RNA interference. In one embodiment, the expression of the recombinant DNA in dendritic cells increases expression or activity of the co-stimulatory molecule.

Also provided is a method to prime or inhibit a specific T cell response, comprising contacting dendritic cells with an effective amount of a recombinant DNA having a nucleic acid sequence for a co-stimulatory molecule. In one embodiment, the expression of the recombinant DNA in dendritic cells induces RNA interference. In one embodiment, the expression of the recombinant DNA in dendritic cells increases expression or activity of the co-stimulatory molecule.

Further provided is a method to increase or decrease CD40 expression in dendritic cells, comprising contacting dendritic cells with an effective amount of a recombinant DNA having a nucleic acid sequence for CD40. In one embodiment, the expression of the recombinant DNA in dendritic cells induces RNA interference. In one embodiment, the expression of the recombinant DNA in dendritic cells increases expression or activity of CD40. In one embodiment, the expression of the recombinant DNA in dendritic cells decreases expression or activity of CD40.

A. Exemplary Autoimmune Diseases

Autoimmune diseases are characterized by an abnormal immune response involving either cells or antibodies, that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uveoretinitis (see Table 1). Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia (see Table 1). The antigen(s) associated with systemic lupus erythematosus is small nuclear ribonucleic acid proteins (Snurps), Graves' disease is the thyrotropin receptor, thyroglobulin and other components of thyroid epithelial cells (Akamizu et al., 1996;

Kellerman et al., 1995; Raju et al., 1997; and Texier et al., 1992), pemphigus is cadherin-like pemphigus antigens such as desmoglein 3 and other adhesion molecules (Memar et al., 1996: Stanley, 1995; Plott et al., 1994; and Hashimoto, 1993), and thrombic thrombocytopenic purpura is antigens of platelets.

Other autoimmune diseases and their specific autoantigens and/or target tissues are disclosed in Schwartz, R. S. et al. in *Fundamental Immunology*, Third Edition, Paul, W. E., Ed., Raven

TABLE 1

| Disease Model | Specific Autoantigen |
| --- | --- |
| Multiple Sclerosis | MBP |
| Rheumatoid Arthritis | Collagen |
| Autoimmune Thyroiditis | Thyroglobulin |
| Myasthenia Gravis | Acetylcholine receptor |
| Autoimmune uvoretinitis | S-antigen |
| Systemic Lupus Erythematosus | DNA |
| Diabetes | islet cell extract |
| Chronic Active Hepatitis | Liver extract |
| Adrenalitis | Adrenal gland extract |
| Polymyositis | Muscle extract |
| Autoimmune hemolytic anemia | Hematopoietic cells |
| Rheumatic carditis | Heart extract |
| Scleroderma | Skin cell extract |

An autoimmune disease is a malfunction of the immune system of mammals, including humans. In a mammal afflicted with such a disease, the immune system treats autologous tissues (self or endogenous antigens) and substances as if they were foreign and dangerous, and evokes the immune defense that is usually reserved for use against exogenous and dangerous substances (e.g., foreign tissues or invading organisms), including sensitization of T cells and synthesis of high affinity antibodies. Table 2 provides exemplary recombinant or purified autoantigens recognized by autoantibodies associated with human autoimmune disorders.

TABLE 2

| Autoantigen | Autoimmune disease |
| --- | --- |
| A. Cell or organ-specific autoimmunity | |
| Acetylcholine receptor | Myasthenia gravis |
| Actin | Chronic active hepatitis, primary biliary cirrhosis |
| Adenine nucleotide translocator (ANT) | Dilated cardiomyopathy, myocarditis |
| β-Adrenoreceptor | Dilated cardiomyopathy |
| Aromatic L-amino acid decarboxylase | Autoimmune polyendocrine syndrome type 1 (APS-1) |
| Asialoglycoprotein receptor | Autoimmune hepatitis |
| Bactericidal/permeability-increasing protein (Bpi) | Cystic fibrosis vasculitides |
| Calcium-sensing receptor | Acquired hypoparathyroidism |
| Cholesterol side-chain cleavage enzyme (CYPlla) | APS-1 |
| Collagen type IV α$_3$-chain | Goodpasture syndrome |
| Cytochrome P450 2D6 (CYP2D6) | Autoimmune hepatitis |
| Desmin | Crohn disease, coronary artery disease |
| Desmoglein 1 | Pemphigus foliaceus |
| Desmoglein 3 | Pemphigus vulgaris |
| F-actin | Autoimmune hepatitis |
| GM gangliosides | Guillain-Barre syndrome |
| Glutamate decarboxylase (GAD65) | Type 1 diabetes, stiff man syndrome |
| Glutamate receptor (GLUR) | Rasmussen encephalitis |
| H/K ATPase | Autoimmune gastritis |
| 17-a-Hydroxylase (CYP17) | APS-1 |
| 21-Hydroxylase (CYP21) | Addison Disease |

TABLE 2-continued

| Autoantigen | Autoimmune disease |
| --- | --- |
| IA-2 (ICA512) | Type 1 diabetes |
| Insulin | Type 1 diabetes, insulin hypoglycemic syndrome (Hirata disease) |
| Insulin receptor | Type B insulin resistance, acanthosis, systemic lupus erythematosus (SLE) |
| Intrinsic factor type 1 | Pernicious anemia |
| Leukocyte function-associated antigen (LFA-1) | Treatment-resistant Lyme arthritis |
| Myelin-associated glycoprotein (MAG) | Polyneuropathy |
| Myelin basic protein | Multiple sclerosis, demyelinating diseases |
| Myelin oligodendrocyte glycoprotein (MOG) | Multiple sclerosis |
| Myosin | Rheumatic fever |
| p-80-Coilin | Atopic dermatitis |
| Pyruvate dehydrogenase complex-E2 (PDC-E2) | Primary biliary cirrhosis |
| Sodium iodide symporter (NIS) | Graves disease, autoimmune hypothyroidism |
| SOX-10 | Vitiligo |
| Thyroid and eye muscle shared protein | Thyroid associated ophthalmopathy |
| Thyroglobulin | Autoimmune thyroiditis |
| Thyroid peroxidases | Autoimmune Hashimoto thyroiditis |
| Thyrotropin receptor | Graves disease |
| Tissue transglutaminase | Coeliac disease |
| Transcription coactivator p75 | Atopic dermatitis |
| Tryptophan hydroxylase | APS-1 |
| Tyrosinase | Vitiligo, metastatic melanoma |
| Tyrosine hydroxylase | APS-1 |
| B. Systemic autoimmunity | |
| ACTH | ACTH deficiency |
| Aminoacyl-tRNA histidyl synthetase | Myositis, dermatomyositis |
| Aminoacyl-tRNA synthetase (several) | Polymyositis, dermatomyositis |
| Cardiolipin | SLE |
| Carbonic anhydrase II | SLE, Sjogren syndrome, systemic sclerosis |
| Autoantigen | Autoimmune disease |
| Collagen (multiple types) | Rheumatoid arthritis (RA), SLE, progressive systemic sclerosis |
| Centromere-associated proteins | Systemic sclerosis |
| DNA-dependent nucleosome-stimulated ATPase | Dermatomyositis |
| Fibrillarin | Scleroderma |
| Fibronectin | SLE, RA, morphea |
| Glucose-6-phosphate isomerase | RA |
| β2-Glycoprotein 1 (β2-GPI) | Primary antiphospholipid syndrome |
| Golgin (95, 97, 160, 180) | Sjogren syndrome, SLE, RA |
| Heat shock protein | Various immune-related disorders |
| Hemidesmosomal protein 180 | Bullous pemphigoid, herpes gestationis, cicatricial pemphigoid |
| Histone H2A-H2B-DNA | SLE |
| IgE receptor | Chronic idiopathic urticaria |
| Keratin | RA |
| Ku-DNA-protein kinase | SLE |
| Ku-nucleoprotein | Connective tissue syndrome |
| La phosphoprotein (La 55-B) | Sjogren syndrome |
| Myeloperoxidase | Necrotizing and crescentic glomerulonephritis (NCGN), systemic vasculitis |
| Proteinase 3 (PR3) | Wegener granulomatosis, Churg-Strauss syndrome |
| RNA polymerase I-III (RNP) | Systemic sclerosis, SLE |
| Signal recognition protein (SRP54) | Polymyositis |
| Topoisomerase-I (Scl-70) | Scleroderma, Raynaud syndrome |
| Tubulin | Chronic liver disease, visceral leishmaniasis |
| Autoantigen | Autoimmune disease |
| Vimentin | Systemic autoimmune disease |
| C. Plasma protein and cytokine autoimmunity | |
| C1 inhibitor | Autoimmune C1 deficiency |
| C1q | SLE, membrane proliferative |
| Cytokines (IL-1α, IL-β, IL-6, IL-10, LIF) | RA, Systemic sclerosis, normal subjects |

TABLE 2-continued

| Autoantigen | Autoimmune disease |
| --- | --- |
| Factor II, factor V, factor VII, factor VIII, factor IX, factor X, factor XI, factor XII, thrombin, vWF | Prolonged coagulation time |
| Glycoprotein IIb/IIIg and Ib/IX | Autoimmune thrombocytopenia purpura |
| IgA | Immunodeficiency |
| Oxidized LDL (OxLDL) | Atherosclerosis |
| D. Cancer and paraneoplastic autoimmunity | |
| Amphiphysin | Neuronopathy, small lung cell cancer |
| Cyclin B1 | Hepatocellular carcinoma |
| DNA topoisomerase II | Liver cancer |
| Desmoplakin | Paraneoplastic pemphigus |
| Gephyrin | Paraneoplastic stiff man syndrome |
| Hu proteins | Paraneoplastic encephalomyelitis |
| Neuronal nicotinic acetylcholine receptor | Subacute autonomic neuropathy, cancer |
| p53 | Cancer, SLE |
| p62 (IGF-II mRNA-binding protein) | Hepatocellular carcinoma (China) |
| Recoverin | Cancer-Associated retinopathy |
| Ri protein | Paraneoplastic opsoclonus myoclonus ataxia |
| β IV spectrin | Lower motor neuron syndrome |
| Autoantigen | Autoimmune disease |
| Synaptotagmin | Lambert-Eaton myasthenic syndrome |
| Voltage-gated calcium channels | Lambert-Eaton myasthenic syndrome |
| Yo protein | Paraneoplastic cerebellar degeneration |

B. Exemplary Exogenous Antigens

Allergic diseases within the scope of the invention include allergic rhinitis, allergic asthma, atopic dermatitis, allergic gastroentheropathy, anaphylaxis, urticaria and angioedema. Allergens within the scope of the invention include, but are not limited to, protein antigens of *Alternaria altemata* (Alt a I), *Artemisia vulgaris* (Art v II), *Aspergillus fumigatus* (Asp f II), *Dermatophagoides far.* (Der f I), *Dermatophagoides pteron.* (Der p I, Der p III, Der p IV, Der p VI and Der p VIII), and domestic animals such as *Felis domesticus* (Fel d I), cows, pigs, poultry, mice, hamsters, rabbits, rats, guinea pigs, dogs and horses. Common fungal antigens include those of Basidiomycetes such as *Ustilago, Ganoderma, Alternaria, Cladosporium, Aspergillus, Sporobolomyces, Penicillium, Epicoccum, Fusarium, Phoma, Borrytis, Helminthosporium, Stemphylium* and *Cephalosporium; Phycomycetes* such as *Mucor* and *Rhizopus*; and Ascomycetes such as *Eurotium* and *Chaetomium.*

Pollinating plants which may have protein antigens associated with allergies include club mosses, ferns, conifers, flowering plants, grasses, sedges, palms, cattails, nettles, beeches, chenopods, sorrels, willows, poplars, maples, ashes, ragweeds (antigen E, antigen K and Ra3) and sages, or proteinaceous plant products such as those found in latex products.

Hymenoptera insects that may have protein antigens associated with allergies include the honeybee, yellow jacket, hornet, wasp and fire ant, although protein antigens of other insects are also within the scope of the invention.

Allergies associated with foods may be the result of protein antigens in crustaceans (e.g., shrimp, lobster and crab), mollusks (e.g., clams), fish, legumes (e.g., peanut, pea, beans, and licorice), seeds (e.g., sesame, cottonseed, caraway, mustard, flaxseed, and sunflower), nuts, berries, egg white, buckwheat and milk.

C. Pharmaceutical Compositions and Routes of Administration

The dendritic cells of the invention can be formulated as pharmaceutical compositions and administered to a mammalian host, such as a human patient in a variety of forms adapted to the chosen route of administration including parenteral, e.g., intravenous or intra-arterial, intradermal, subcutaneous, oral or nasal (e.g., inhalation), transdermal (topical), transmucosal, nasal, pulmonary, ocular, gastrointestinal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. Alternate routes of administration include intraperitoneal, intra-articular, intracardiac, intracisternal, intradermal, intralesional, intraocular, intrapleural, intrathecal, intrauterine, intraventricular, and the like.

The present dendritic cells may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. The percentage of the compositions and preparations may, of course, be varied and may conveniently be between about 2 to about 90% of the weight of a given unit dosage form. The amount of cells in such therapeutically useful compositions is such that an effective dosage level will be obtained.

The cells may also be administered intravenously or intraperitoneally by infusion or injection. Solutions of the particle or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms of the cells of the invention may be provided in an instant release, controlled release, sustained release, or target particle-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on the route of administration used, special devices may be required for application or administration of the particle, such as, for example, syringes and needles, inhalers, pumps, injection pens, applicators, or special flasks, or presented in the form of implants and pumps requiring incision. Pharmaceutical dosage forms are often composed of the cells, an excipient(s), and a container/closure system. One or multiple excipients, also referred to as inactive ingredients, can be added to the dendritic cells of the invention to improve or facilitate manufacturing, stability, administration, and safety of the particle, and can provide a means to achieve a desired release profile. Therefore, the type of excipient(s) to be added to the cells can depend on various factors, such as, for example, the physical and chemical properties of the particle, the route of administration, and the manufacturing procedure. Pharmaceutically acceptable excipients are available in the art, and include those listed in various pharmacopoeias. (See, e.g., USP, JP, EP, and BP, FDA web page (www-.fda.gov), Inactive Ingredient Guide 1996, and Handbook of Pharmaceutical Additives, ed. Ash; Synapse Information Resources, Inc. 2002.)

Pharmaceutical dosage forms of cells of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be used, possibly containing penetration enhancers. Such penetrants are generally known in the art. For oral administration, the dendritic cells can be formulated in liquid or semi-solid dosage forms and as instant or controlled/sustained release formulations. Suitable dosage forms for oral ingestion by a subject include tablets, pills, dragees, hard and soft shell capsules, liquids, gels, syrups, slurries, suspensions, emulsions and the like. The dendritic cells may also be formulated in rectal compositions, such as suppositories or retention enemas.

Pharmaceutical compositions suitable for injectable use include sterile aqueous solutions (where water soluble) or dispersions and sterile powders for the extemporaneous preparation of sterile injectable solutions or dispersion. Depending on the injection site, the vehicle may contain water, synthetic or vegetable oil, and/or organic co-solvents. In certain instances, such as with lyophilized product or a concentrate, the parenteral formulation would be reconstituted or diluted prior to administration. Depot formulations, providing controlled or sustained release of an invention dendritic cell, may include injectable suspensions of nano/micron or nano/micro or non-micronized crystals. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, poly(ol) (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the particle into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the particle can be incorporated with excipients and used in the form of tablets, troches, or capsules. Oral compositions can also be prepared using a fluid carrier for use as a mouthwash, wherein the particle in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; dissolution retardant; anti-adherants; cationic exchange resin; wetting agents; antioxidants; preservatives; a disintegrating agent such as alginic acid, Primogel, or corn starch; a lubricant such as magnesium stearate or Sterotes; a glidant such as colloidal silicon dioxide; a preservative; a colorant; a sweetening agent such as sugars such as dextrose, sucrose or saccharin; or a flavoring agent such as peppermint, methyl salicylate, or orange flavoring, each of these being synthetic and/or natural. Oral compositions can also include a self-assembling molecule expressed in a food plant that is then fed to the intended recipient.

For administration by inhalation, the dendritic cells are delivered in the form of an aerosol spray from pressured container or dispenser which contains a suitable propellant, e.g., a gas such as carbon dioxide, or a nebulizer. Systemic administration can also be by transmucosal means. For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. The active agents can also be prepared in the form of suppositories or retention enemas for rectal delivery.

In one embodiment, the compositions are prepared with carriers that protect rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

When a composition of the present invention is used for administration to an individual animal, it can further comprise salts, buffers, adjuvants, or other substances which are desirable for improving the efficacy of the composition. The composition may also contain variable but small quantities of endotoxin-free formaldehyde, and preservatives, which have been found safe and not contributing to undesirable effects in the organism to which the composition is administered.

Supplementary compounds can also be incorporated into the compositions. Carrier molecules may be genes, polypeptides, antibodies, liposomes or indeed any other agent provided that the carrier does not itself induce toxicity effects or cause the production of antibodies that are harmful to the individual receiving the pharmaceutical composition. Further examples of known carriers include polysaccharides, polylactic acids, polyglycolic acids and inactive virus particles. Carriers may also include pharmaceutically acceptable salts such as mineral acid salts (for example, hydrochlorides, hydrobromides, phosphates, sulphates) or the salts of organic acids (for example, acetates, propionates, malonates, benzoates). Pharmaceutically acceptable carriers may additionally contain liquids such as water, saline, glycerol, ethanol or auxiliary substances such as wetting or emulsifying agents, pH buffering substances and the like. Carriers may enable the pharmaceutical compositions to be formulated into tablets, pills, dragees, capsules, liquids, gels, syrups, slurries, suspensions to aid intake by the patient. Various formulations and particle delivery systems are available in the art, and a thorough discussion of pharmaceutically acceptable carriers are available in the art (see, e.g., USIP. Remington; The Science and Practice of Pharmacology (Lippincott Williams & Wilkins, 21st ed. 2005); and Ansel & Stoklosa, Pharmaceutical Calculations (Lippincott Williams & Wilkins, 11th ed., 2001).

Useful liquid carriers include water, alcohols or glycols or water-alcohol/glycol blends, in which the present dendritic cells can be dissolved or dispersed at effective levels, optionally with the aid of non-toxic surfactants. Adjuvants such as antimicrobial agents can be added to optimize the properties for a given use.

Useful dosages of the dendritic cells can be determined by comparing their in vitro activity, and in vivo activity in animal models. Methods for the extrapolation of effective dosages in mice, and other animals, to humans are known to the art; for example, see U.S. Pat. No. 4,938,949.

The concentration of the cells in a liquid composition may be from about 0.01-95 wt-% or more, e.g., from about 0.1-80 wt-%.

The amount of cells required for use in treatment will vary not only with the particular salt selected but also with the route of administration, the nature of the condition being treated and the age and condition of the patient and will be ultimately at the discretion of the attendant physician or clinician.

In general, however, a suitable dose may be in the range of from about $10^2$ to about $10^{10}$ cells, e.g., from about $10^4$ to about $10^8$ cells. The cells are conveniently administered in unit dosage form; for example, containing $10^2$ to $10^8$ cells, or conveniently $10^4$ to $10^6$ cells, or conveniently $10^6$ to $10^7$ cells per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention will be described by the following non-limiting examples.

Example I

The feasibility of using lentiviral vectors was established in delivering stable shRNA in the manipulation of DC functions in vitro and in vivo. A number of shRNA target sequences was used to demonstrate that lentiviral vectors delivered RNA interference in DC without functional impairments. For example, CD40 was used as a target co-stimulatory molecule to demonstrate the feasibility of generating DC that expresses different levels of CD40. Functional data further demonstrate that quantitative expression of CD40 on LPS-stimulated DC have different functional outcome on Ag-specific T cell responses in vitro.

Materials and Methods

Mice. C57BL/6 and BALB/c mice were purchased from Animal Care Services (The University of Manitoba). CD40-/- gene-targeted mice were purchased from Jackson Laboratory (Bar Harbor, Me., USA). The University of Manitoba's Review Board has approved all animal studies. DO11.10 TCR transgenic mice for I-$A^d$/OVA$_{323-339}$ (Robertson et al., 2000) were kindly provided by Dr. Xi Yang (University of Manitoba, Department of Medical Microbiology). The University of Manitoba's Review Board approved all animal studies.

Plasmids, lentiviral vectors production. 293T cells used for virus production and titration were cultured in IMDM (HyClone, Logan, Utah) supplemented with 10% fetal bovine serum (FBS) (HyClone, Logan, Utah), and 1% penicillin/streptomycin/glutamate (PSG) (Gibco, Grand Island, N.Y.). VSV-G pseudotyped lentiviral vectors (SIN18-cppt-RhMLV-E, Cppt-2E in short, FUGW, TRIP-GFP, PGK-C) were prepared in 293T cells, concentrated, and titered as described previously. FG12h1siluc and Cloning of the shRNA sequences into lentiviral vectors was described previously (Qin et al., 2003; Stewart et al., 2003). pLKOCD40 clones (66243, GCAGGGTACTGGCTAAATAAA (SEQ ID NO:1)), (66244, CCAAAGGATAATGAGATGTTA (SEQ ID NO:2)) were obtained from Open Biosystems (Huntsville, Ala.); FG12-siCD40#1, TACCATTTAGTTCTTGAATAA (SEQ ID NO:3); FG12-siCD40#2, AAAGGTGGTCAA-GAAACCAAA (SEQ ID NO:4); FG12-siCD40#3, GTGGT-GTATTGTAGAAATTAT (SEQ ID NO:5); FG12-siCD40#4, CTGGACAAGCTGTGAGGATAA (SEQ ID NO:6); FG12-siCD80, TTACAACTCTCCTCATGAA (SEQ ID NO:7); and FG12-siCD86, TCTACGACTTCACAATGTT (SEQ ID NO:8). The locations of the CD40 siRNA sequences on CD40 mRNA are shown in FIG. 1.

DC preparation, transduction and immunizations. The murine BMDC were generated from bone marrow precursors as previously described (Inaba et al., 1992). Briefly, mouse bone marrow cells were extracted from the femura and tibiae of C57/B6 mice, and were plated at $1 \times 10^6$ cells/mL in RPMI 1640 (HyClone) medium supplemented with PSG (Invitrogen), 2-ME, 10% FBS (HyClone), and 20 ng/mL GM-CSF (PetroTech). Culture medium was changed every 2 days. If required, LPS (Sigma) was added to the culture at 10 µg/mL 18 hours before cells were harvested. Transduction of DC were carried out by adding of viral supernatant (at various MOIs, 0.28 mL per well) in the presence of 8 µg/mL of Polybrene (Sigma, St. Louis, Mo.) to the adherent cells on D2 BM culture. Cells were incubated for 3 hours at 37° C. and 5% $CO_2$. Virus-containing supernatant was removed at the end of transduction. Transduced cells were cultured in 0.5 mL GMCSF-conditioned medium as described above. Mock DC or transduced DC selected by puromycin were pulsed with OVA protein (Sigma) overnight before LPS stimulation. They were harvested on D9, and were washed at least three times using PBS. $1\times10^6$ DC were injected i.v. Immunized mice were sacrificed 5 days after immunization, and T cells were sorted to detect OVA-specific immune response.

Flow cytometry. Fluorochrome-conjugated antibodies (CD11c, CD40, CD86, CD80, IL-12) were all purchased from BioLegend (San Diego, Calif.). The fluorescence profile was generated on a BD FACSCalibur Flow Cytometer. 10000 events of gated population was collected and analyzed. Histogram and density plots were produced by the FCS Express version 2.0 (De Novo Software, ON). In intracellular staining of IL-12, DCs were treated with BFA (10 µg/mL) (Sigma) 6 hours before harvest to block the secretion of IL-12. DCs were then collected and stained with Phycoerythrin conjugated (PE) anti-mouse IL-12 as indicated.

Lymphocyte proliferation assay. BALB/c splenic and lymph node T cells were sorted using CD90 (Thy1.2) MicroBeads (Miltenyi Biotec) The T cells of allogeneic animals were resuspended in PBS at $2\times10^7$/ml, and were then mixed with equal volume of 3 µM CFSE. The reaction was quenched using 100% FBS. These labeled cells were then washed carefully before use. Irradiated DC and CFSE labeled T cells were cocultured on a round bottom 96-well plate (Corning) at different ratios for 3 days. The supernatant of culture was collected for cytokine detection using ELISA, the proliferation of T cells was measured by CFSE dilution. In the in vitro assay of Ag-specific T cell priming, $1\times10^6$ lentiviral vector transduced DC were used to immunize mice via i.v. after they were pulsed with OVA protein (Sigma, St. Louis, Mo.), and stimulated by LPS. Immunized mice were sacrificed 5 days after immunization, and T cells were sorted using CD90 (Thy1.2) MicroBeads (Miltenyi Biotec, Auburn, Calif.). Purified T cells were labeled with CFSE, and were co-cultured with OVA pulsed DC for 96 hours. T cell proliferation was evaluated by the dilution of CFSE dye in FACS.

Cytokine production detected by ELISA. The IL-1β production in the supernatant of DC culture was quantified as described previously (Hoeck and Woisetschlager, 2001). Monoclonal anti-mouse IL-1β (Biolegend, San Diego Calif.) was used as capture antibody and biotinylated anti-mouse IL-1β was used as detecting antibody. Binding was detected by streptavidin-alkaline phosphatase and PNPP substrate (Sigma, St. Louis, Mo., USA). The sensitivity limit of ELISA was 0.016 ng/mL. Each data point represents reading from a minimum of three independent assays performed in triplicate.

Results and Discussion

Figure 2B:
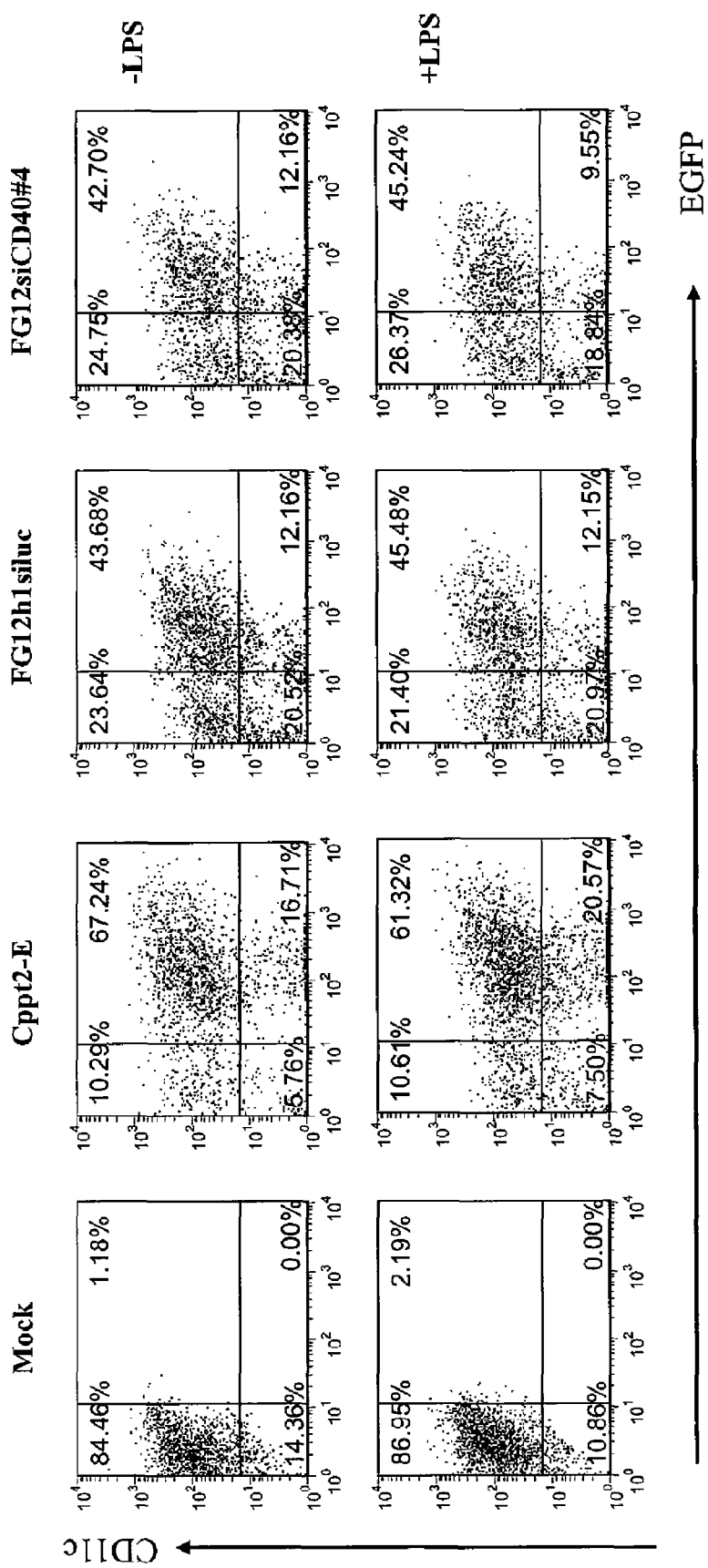

Efficient transduction of DC using lentiviral vectors was established. A lentiviral vector was employed that expressed an EGFP transgene (Cppt2E) (Tran and King, 2007), and a shRNA-expressing lentiviral vector that concomitantly expressed the EGFP reporter gene (FG12H1Siluc, FG12SiCD40#4) to optimize transduction efficiency of DC in the transduction protocol. DC were derived from bone marrow cultured in GMCSF-conditioned medium in vitro. These CD11c$^+$ DC expressed no/low surface expression of co-stimulatory molecules (CD86, CD40) (FIG. 2A mock; CD80, data not shown), thus resembling an "immature" DC phenotype. Upon LPS stimulation, they undergo a maturation process that up-regulated surface expression of these co-stimulatory molecules (FIG. 2A mock). Transduction efficiency was evaluated by the percentage of EGFP$^+$CD11c$^+$ cells by flow cytometry. Efficient gene transfer and transgene expression of EGFP were established in the transduced DC. Greater than 80% CD11c$^+$ DC transduced in the transduction protocol (FIG. 2B).

Figure 2C:
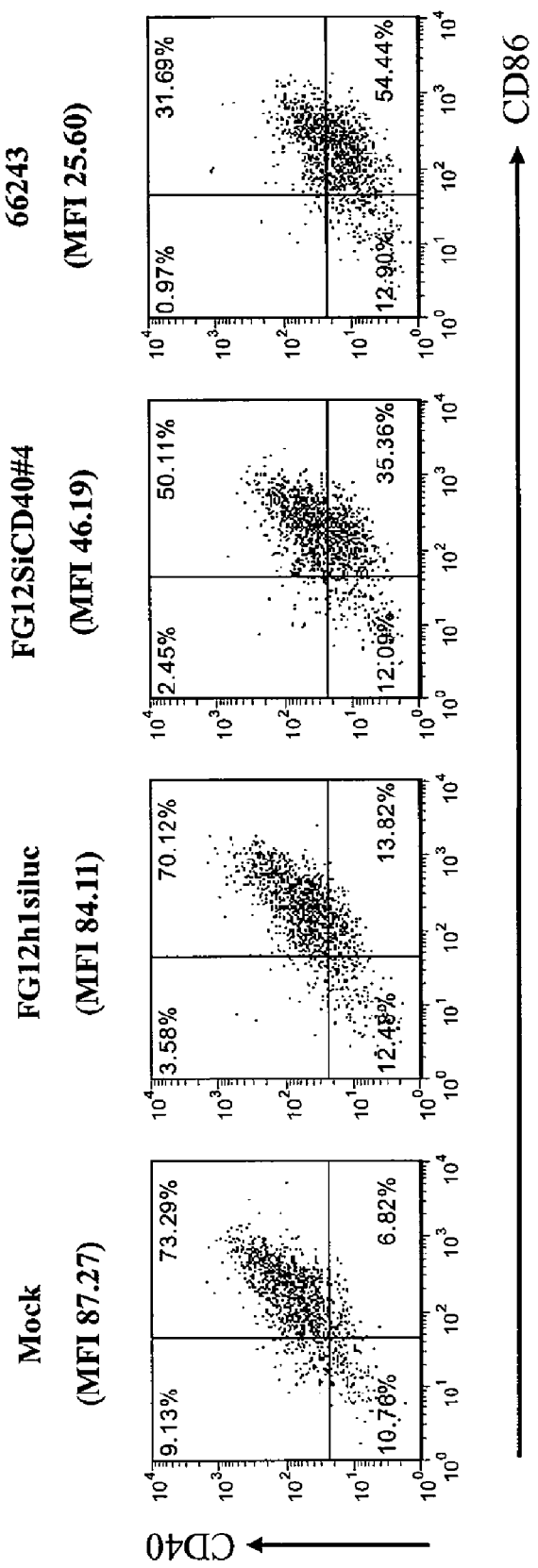

Although lentiviral transduced DC that were genetically modified to over-express specific Ag has been well documented in its ability to prime Ag-specific immune responses in vitro and (He et al., 2005; Kung et al., 2005), introduction of shRNA into DC, however, raises concern as to whether the presence of "foreign" RNA may trigger pathogen pattern-recognition receptors that will alter normal DC properties. A current model suggests that TLR-induced immunostimulation by RNA is determined by the length, sequence, form of RNA delivered, and the cell type studied (Robbins and Rossi, 2005). It is therefore important to examine functional characteristics of gene silencing and the potential immunostimulation in a system-specific manner. A number of lentiviral vectors were constructed and identified that expressed shRNA sequences against different target sequences/genes, such as the irrelevant luciferase gene (FG12H1SiLuc, irrelevant target specificity control), and DC co-stimulatory molecules (CD40, CD86 and CD80). The CD40-silencing constructs, FG12H1Si#4, 66243, were capable of mediating 3-fold and 10-fold down-regulation of the mean florescence intensity of surface CD40 expression respectively when compared to the mock and irrelevant FG12H1SiLuc control (FIG. 2C). The gene silencing of CD40 was specific because surface expression of CD86 was not affected in these transduced DC (FIG. 2C). The lentiviral vectors that expressed CD86 and CD80 shRNA target sequences did not induce any CD86 and CD80 gene silencing respectively in the transduced DC (data not shown), suggesting that the predicted sequences were ineffective in gene silencing of these two genes.

This panel of lentiviral vectors that had different gene silencing capability was used to examine whether lentiviral vector-mediated delivery of the shRNA would induce unwanted, non-specific DC stimulations or functional impairments in the DC maturation process. In exposure to external stimulations by toll-like receptors, the immature DC undergoes a maturation program that up-regulates surface expression of their co-stimulatory molecules, and production of pro-inflammatory cytokines (such as IL-1beta and IL-12). These mature DC are functionally active in presenting Ag and priming Ag-specific T cells in vitro and in vivo. Bone marrow derived DC were transduced with these lentiviral vectors, and examined for any changes in their phenotype, cytokine production and their ability to induce Ag-specific T cell proliferation in vitro and in vivo. Mock-transduced DC (not transduced by any lentiviral vectors) was used as a negative control. No spontaneous maturation or activation was detected in all of the transduced DC when compared to the mock-transduced DC control. The transduced DC expressed no/low surface expression of co-stimulatory molecules (CD86, CD80 and CD40) (FIG. 2A, top panel). They did not produce any detectable IL-1β or IL-12 (data not shown).

Next, LPS was added to these DC cultures to test whether the shRNA-transduced DC were impaired in DC maturation. No impairment of LPS-induced maturation was detected in these transduced cells when compared to the mock control. LPS stimulated both mock and transduced DC to up-regulate co-stimulatory molecules (such as CD40 and CD86) on the surface (FIG. 2A), and to produce IL-1β and IL-12. The FG12SiCD40#4 transduced DC (that expressed an effective RNAi sequence to down-regulate CD40 expression) produced similar responses in IL-1β, IL-12 and CD86 upregulation upon LPS stimulation when compared to the mock, FG12H1SiLuc controls and other shRNA lentiviral vectors that were not effective in silencing CD80, CD86 or CD40.

Collectively, the data established that lentiviral vector delivery (and de novo expression) of these shRNA sequences in the transduced DC did not induce or impair DC activation/maturation, and was independent of the gene silencing activities.

Figure 3A:
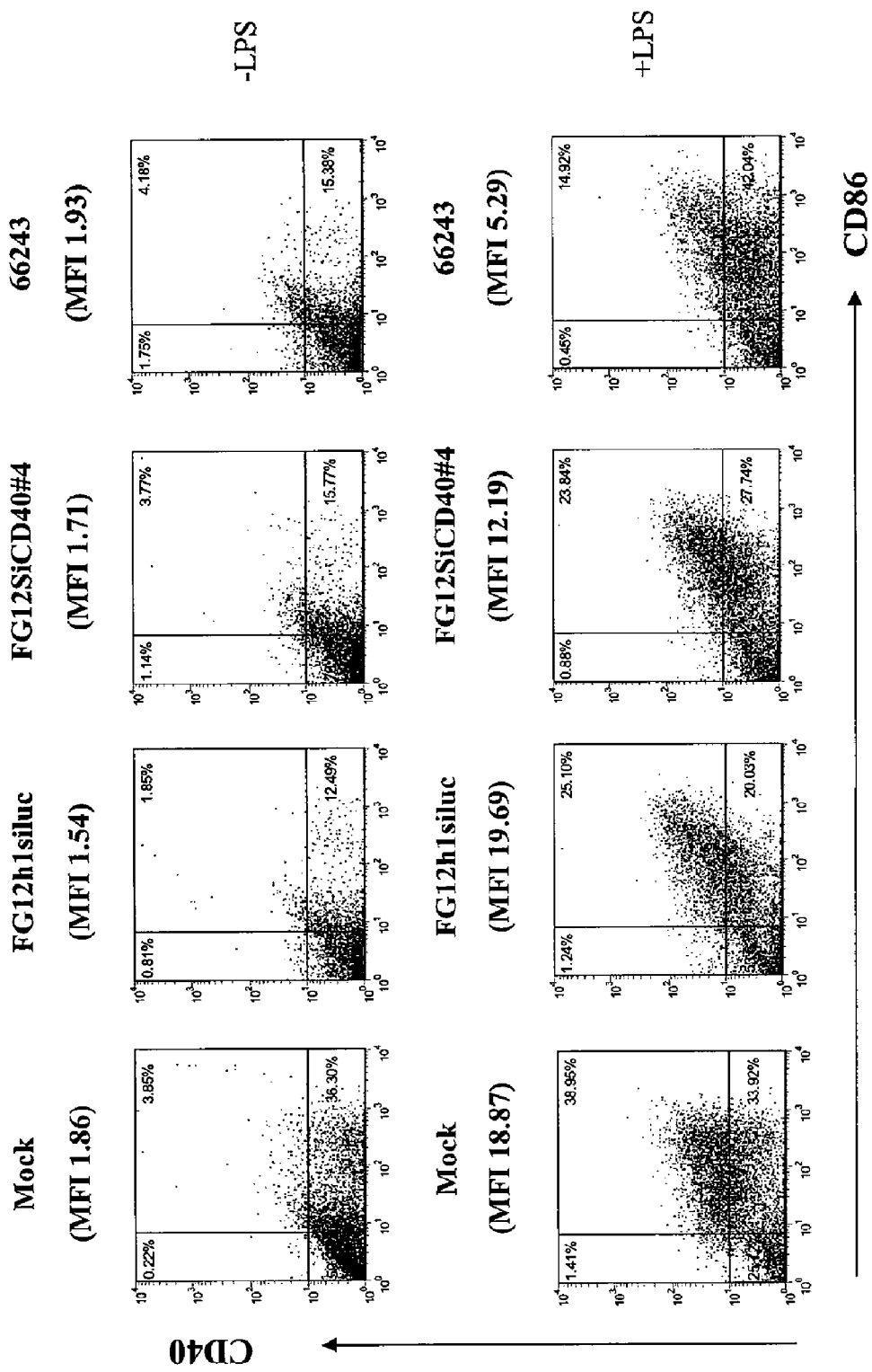
FIG. 3. Lentiviral vectors deliver short interfering RNA into bone marrow derived dendritic cells without functional impairments. A) Lentiviral vectors were highly efficient in transducing DC. Over 85% of CD11c$^+$ was transduced. B) Bone marrow derived DC were immature in phenotype (no/low expression of CD40, CD86 co-stimulatory molecules). Upon LPS stimulation, both mock and the transduced DC upregulated surface expression of CD40 and CD86. The shRNA-expressing lentiviral vectors that down-regulate CD40 expression at different levels specifically. The CD40-silencing constructs, FG12H1Si#4, 66243, were capable of mediating 3-fold and 10-fold down-regulation of the mean florescence intensity of surface CD40 expression respectively when compared to the mock and irrelevant FG12H1SiLuc control. The gene silencing of CD40 was specific because surface expression of CD86 was not affected in these transduced DC. C) Mock and shRNA-transduced DC produced comparable level of IL-1β upon activation. No spontaneous DC activation (IL-1β production) was observed (data not shown) in the supernatant of a panel of lentiviral vectors target different molecules was examined. In the presence of LPS stimulation, Mock and shRNA-transduced DC produced comparable level of IL-1β as detected by ELISA. "Other siRNA sequences" included the CD80, CD86 shRNA sequences that did not mediate down-regulation of CD80, CD86. ShRNA-transduced DC were not impaired in LPS-induced IL-12 production. Mock and shRNA-transduced DC were analyzed for IL-12 production using intracellular cytokine staining, and analyzed in flow cytometry.

FG12siLuc and 66243 vectors were used to further examine the functional ability of these transduced DC to induce allo-specific T cell proliferation in vitro, and to prime an OVA-specific T cell response in vivo. The CD40 co-stimulatory molecule has previously been shown to be essential in the activation of naïve allogeneic T cells in vivo but not in vitro (Haase et al., 2004). This was confirmed using CD40-/- DC in an allogeneic MLR in vitro (FIG. 3A), and therefore used this system to examine any functional impairment of the transduced DC unrelated to the down-regulation of CD40 expression we observed in the 66243-transduced DC. The mock and the transduced DC showed no difference in the allogeneic T cell proliferative responses, as determined by CFSE dilution (FIG. 3A) and 3H-thymine proliferation assays (data not shown). In addition, further enhancement of CD40 down-regulation by co-transduction of two CD40-silencing shRNA vectors (66243+FG12siCD40) did not alter the activation of allogeneic T cells in vitro (FIG. 3A).

Figure 3B:
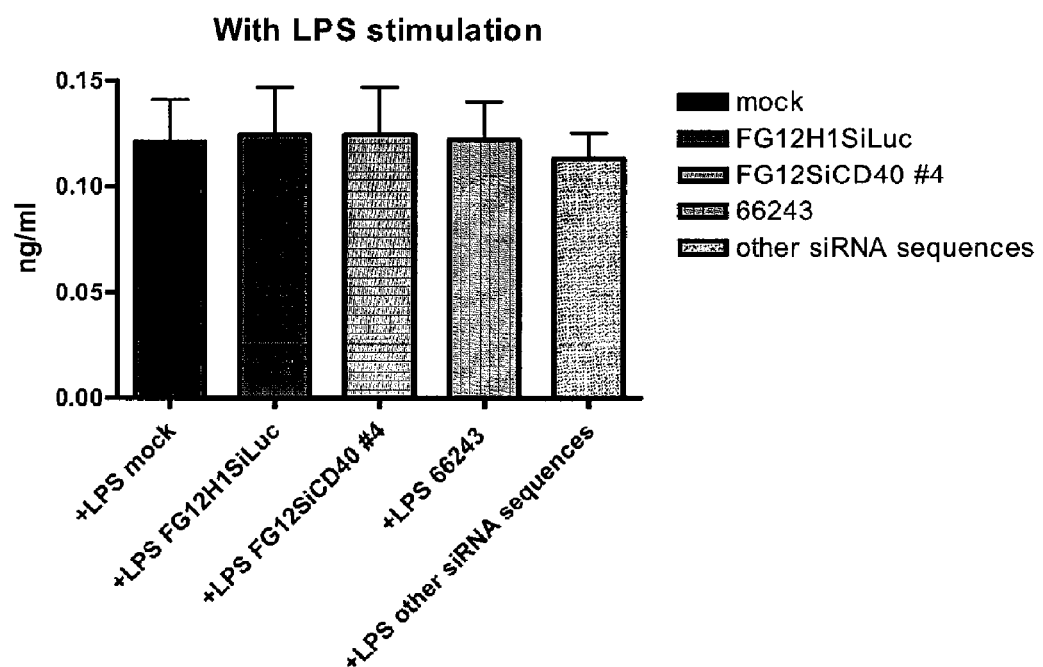
Figure 3C:
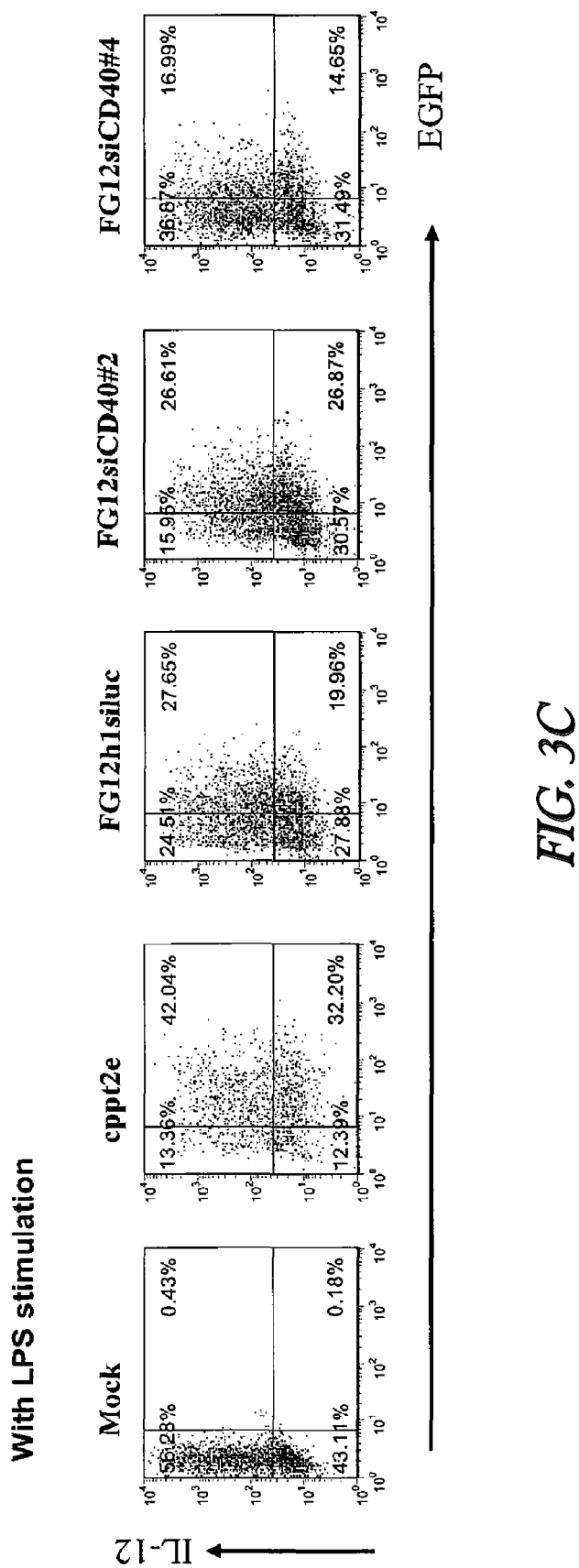

FG12siLuc-transduced DC were used to test the ability of the shRNA-transduced DC to prime an Ag-specific T cell response in vitro. Purified T cells of the OVA-DO.11 TCR transgenic animals were used as responder T cells in a co-culture assay to test whether shRNA-transduced DC were impaired in their ability to prime naive Ag-specific T cells in vitro. Both the mock and the FG12H1SiLuc transduced DC induced OVA-specific T cell proliferation in vitro (FIG. 3B). To further test their ability to prime OVA-specific T cells in vivo, mock transduced DC and FG12siLuc-transduced DC were pulsed with ovalbumin (OVA) protein Ag, and adoptively transferred into syngeneic naïve recipient C57BL/6 mice. The immunized animals were sacrificed and analyzed for OVA-specific T cells in a proliferation assay. As expected, no OVA-specific T cell proliferation was observed in the naïve animals, and in the immunized animals when the OVA Ag was absent in the assay. Induction of OVA-specific T cells was observed in both groups of the mice that were immunized with the Mock-transduced DC and the FG12siLuc-transduced DC (FIG. 3C), demonstrating that delivery and expression of a shRNA sequence by lentiviral vectors did not induce any apparent changes in Ag-priming ability of DC non-specifically in vivo.

Figure 4A:
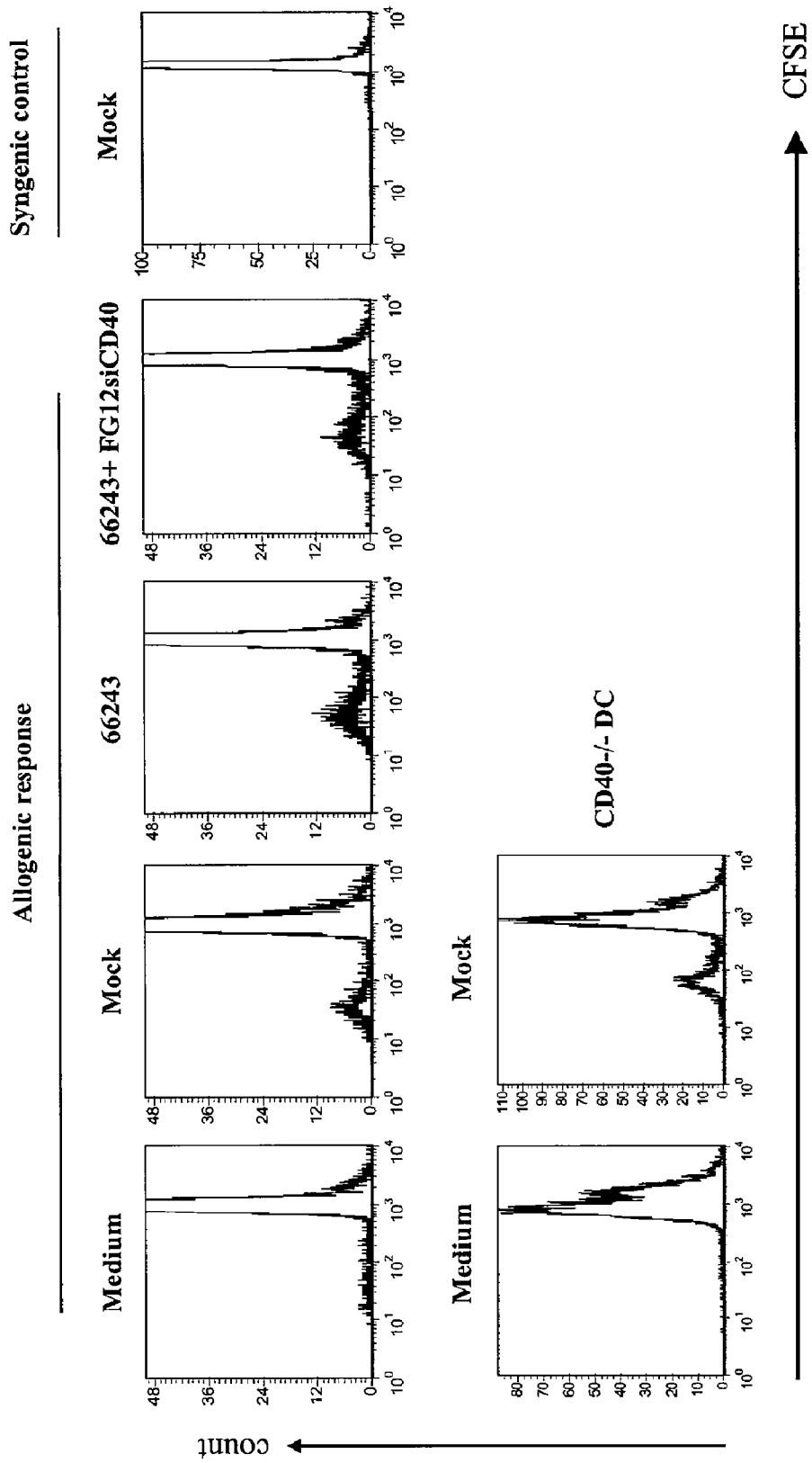
FIG. 4. Lentiviral vectors deliver short interfering RNA into bone marrow derived dendritic cells without impairing antigen presenting ability of these DC. A) Mock-transduced and shRNA-transduced C57/BL6 DC induced similar allogeneic proliferative T cell response in vitro. B6 GMDC was transduced with either 66243 alone or a combination of 66243 and FG12SiCD40. After puromycin selection, these cells were then treated with Mitomycin C and co-cultured with allogeneic Balb/c T cells for three days. The proliferation of T cells was measured by CFSE dilution. T cells cultured with medium or mock-transduced DC were used as control. C57/BL6 T cell cultured with C57/BL6 DC as syngeneic control. DC of CD40−/− immunodeficient was used as a control in this assay to demonstrate allogeneic T cell proliferative response in vitro is independent of CD40. B) ShRNA-transduced DC were capable of priming Ag-specific T cell responses in vitro. DO11.10 T cells were purified by positive selection of CD90.1 via AutoMacs. Purified T cells were labeled with CFSE and co-cultured with primary DC at a ratio of 1:10 with OVA peptide SIINFEKL (SEQ ID NO:9) or ISQAVHAAHAEINEAGR (SEQ ID NO:10). OVA-specific T cell proliferation was measured by CFSE dilution after 3 days of culture. C) Genetic modified DC did not support T cell priming in vivo. DC were transduced with FG12H1SiLuc and 66243, respectively on D2 culture. Transduced cells were selected by puromycin on D7, and matured by 1 µg/mL LPS 18 hours before harvest. Harvested DC were phenotyped, and were used to immunize mice (i.v. 1×10⁶ per mouse). 5 days after immunization, lymph node cells were obtained from immunized mice, and were labelled with CFSE. They were co-cultured with primary DC at a ratio of 10:1 with or with the presence of OVA protein. The proliferation of OVA-specific T cell was measured by CFSE dilution after 4 days of co-culture.
Figure 4B:
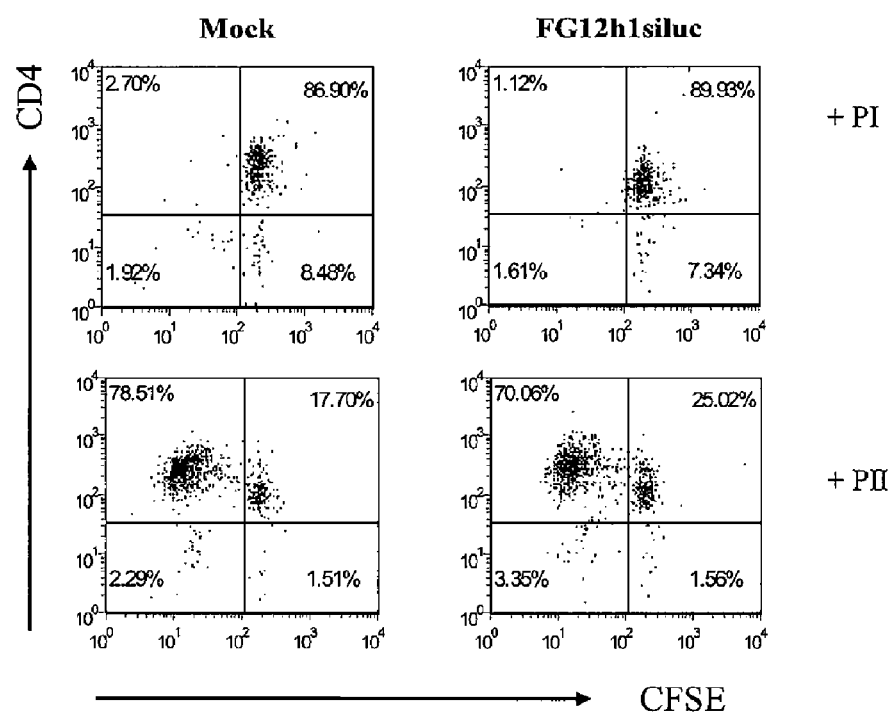
Figure 4C:
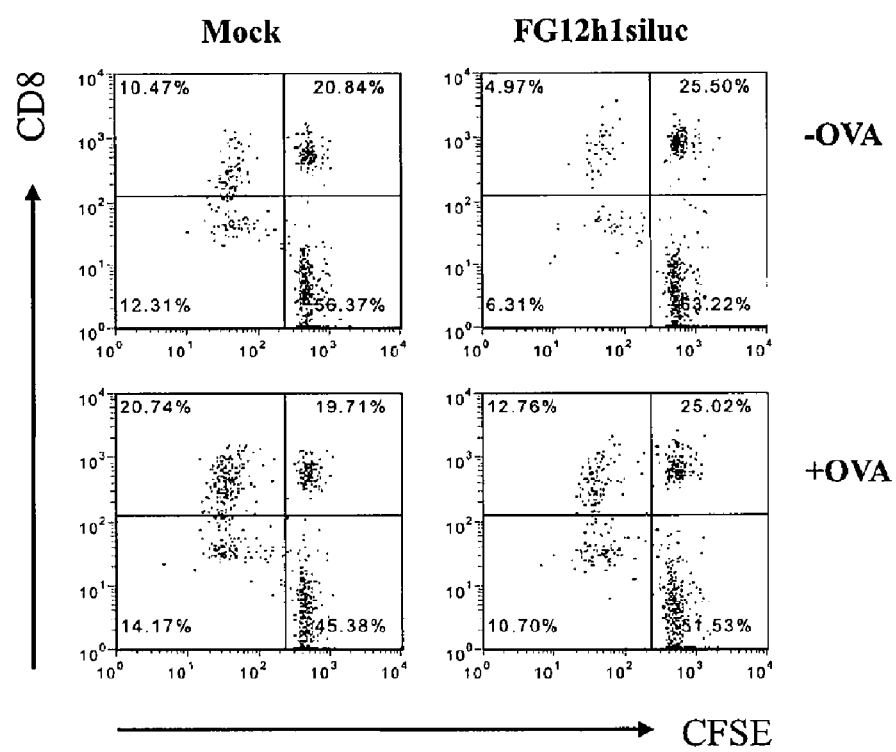
Figure 5A:
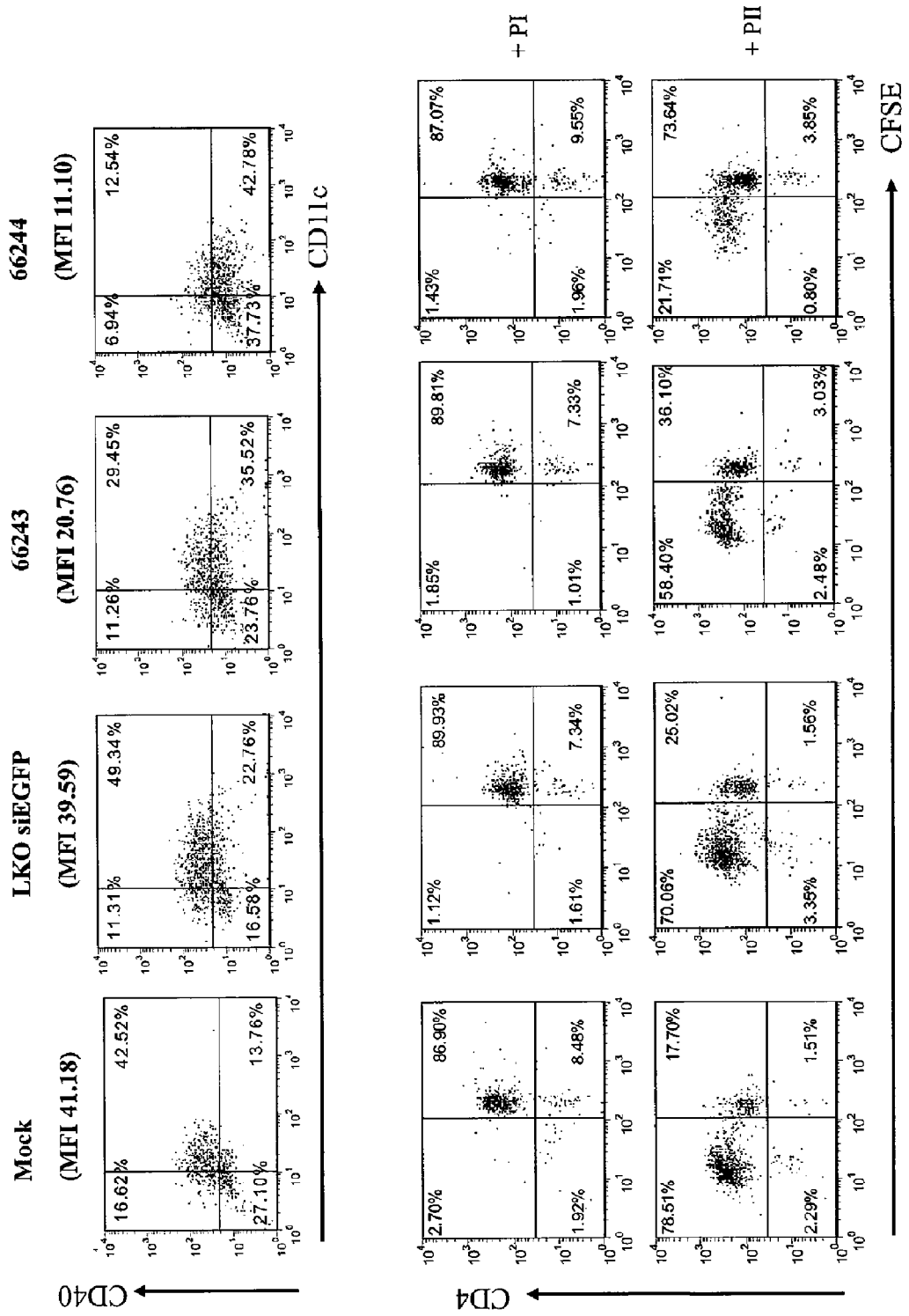
FIG. 5. Different levels of CD40 surface expression on the LPS-matured DC will have different impacts on naïve T cell activation in vitro. A) Down-regulation of CD40 suppressed OVA-specific T cell proliferation in vitro. DO11.10 T cells were purified and labeled with CFSE. They were co-cultured with primary DC (mock or transduced) at a ratio of 1:10 with OVA peptide SIIFEKL (SEQ ID NO:17; PI, irrelevant peptide control) or ISQAVHAAHAEINEAGR (SEQ ID NO:10; PII, Antigenic peptide for DO11.10 T cells). OVA-specific T cell proliferation was measured by CFSE dilution after 3 days of culture. Empty LKO and LKOsiEGFP (that has a shRNA sequence against irrelevant EGFP) vectors were used as specificity control for 66243 and 66244 constructs. Transduced DC (CD40$^{med}$, CD40$^{low}$) were selected by puromycin before co-culture. B) CD40$^{low}$ but not CD40$^{med}$ DC induced T cell apoptosis in vitro. Naïve OVA-specific DO11.10 T cells were purified and co-cultured with Ag-pulsed primary DC (mock or transduced) as described in A. Apoptotic cells were identified by Annexin V staining in FACS on Day 3.
Figure 5B:
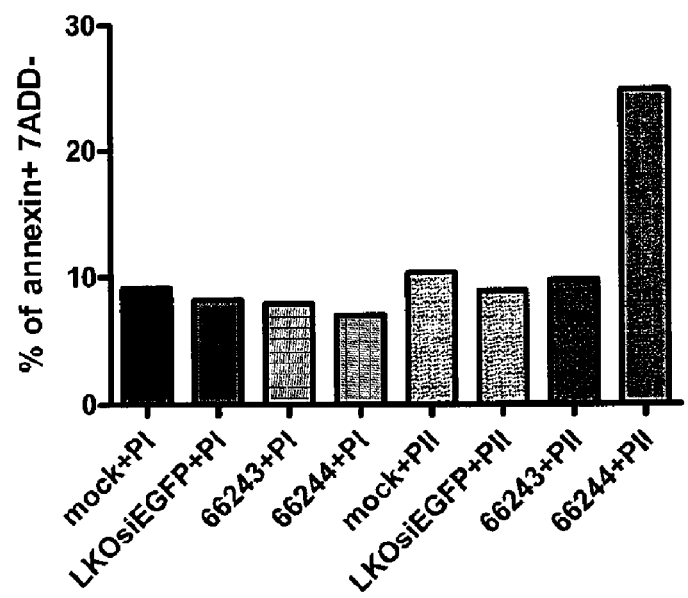
Figure 6:
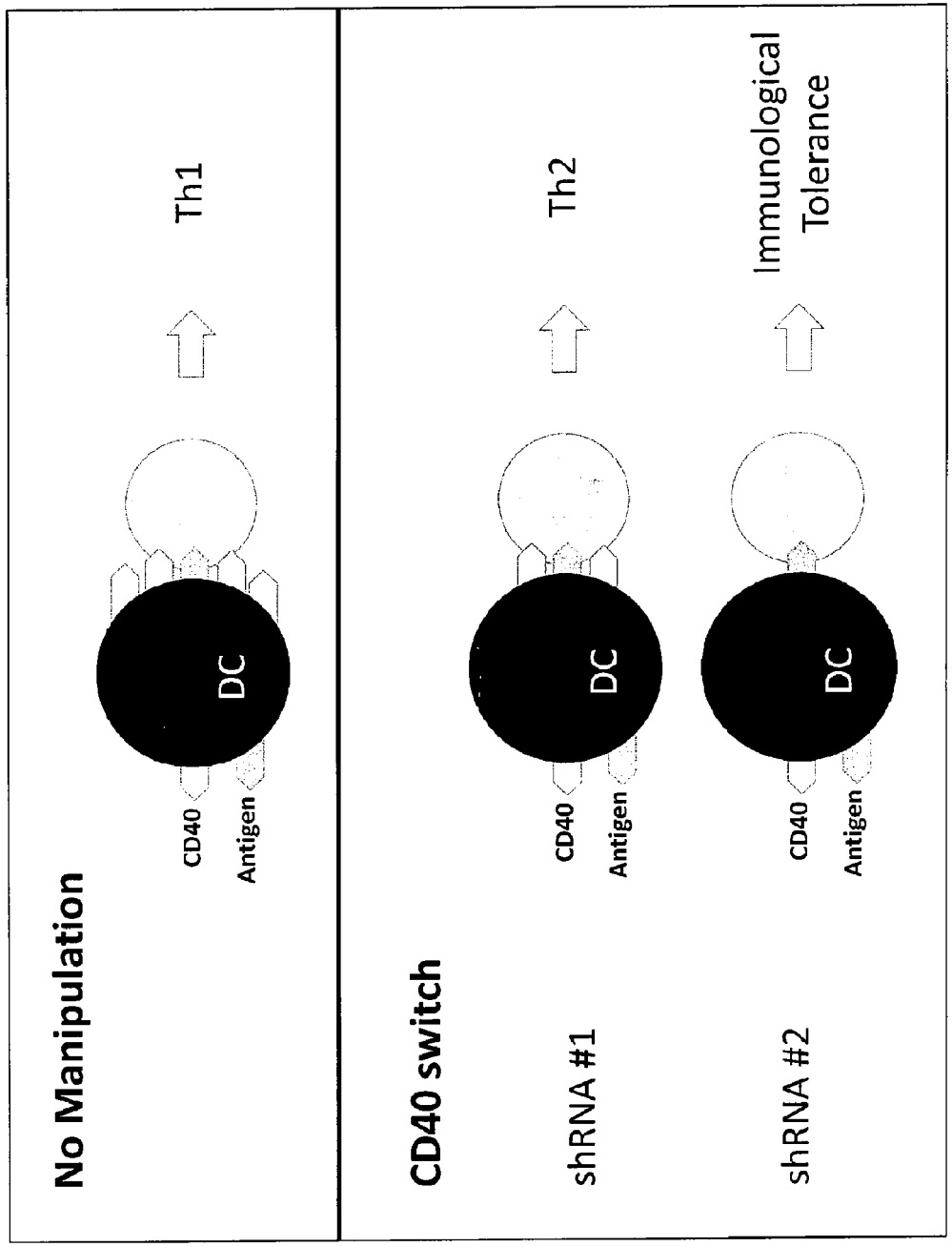
FIG. 6. Schematic of CD40 switch in DC.

If the choice of the sequence encoded in the dsRNA contributes to the potency of the dsRNA in degradation of target mRNA (Reynolds et al., 2004), the use of these sequences in the lentiviral vector system would allow us to regulate different levels of surface expression of a co-stimulatory molecule reproducibly and stably. The CD40 co-stimulatory molecule was used to test whether quantitative expression of this molecule will affect DC function in vitro. CD40 shRNA-containing lentiviral vectors (66243, 66244) was used in the established transduction protocol to generate DC that expressed medium ($CD40^{med}$) and low levels of CD40 ($CD40^{low}$), respectively, on the cell surface (FIG. 4). They were pulsed with OVA peptide I (irrelevant control), or OVA peptide II (OVA antigenic peptide specific to DO.11 TCR). Purified T cells of the OVA-TCR transgenic animals were used as responder T cells in a co-culture assay to test whether shRNA-transduced DC were impaired in their ability to induce Ag-specific T cell proliferation in vitro. Levels of $CD40^{low}$ down-regulation were found correlated to the suppression of naive OVA-specific T cell proliferation in the OVA transgenic T cells in vitro (FIG. 4A). Interestingly, only $CD40^{low}$ DC induce significant apoptosis in vitro (FIG. 4B). The data demonstrated that lentiviral vector-mediated RNA interference supports quantitative analysis of a co-stimulatory molecule in DC function. Different levels of CD40 surface expression on the LPS-matured DC will have different impacts on naïve T cell activation in vitro.

Conclusions

Dendritic cells (DC) are specialized regulator of innate and adaptive immunity. Advances in using lentiviral vectors to deliver short hairpin RNA (shRNA) in specific gene silencing provide a unique tool to generate stable genetically modified DC to direct different cellular responses (such as Th differentiations or immunological tolerance) in vivo. This approach allows the examination of the importance of quantitative expression of co-stimulatory molecule(s), such as CD40, in determining different functional properties of DC to tolerize, activate or polarize antigen-specific Th1/Th2 immune responses in vivo. The ability to regulate types of T cell responses against specific antigens is useful in the development of vaccines and therapeutic approaches to infectious diseases.

Example II

Replication-incompetent HIV-1 based lentiviral vector is now emerging as a promising delivery system to genetically modify DC through antigen recognition, co-stimulatory molecules and/or polarization signals for the manipulations of Ag-specific immunity in vivo. The following will discuss some of the recent advances in the uses of lentiviral vectors in DC-based immunotherapy.

Manipulation of Immune Responses by Genetically Engineered Dendritic Cells

Dendritic cells (DC) are professional antigen presenting cells (APC) that initiate and regulate immune responses. They present antigenic peptides in the context of major histocompatibility complex (MHC)/Peptide complexes (Signal 1) to engage cognate T cell receptors of T cells to define antigen (Ag) specificity. They possess a number of co-stimulatory molecules (Signal 2) to regulate optimal T cell activation. Binding of B7-1 and B7-2, for examples, to CD28 or CTLA-4 respectively on T cells will provide the co-stimulatory activity for naïve T cell activation or inhibitory activity of T cell activation. A third signal (the polarization signal), which comes from cytokines or chemokines released by the APC, will regulate differentiation of naïve T cells into distinct types of T helper cells (O'Sullivan et al., 2003; Sharpe et al., 2002; Kalinksi et al., 2005; and Reis et al., 2006). Tight regulation of these signals upon DC/T cell interaction will ultimately determine the functional ability of DC to induce Ag-specific tolerance, Ag-specific immunity or specific differentiation of T helper subsets.

The ability to generate DC of defined therapeutic property therefore holds great promises in transplantation, as well as immunotherapy of cancer, infectious diseases, allergy and autoimmunity. Genetic manipulation of DC is an attractive approach because molecules such as protein antigens (Ag), co-stimulatory molecules or cytokines can be expressed and manipulated (in the forms of DNA, RNA, short interference RNA or short hairpin RNA) directly in the DC by viral and non-viral gene delivery systems. Indeed, different strategies have been developed to modify DC ex vivo for manipulations of Ag-specific immunity in vivo (Tables 3 and 4).

TABLE 3

Induction of anti-tumor and anti-viral responses using genetically modified DC

| Diseases | Targeting strategy | Targeting molecules | Delivery system | Ref |
|---|---|---|---|---|
| Tumor | Signal 1 | TAA encoding cDNA | liposome | Pecher et al., 2002 |
| | | TAA encoding cDNA | Liposome/Adenovirus | Pecher et al., 2001 |
| | | TAA encoding mRNA | Electroporation | Kyte et al., 2007 |
| | | TAA encoding cDNA | Adenovirus | Tsao et al., 2007 |
| | | TAA encoding cDNA | lentivirus | Mossoba et al., 2008 |
| | | Mutated mRNA of TAA | Electroporation | Abdel-Wahab et al., 2003 |
| | Signal 2 | TAA + CD40L | Adenovirus | Zhang et al., 2003 |
| | | OX40L | Retrovirus | Yanagita et al., 2004 |
| | | CD40L/RANKL/4-1BBL | Adenovirus | Yurkovetsky et al., 2006 |
| | | CD80 | Avipox vector | Tsang et al., 2001 |
| | | CD70 | Electroporation | Keller et al., 2009 |
| | | CD54 (ICAM-1) | Avipox vector | Yang et al., 2005 |
| | | CD58 (LFA-3) | Avipox vector | Yang et al., 2005 |
| Virus infection | Signal 1 | Influenza antigen M1 mRNA/cDNA | Electroporation | Strobel et al., 2000 |
| | Signal 1 | CMV antigen IE1 | rAAV | Yu et al., 2008 |
| | Signal 1 | HIV-1 | Sendai virus/adenovirus | Hosoya et al., 2008 |
| | Signal 1 | HCV-S/HCV-NS | Lentivirus | Jirmo et al., 2010 |
| | Signal 1 | HCV NS cDNA/mRNA | Electroporation | Yu et al., 2008 |
| | Signal 1 | HCV NS | Adenovirus | Zabaleta et al., 2008 |
| | Signal 1 | HIV-1 Gag and Env proteins. | Electroporation | Van Gulck et al., 2006 |
| | Signal 1 | HBsAg | Adenovirus | Huang et al., 2006 |

Abbreviations: Tumor Associated Antigen (TAA); Interferon-gamma-Inducible Protein-10 (IP-10); secondary lymphoid tissue chemokine (SLC); monokine induced by IFN-gamma (Mig); recombinant adeno-associated virus (rAAV); HBV surface surface antigen (HbsAg); HCV structural antigen (HCV-S) and non-structural antigen (HCV-NS)

TABLE 4

Induction of immunological tolerance in transplantation or autoimmune diseases

| Diseases | DC source | Delivery system | Targeting molecules | Therapeutic effect | Ref |
|---|---|---|---|---|---|
| Transplantation | Donor/in vitro | adenovirus | sTNFRI | Prolonged cardiac allograft survival | Wang et al., 2006 |
| | Donor/in vitro | adenovirus | IL-10 | Prolonged cardiac allograft survival | Zhang et al., 2004 |
| | Donor/in vitro | Lipofectamine | FasL | Prolonged cardiac allograft survival | Min et al., 2000 |
| | Donor/in vitro | Electroporation | CTLA-4 | Prolonged islet transplant survival | O'Rourke et al., 2000 |
| | Donor/in vitro | Retrovirus | TGF-β | Prolonged heart transplant survival | Takayama et al., 2002 |
| | Recipient/in vitro | Passive pulsing | NF-κB ODN | Prolonged cardiac allograft survival | Tiao et al., 2004 |
| | Recipient/in vitro | adenovirus | MHC-I | Prolonged cardiac allograft survival | Fry et al., 2002 |
| Autoimmune disease | In vitro | Lentivirus | RelB-specific shRNA | Prevent development of EAMG | Zhang et al., 2009 |
| | In vitro | Lentivirus | IL-4 | Prevent NOD | Creusot et al., 2008 |
| | In vitro | Adenovirus | Galectin-1 | delayed onset of NOD | Perone et al., 2006 |
| | In vivo | Lentivirus | BAFF | Ameliorate RA | Lai et al., 2008 |
| | In vitro | Electroporation | MOG + TRAIL | Prevent EAE | Hirata et al., 2005 |
| | In vitro | Adenovirus | Suppressive TCR mimic peptide | Abrogated EAE | Mahnke et al., 2003 |
| | In vitro | Electroporation | c-MIR (MHC-II inhibitor) | resistance to EAE | Ohmura-Hoshino et al., 2003 |
| Allergic disease | In vitro | Lentivirus | IL-10 | Reversed experimental asthma | Henry et al., 2008 |
| Inflammation | In vitro | Adenovirus | IL-4 | Inhibited inflammation DTH | Kim et al., 2007 |

Abbreviations: soluble TNF-α receptor type I (sTNFRI); Fas ligand (FasL); oligodeoxyribonucleotides (ODN); B cell-activating factor (BAFF); myelin oligodendrocyte glycoprotein (MOG); TNF-Related Apoptosis Inducing Ligand (TRAIL); experimental autoimmune myasthenia gravis (EAMG); non-obese diabetic (NOD); autoimmune arthritis (RA); Prevent experimental autoimmune encephalomyelitis (EAE); inflammation of delayed-type hypersensitivity (DTH)

Lentiviral Vectors and Dendritic Cell Transductions

Replication-incompetent HIV-1 based lentiviral vectors are capable of stable transduction of both dividing and relatively quiescent cells. This feature is advantageous over retroviral vectors derived from oncoretroviruses such as Moloney murine leukemia virus (MoMLV) because these retroviral vectors require proliferation of the target cells for integration (Case et al., 1999; Roe et al., 1993). Safety features that safeguard the use of lentiviral vectors in gene therapy in vivo are built into the vector production system. Firstly, accessory genes (vif, vpr, vpu and nef) that are not essential for transduction were eliminated from a packaging construct (Kafri et al., 1997; Kim et al., 1998; Zuffrex et al., 1967). Secondly, the uses of three-plasmid (or four-plasmid) expression system that consists of packaging, envelope and vector constructs have minimized the possibility for generating replication-competent virus through recombination (Mochizuki et al., 1998; Naldini et al., 1996; Naldini et al., 1996). The latter possibility is further minimized by the deletions of the TATA box and binding sites for transcription factors Sp1 and NF-kB, in the U3 region of the 3' long terminal repeat (LTR) of the HIV-1 vectors to inactivate the LTR promoter activities (Mixoshi et al., 1998; Zuffrex et al., 1995). We prepared replication-incompetent, vesicular stomatitis virus glycoprotein (VSV-G) pseudotyped lentiviral vectors by 3-plasmids transfection of highly susceptible 293T cells to obtain high virus titers (typically $10^8$ IU/mL) for primary cell transductions. In the arguably closest model system for human hematopoietic stem cell gene therapy, we demonstrated transduction of autologous CD34$^+$ stem cells and long-term expression of a foreign green florescent protein (GFP) gene in all hematopoietic cell lineages in vivo without the induction of anti-GFP immune responses in the myeloablated rhesus macaques (Kung et al., 2003). The animals remained healthy with no evidence of hematopoietic abnormalities or malignancies in a 5-year long-term study (Kung et al., 1993).

Lentiviral Vectors in Genetic Modifications of DC Ex Vivo

Ex vivo tissue culture conditions for DC and the preparation of high-titer lentiviral vector have been well documented and optimized in recent years (Tuyaerts et al., 2008; Kutner et al., 2009; Ansorge et al., 2009). Lentiviral vector is now emerging as a promising gene delivery vector system for DC because of the relatively high efficiency in the transduction of immature and differentiating DC (Zhang et al., 2009; Veron et al., 2001). Long-term, stable transductions of human monocyte-derived DC, human CD34$^+$-derived DC, and mouse bone marrow derived DC (BMDC) have been reported (Breckpot et al., 2005). In the development of anti-cancer immunotherapy, DCs transduced with a lentiviral vector that expressed a surrogate tumor associated antigen (TAA) ovalbumin (OVA) have been shown to effectively process and present the OVA antigens, and induced OVA-specific T cell responses. A single immunization of the lentiviral vector-transduced DC in a mouse melanoma model induced protective immunity against a lethal dose of the OVA-expressing B16 melanoma cells challenge, as well as therapeutic anti-tumor immunity against the established B16 tumors (He et al., 2005). Other clinically relevant TAAs, such as TRP-2, MAGE-3, Melan/MART-1, and tyrosinase, have been inserted into lentiviral vectors. DCs transduced with these lentiviral vectors effectively presented the TAA to activate established T cell lines or clones specific for the epitopes derived from these TAA (Metharom et al., 2005; Breckpot et al., 2004; Lopes et al., 2006; Metharom et al., 2001; Pullaers et al., 2000). As lentiviral vector-transduced DC induces stronger anti-tumor immunity when compared to peptide/protein-pulsed DC (He et al., 2005), strategies that aim at further stimulating innate immunity to produce inflammatory cytokines for T cell activations may augment the therapeutic efficacy of the TAA-transduced DC in the treatment of cancer. Lentiviral vector transduced DC that over-expressed Toll-like receptor (TLR) or TLR adaptor proteins (e.g., MyD88 and TRIF/TICAM-1) were able to enhance tumor-specific lysis and delay the growth of pre-existing tumor (Akazawa et al., 2007). Gene silencing of A20, a ubiquitin-modifying enzyme that negatively regulated receptor-interacting protein and TNFR-associated factors 2 and 6, in DC resulted in spontaneous production of proinflammatory cytokines such as IL-6, TNF and IL-12p40 (Song et al., 2005). It is also possible to enhance antigen presentation ability of DC by prolonging their life span via gene silencing of the mitogen-inducible nuclear orphan receptor (MINOR) whose expression leads to apoptosis (Wang et al., 2009), or by augmenting co-stimulatory signals on DC using lentiviral vectors to over-express co-stimulatory molecules such as CD40L (Koya et al., 2003) or gp34/OX40L (Kobayashi et al., 2004). Successful cancer vaccine strategy may require not only the induction of potent tumor antigen-specific immune responses, but also a mechanism to overcome tolerance/suppressive mechanisms. Efforts have been made to overcome such tolerance by enhancing Ag presentation abilities of the transduced DC. In a mouse model of aggressive renal cell carcinoma pulmonary metastases, massive metastases resulted in tumor-induced immune tolerance and tumor-related death (Zhang et al., 2005). Zhang et al., transduced hematopoietic stem cells (HSC) to express a surrogate TAA Ag (influenza hemagglutinin, HA), and transplanted these lentiviral transduced HSC in the animals with established pulmonary metastases to provide a constant pool of HA-expressing DC (and progenitors). Upon in vivo GM-CSF-induced DC expansion and adoptive transfer of HA-specific T cells, in vivo derived HA-expressing DC overcame tumor-induced immune suppression, and promoted HA-specific T cell activation that translated into improved survival of the tumor-bearing animals (Zhang et al., 2005). Multiple myeloma (MM) cell lysate-pulsed DC of the MM patients induced higher frequency of CD4$^+$CD25$^{high}$FoxP3$^{high}$ Treg cells, and suppressed activation of T cells (Wang et al., 2009). Han et al. reported that lentiviral transduction of DC from the MM patients to over-express calnexin (CNX), a chaperone protein involved in the proper folding and maturation of glycoproteins, was able to overcome such suppression. As over-expression of CNX in DC upregulated class I MHC and exhibited increased functional avidity (Wang et al., 2009), the ability to activate T cells at a lower threshold may be sufficient to induce the expansion of high-avidity effector T cells in the immunosuppressive tumor microenvironment (Han et al., 2008; Wang et al., 2009).

Lentiviral vectors have also been developed for the immunotherapy of viral infections. Immunizing mice with the lentiviral vector-transduced DC that expressed the immunodominant epitopes of lymphocytic choriomeningitis virus (LCMV) glycoprotein gp33-41 protected the immunized mice from a lethal dose of LCMV challenge (Zarei et al., 2004). Expression of multiple hepatitis C virus non-structural proteins (NS2, NS3, NS4a, b and NS5a, b) in monocyte-derived DC stimulated Ag-specific CD8$^+$ T cell responses against NS3, NS4a and NS5b proteins, suggesting a potential use of lentiviral vectors in anti-HCV vaccine development (Jirmo et al., 2010).

The plasticity of DC functions supports the development of DC-based immunotherapy that suppresses Ag-specific immune responses in autoimmune diseases, allergy or transplantation tolerance. BMDC that were genetically engineered to secrete neuropeptide vasoactive intestinal peptides (VIP) expressed lower levels of CD40 and CD86, produced little IL-12p70 but higher level of IL-10 upon LPS stimulation (Tuscano et al., 2010). A single administration of the VIP-expressing DC decreased clinical symptoms in the experimental autoimmune encephalomyelitis and increased survival rate in the mouse model of peritoneal sepsis (Tuscano et al., 2010). In an experimental autoimmune myasthenia gravis (EAMG) model, administration of lentiviral-transduced DC that encoded short hairpin RNA (shRNA) against RelB gene suppressed the pre-existing immune responses, were able to induce IL-10 and IL-4 production in vitro and in vivo, and decreased anti-AChR IgG, IgG1, IgG2b Ab levels in serum (Zhang et al., 2009). The transduction of DC with lentiviral vectors that expressed IL-10 rendered them tolerogenic in a therapeutic mouse model of asthma (Henry et al., 2008), allergic contact dermatitis (Iglesias et al., 2006).

Direct Injections of Lentiviral Vectors to Genetically Modify DC In Vivo

VSV-G has been widely used in psuedotyping lentiviral vector particles because of the stability, the high titers and the effective transduction of cells of broad tropism. The VSV-G pseudotyped lentiviral vectors are efficient in the transduction of ex vivo manipulated DC for adoptive transfer in vivo, as well as inducing strong Ag-specific cellular and humoral responses in their direct injections in experimental animals in vivo (Dullaers et al., 2006; Breckpot et al., 2007; Esslinger et al., 2003; Palmowski et al., 2004; Rowe et al., 2006; Iglesias et al., 2006; Kim et al., 2005; He et al., 2006a; Chapatte et al., 2006). Intravenous injection of lentiviral vectors transduced cells in liver and MHC II-positive APC in spleen (Vanden-Driessche et al., 2002), and supported long-term gene expression in APC in spleen. Using a GFP-expressing lentiviral vector in the examination of the long-term transgene expression in DC subsets in spleen, Arce et al. demonstrated that intravenous injection of lentiviral vectors transduced proliferating DC precursors that maintained in spleen for at least 2 months. The persistence of the transduced DC precursors led to prolonged Ag presentation and effective T-cell memory (Arce et al., 2009). Esslinger et al. reported that resting DC at the site of subcutaneous injection was selectively transduced. The modified DC homed to draining lymph nodes and spleen where they primed antigen-specific T cells (Breckpot et al., 2007). Skin-derived DC (CD11c$^+$B220$^-$CD8$^-$CD11b$^+$DEC205$^+$) subset, but not langerhans cells or langerin-expressing dermal DC, is the major APC that induces optimal CD8$^+$ T cell responses after intradermal lentiviral-mediated immunization (He et al., 2006a; He et al., 2006b; Furmanov et al., 2010).

Direct administration of lentiviral vectors encoding TAA genes induced more potent TAA-specific immune responses, when compared to the DC that were transduced with lentiviral vectors ex vivo. There were higher number of IFN-γ producing cytotoxic T lymphocyte (CTL), stronger cytolytic activity, that in turn correlated well with a better protective immunity and prolonged survival time (Breckpot et al., 2007). Direct injection of HIV-1 polyepitopes-encoding lentiviral vectors into HLA-A2 or HLA-B7 transgenic mice induced broad CTL response against all 13 epitopes in the HLA-A2 transgenic and 8 out of 12 epitopes in the HLA-B7 transgenic mice along with augmented number of IFN-γ producing T cells (Iglesias et al., 2007). In a pilot study that utilized lentiviral vectors pseudotyped with two VSV-G of non-cross-reactive serotypes in a prime/boost vaccination strategy, Beignon et al. demonstrated that direct injections of the simian immunodeficiency virus (SIV) GAG-encoding lentiviral vectors in cynomolgus macaques elicited robust humoral and cellular immune responses against SIV GAG, and showed protection against SIVmac251 challenge (Beignan et al., 2009).

Use of Genetically Modified DC in Expansion of Specific T Cell Subsets In Vitro

The ability to expand a specific T cell subset with defined functional property in vitro will facilitate greatly the uses of these T cells in clinical applications in vivo (Kalinksi et al., 2010). For example, the αβTCR$^+$CD4$^-$CD8$^-$ double-negative (DN) T regulatory cells are a small population of T cells (of low 1-5% frequency) that are capable of suppressing Ag-specific T cells in inducing immunological tolerance in allograft transplantation (Zhang et al., 2000; Thomson et al., 2007). In a 2C-TCR transgenic mouse model, Thomson et al., transduced recipient-derived mature DC with a lentiviral vector that expressed the allogeneic major histocompatibility complex class I Ld antigen (LV-Ld). These modified DC were able to expand effectively the DN Treg cells, to maintain their ability to suppress CD8$^+$ T cells in vitro and to prolong the survival of the Ld$^+$ skin grafts in vivo (Thomson et al., 2007).

Use of shRNA of Different Gene Silencing Potency to Define DC Functions In Vivo

The increasing number of co-stimulatory molecules identified to date highlights the importance and complexity of co-stimulatory signals in defining DC functions. CD40 is upregulated in the mature immunogenic DC to induce optimal T cell activation. We established a lentiviral system to genetically modulate surface expression levels of CD40 on primary DC (Zhang et al., 2009). Quantitative surface expressions of CD40 were genetically defined by the use of shRNA sequences that target different regions of CD40 mRNA and of different gene silencing potencies. Using the transduced LPS-stimulated DC that expressed different level of CD40 on the cell surface, we demonstrated that the expression levels of CD40 on DC were pivotal in determining the different functional properties of DC to tolerize, activate or polarize antigen-specific Th1/Th2 immune responses in vivo (Zhang et al, unpublished). It thus presented a "switch" that may prove useful in delivering a specific function/therapeutic property of the genetically modified DC in the treatment of immune disorders, such as Type I diabetes.

Use of Non-Integrating Lentiviral Vectors in Transient Genetic Modifications

An important feature of lentiviral vectors is the ability of the viral integrase protein to integrate the gene(s) of interest in the host genome, thus supporting the efficient and long-term gene expression of the transgene in the transduced cells. Although the preferred sites of integrations seem to differ between the lentiviral and retroviral vectors (Felice et al., 2009), there will always be a concern that the vector integrations may pose a risk of the insertional mutagenesis. In applications that do not require a long-lived stable gene expression in dividing cells, non-integrated lentiviral vectors may provide a safer alternative to the current lentiviral-based therapies in driving the expression of the therapeutic gene. Towards this end, integration-deficient lentiviral vectors (that harbored class I mutation of the HIV-1 integrase) were developed for vaccination, and gene therapy in muscle cells and central nervous system (Apolonia 2007; Negri et al., 2007; Rahim et al., 2006). Integrase defective lentiviral vectors were effective in the transduction of human monocyte-derived DC (Negri et al., 2010) and mouse BMDC (Coutant et al., 2008). In a mouse model of West Nile Virus (WNV) infection, a single administration of nonintegrative lentiviral vectors that expressed a secreted form of the envelope of a WNV strain induced robust B cell response, and protected the immunized animals from a lethal WNV challenge (Coutant et al., 2008). Human monocyte-derived DC transduced by the influenza matrix M1 protein-encoding integration defective lentiviral vectors ex vivo were able to induce expansion of M1 primed CD8+ T cells in vitro (Negri et al., 2010).

Development of Novel Lentiviral Vectors in DC-Specific Transductions In Vivo

The successful demonstration of direct administration of the VSV-G pseudotyped lentiviral vectors in the genetic modification of DC in vivo raises the exciting potential of direct administration of the lentiviral vectors in the clinical DC-based applications. However, given the broad cell tropisms of the VSV-G envelope, novel strategies that target genetic modifications or transgene expression to DC (or DC subset) specifically may be highly desirable. It may avoid unwanted "off-target" cell activation, reduce the doses of the vector administration needed in the therapy and also allow specific manipulation of a therapeutic DC function. Two major strategies have been developed to target specific genetic modification of DC. First, transcriptional targeting of DC can be achieved by the incorporation of a DC-specific promoter in the lentiviral vectors. Cui et al. (2002) used the human HLA-DRα promoter in the transduction of human pluripotent CD34+ cells to regulate transgene expression in the HLA-DR+ cells that included differentiated DC (Cui et al., 2002). A DC-STAMP promoter was used to express high level of Ag to eliminate the reactive CD4 and CD8 T cells in peripheral organs and thymus, which led to induction of T cell tolerance in a mouse model of autoimmune diabetes (Dresch et al., 2008). Recently, Zhang et al. cloned a 1.2 kb CD11c promoter into a lentiviral vector to drive transgene expression in DC cells in vitro and in the generation of DC-specific transgenic mice (Zhang et al., 2009). Second, novel designs of DC-specific viral envelope proteins used in the pseudotyping of lentiviral vectors. Towards this end, Morizono et al. modified the sindbis virus envelope protein to express either a Fc-binding protein A domain, a biotin-adaptor peptide or arginine-glycine-aspartic acid RGD peptide. Such modifications supported conjugations of the pseudotyped lentiviral vectors with antibodies of defined Ag specificities, avidin-conjugated specific antibodies or integrin-expressing cells, respectively, for targeted cell type-specific transduction (Morizono et al., 2009; Morizono et al., 2009; Morizono et al., 2005). Mutant sindbis virus envelope glycoproteins were also engineered to bind to the DC-SIGN protein on DC (Dai et al., 2009; Yang et al., 2008; Morizono et al., 2011). A single immunization of these pseudotyped vectors was capable in eliciting Ag-specific immune responses in vivo (Dai et al., 2009; Yang et al., 2008).

Conclusions and Future Perspectives

Deregulation of the host immune system accounts for a large number of immune and inflammatory disorders (e.g., AIDS, cancers, allergy, autoimmune diseases, and graft rejections in transplantation). At present, non-Ag specific approaches with broad immunomodulatory effects (e.g., corticosteroids as anti-inflammatories, cyclosporine to inhibit all T cell activity) are widely used to modify human immune responses. A better understanding of the basic mechanisms underlying DC functional abilities to regulate initiation and activation of the immune system will allow development of selective therapeutic approaches that turn on or off specific and appropriate immune responses without interfering with the remaining human immune capacity. Replication-incompetent HIV-1 based lentiviral vectors are relatively simple to prepare in a standard laboratory (Kung et al., 2009). They present an exciting candidate gene therapy vector for hematopoietic progenitor cells, DC and other primary cell types (Kung et al., 2003; Kung et al., 2000; Tran et al., 2007).

MicroRNAs (miRNAs) are small non-coding RNAs that regulate gene expression by targeting mRNAs for translational repression or degradation. Studies of miRNA identified selective expression of specific miRNA in specific cell types (Carissimi et al., 2009; O'Connell et al., 2010). Lentiviral vectors that expressed specific miRNA target sequence were capable of inducing either stable knockdown of the miRNA of interest or "de-targeting" transgene expression in specific cell type, depending on the expression levels of the mRNA target sequences in the transduced cells (Genter et al., 2009; Brown et al., 2007; Brown et al., 2007). Direct injection of the miR-142-regulated lentiviral vector that expressed a model GFP Ag in non-APC induced GFP-specific regulatory T cells, and promoted immunologic tolerance in mice (Annoni et al., 2009). Future identifications of miRNAs that are either absent in DC or play a regulatory role in defining specific DC function allows development of novel lentiviral vectors that target these miRNA in DC-based immunotherapy.

Recent studies revealed that crosstalk between DC and non-T lymphocytes (such as NK and NKT cells) played an important role in the regulation and induction of optimal immune response. Vaccination with mature DC transfected with mRNA encoding for TAA and the pro-inflammatory cytokines interleukin (IL)-12 and IL-18 induced optimal anti-tumor immune responses mediated by both increased NK and TAA-specific cytotoxic T cell activities (Bontkes et al., 2005). Similarly, loading TAA genetic modified DC with invariant natural killer T (NKT) cell activating factor, alpha-galactosylceramide, displayed synergic effects of TAA-specific cytotoxic T lymphocytes and NKT cells against metastatic melanoma (Fukushima et al., 2009). Genetic modifications of DC that enhance interaction/activation of these non-T lymphocytes may prove useful in further improving the efficacy of such DC-based immunotherapy.

In vivo administration of VSV-G pseudotyped lentiviral vectors activated splenic plasmacytoid DC to produce a robust IFNαβ response (Brown et al., 2007), suggesting lentiviral vector preparations can be immunogenic (Pichlmair et al., 2007). In ex vivo DC transductions, however, there are contrasting reports on the effects of lentiviral vectors on DC activation. Chen et al. (2004) reported lentiviral vector transduced human monocyte-derived DC displayed lower level of CD80, CD86, ICAM-1 and DC-SIGN, and a diminished capacity to induce Th1 differentiation in vitro. Gruber et al. (2000) reported that transduction of human monocyte-derived DC did not alter their viability, phenotype, maturation and capacity to stimulate T cell proliferation (Gruber et al., 2000). Veron et al demonstrated that lentiviral vector transduction of CD34+ progenitor-derived pDC did not induce IFNα production when compared to the non-transduced pDC cells (Veron et al., 2009). Breckpot et al. (2010) demonstrated that activation of mouse DC by lentiviral vectors was dependent on cell entry and reverse transcription. Moreover, such activation is dependent on TLR3 and TLR7-mediated TLR signaling (Breckpot et al., 2010). It is possible that differences in the lentiviral vector preparations, doses of the vector used in DC transduction, DC subsets, as well as the differentiation or maturation status of the DC used in the transduction will determine the extent of lentiviral vector-induced activation in the transduced DC. A good understanding of the magnitude of such lentiviral vector-induced DC activation in a specific treatment module is important in the optimal uses of these lentiviral vector-transduced DC in immunotherapy.

Advances in the novel design of the lentiviral vectors, envelope proteins for pseudotyping, and in vivo administrations of these vectors will continue to open up new opportunities and applications of the genetic engineering of DC in immunotherapy.

In summary, DC are professional antigen presenting cells (APC) that initiate and regulate immune responses. Molecules such as Ag, costimulatory molecules or cytokines can be expressed and manipulated (in the forms of DNA, RNA, siRNA or shRNA) directly in the DC to mediate specific modifications. Different strategies have been developed to modify DC ex vivo for manipulations of Ag-specific immunity in vivo. Replication-incompetent HIV-1 based lentiviral vectors are capable of stable transduction of both dividing and relatively quiescent cells. Safety features that safeguard the use of lentiviral vectors in gene therapy in vivo are built into the vector production system. Long-term, stable transduction of human monocyte-derived DC, human CD34$^+$-derived DC, and mouse bone marrow derived DC have been reported.

DCs transduced with the lentiviral vector that expressed tumor associated antigen (TAA) or viral Ag have been shown to effectively process and present these Ag, and induced Ag-specific T cell responses. Strategies that aim at further stimulating innate immunity to produce inflammatory cytokines for T cell activations may augment the therapeutic efficacy of the TAA-transduced DC in the treatment of cancer. It is also possible to enhance antigen presentation ability of DC by prolonging their life span via gene silencing of the mitogen-inducible nuclear orphan receptor (MINOR) whose expression leads to apoptosis, or augmenting co-stimulatory signals on DC using lentiviral vectors to over-express costimulatory molecules such as CD40L or gp34/OX40L. The plasticity of DC functions supports the development of DC-based immunotherapy that suppresses Ag-specific immune responses in autoimmune diseases, allergy or transplantation tolerance. Moreover, the ability to expand a specific T cell subset (such as Treg, Th1, Th2 or Th17) with defined functional property in vitro will facilitate greatly the uses of these cells in clinical applications in vivo.

Quantitative surface expression of key molecule (such as CD40) can be genetically defined by the use of shRNA sequences that target different regions of CD40 mRNA and of different gene silencing potency. Expression levels of CD40 on DC are pivotal in determining the different functional properties of DC to tolerize, activate or polarize antigen-specific Th1/Th2 immune responses in vivo.

In applications that do not require a long-lived stable gene expression in dividing cells, non-integrated lentiviral vectors may provide a safer alternative to the current lentiviral-based therapies in driving the expression of the therapeutic gene. Integrase defective lentiviral vectors were effective in the transduction of human monocyte-derived DC and mouse BMDC, and the induction of anti-viral immunity.

Two major strategies have been developed to target specific genetic modification of DC. Transcriptional targeting of DC can be achieved by the incorporation of a DC-specific promoter (e.g., HLA-DRalpha, CD11c, DC-STAMP promoters) in the lentiviral vectors. Novel designs of DC-specific viral envelope proteins used in the pseudotyping of lentiviral vectors.

Replication-incompetent HIV-1 based lentiviral vectors emerge as an exciting candidate gene therapy vector for hematopoietic progenitor cells and DC. A better understanding of the basic mechanisms underlying DC functional abilities to regulate initiation and activation of the immune system allows development of selective therapeutic approaches that turn on or off specific and appropriate immune responses without interfering with the remaining human immune capacity. Identification of miRNAs that are either absent in DC or play a regulatory role in defining specific DC function allows development of novel lentiviral vectors that target these miRNA in DC-based immunotherapy. Genetic modifications of DC that enhance interaction/activation of these non-T lymphocytes may prove useful in further improving the efficacy of such DC-based immunotherapy. Advances in the novel design of the lentiviral vectors, envelope proteins for pseudotyping, and in vivo administrations of these vectors will continue to open up new opportunities and applications of the genetic engineering of DC in immunotherapy of a large number of immune and inflammatory disorders (e.g., AIDS, cancers, allergy, autoimmune diseases, and graft rejections in transplantation)

Example III

Exemplary sequences useful for the co-stimulatory sequences in lentiviruses of the invention are provided below.
NM_000074
*Homo sapiens* CD40 ligand (CD40LG), mRNA.

1 actttgacag tcttctcatg ctgcctctgc caccttctct gccagaagat accatttcaa 61 ctttaacaca gcatgatcga aacatacaac caaacttctc cccgatctgc ggccactgga 121 ctgcccatca gcatgaaaat ttttatgtat ttacttactg tttttcttat caccagatg 181 attgggtcag cacttttgc tgtgtatctt catagaaggt tggacaagat agaagatgaa 241 aggaatcttc atgaagattt tgtattcatg aaaacgatac agagatgcaa cacaggagaa 301 agatccttat ccttactgaa ctgtgaggag attaaaagcc agtttgaagg ctttgtgaag 361 gatataatgt taaacaaaga ggagacgaag aaagaaaaca gctttgaaat gcaaaaaggt 421 gatcagaatc ctcaaattgc ggcacatgtc ataagtgagg ccagcagtaa aacaacatct 481 gtgttacagt gggctgaaaa aggatactac accatgagca caaacttggt aacctggaa 541 aatgggaaac agctgaccgt taaaagacaa ggactctatt atatctatgc ccaagtcacc 601 ttctgttcca atcgggaagc ttcgagtcaa gctccattta tagccagcct ctgcctaaag 661 tcccccggta gattcgagag aatcttactc agagctgcaa ataccca cag ttccgccaaa 721 ccttgcgggc aacaatccat tcacttggga ggagtatttg aattgcaacc aggtgcttcg 781 gtgtttgtca atgtgactga tccaagccaa gtgagccatg gcactggctt cacgtcctt 841 ggcttactca aactctgaac agtgtcacct tgcaggctgt ggtggagctg acgctgggag 901 tcttcataat acagcacagc ggttaagccc acccctgtt aactgcctat ttataaccct 961 aggatcctcc ttatggagaa ctatttatta tacactccaa ggcatgtaga actgtaataa 1021 gtgaattaca ggtcacatga aaccaaaacg ggccctgctc cataagagct tatatatctg 1081 aagcagcaac cccactgatg cagacatcca gagagtcca tgaaaagaca aggccattat 1141 gcacaggttg aattctgagt aaacagcaga taacttgcca agttcagtt tgtttctttg 1201 cgtgcagtgt cttccatgg ataatgcatt tgatttatca gtgaagatgc agaagggaaa 1261 tggggagcct cagctcacat tcagttatgg ttgactctgg gttcctatgg ccttgttgga 1321 ggggccagg ctctagaacg tctaacacag tggagaaccg aaaccccccc cccccccg 1381 ccaccctctc ggacagttat tcattctctt tcaatctctc tctctccatc tctctctttc 1441 agtctctctc tctcaacctc tttcttccaa tctctctttc tcaatctctc tgtttccctt 1501 tgtcagtctc ttccctcccc cagtctctct tctcaatccc cctttctaac acacacacac 1561 acacacacac acacacacac acacacacac acacacacac agagtcaggc cgttgctagt 1621 cagttctctt ctttccaccc tgtccctatc tctaccacta tagatgaggg tgaggagtag 1681 ggagtgcagc cctgagcctg cccactcctc attacgaaat gactgtattt aaaggaaatc 1741 tattgtatct acctgcagtc tccattgttt ccagagtgaa cttgtaatta tcttgttatt 1801 tatttttga ataataaaga cctcttaaca ttaa (SEQ ID NO:12)

NM_005191

*Homo sapiens* CD80 molecule (CD80), mRNA.

1 gacaagtact gagtgaactc aaaccctctg taaagtaaca gaagttagaa ggggaaatgt 61 cgcctctctg aagattaccc aaagaaaaag tgatttgtca ttgctttata gactgtaaga 121 agagaacatc tcagaagtgg agtcttaccc tgaaatcaaa ggatttaaag aaaaagtgga 181 attttcttc agcaagctgt gaaactaaat ccacaacctt ggagaccca ggaacaccct 241 ccaatctctg tgtgttttgt aaacatcact ggagggtctt ctacgtgagc aattggattg 301 tcatcagccc tgcctgtttt gcacctggga agtgccctgg tcttacttgg gtccaaattg 361 ttggctttca cttttgaccc taagcatctg aagccatggg ccacacacgg aggcagggaa 421 catccaccatc caagtgtcca tacctcaatt tctttcagct cttggtgctg gctggtcttt 481 ctcacttctg ttcaggtgtt atccacgtga ccaaggaagt gaaagaagtg gcaacgctgt 541 cctgtggtca caatgttct gttgaagagc tggcacaaac tcgcatctac tggcaaaagg 601 agaagaaaat ggtgctgact atgatgtctg gggacatgaa tatatgcccc gagtacaaga 661 accggaccat ctttgatatc actaataacc tctccattgt gatcctggct ctgcgcccat 721 ctgacgaggg cacatacgag tgtgttgttc tgaagtatga aaagacgct ttcaagcggg 781 aacacctggc tgaagtacg ttatcagtca aagctgactt ccctacacct agtatatctg 841 actttgaaat tccaacttct aatattagaa ggataatttg ctcaacctct ggaggttttc 901 cagagcctca cctctcctgg ttggaaaatg gagaagaatt aaatgccatc aacacaacag 961 tttcccaaga tcctgaaact gagctctatg ctgttagcag caaactggat ttcaatatga 1021 caaccaacca cagcttcatg tgtctcatca agtatggaca tttaagagtg aatcagacct 1081 tcaactggaa tacaaccaag caagagcatt ttcctgataa cctgctccca tcctgggcca 1141 ttaccttaat ctcagtaaat ggaattttgt tgatatgctg cctgacctac tgctttgccc 1201 caagatgcag agagagaagg aggaatgaga gattgagaag ggaaagtgta cgccctgtat 1261 aacagtgtcc gcagaagcaa ggggctgaaa agatctgaag gtcccacctc catttgcaat 1321 tgacctcttc tgggaacttc tcagatgga caagattacc ccactgcc ctttacgtat 1381 ctgctcttag gtgcttcttc acttcagttg ctttgcagga agtgtctaga ggaatatggt 1441 gggcacagaa gtagctctgg tgaccttgat caaggtgttt tgaaatgcag aattcttgag 1501 ttctggaagg gactttagag aataccagtg ttattaatga caaaggcact gaggcccagg 1561 gaggtgaccc gaattataaa ggccagcgcc agaacccaga tttcctaact ctggtgctct 1621 ttccctttat cagtttgact gtggcctgtt aactggtata tacatatata tgtcaggcaa 1681 agtgctgctg gaagtagaat ttgtccaata acaggtcaac ttcagagact atctgatttc 1741 ctaatgtcag agtagaagat tttatgctgc tgtttacaaa agcccaatgt aatgcatagg 1801 aagtatggca tgaacatctt taggagacta atggaaatat tattggtgtt tacccagtat 1861 tccatttttt tcattgtgtt ctctattgct gctctctcac tcccccatga ggtacagcag 1921 aaaggagaac tatccaaaac taatttcctc tgacatgtaa gacgaatgat ttaggtacgt 1981 caaagcagta gtcaaggagg aaagggatag tccaaagact taactggttc atattggact 2041 gataatctct ttaaatggct ttatgctagt ttgacctcat ttgtaaaata tttatgagaa 2101 agttctcatt taaaatgaga tcgttgttta cagtgtatgt actaagcagt aagctatctt 2161 caaatgtcta aggtagtaac tttccatagg gcctccttag atcccctaaga tggcttttc 2221 tccttggtat ttctgggtct ttctgacatc agcagagaac tggaaagaca tagccaactg 2281 ctgttcatgt tactcatgac tcctttctct aaaactgcct tccacaattc actagaccag 2341 aagtggacgc aacttaagct gggataatca cattatcatc tgaaaatctg gagttgaaca 2401 gcaaagaag acaacatttc tcaaatgcac atctcatggc agctaagcca catggctggg 2461 atttaaagcc tttagagcca gcccatggct ttagctacct cactatgctg cttcacaaac 2521 cttgctcctg tgtaaaacta tattctcagt gtagggcaga gaggtctaac accaacataa 2581 ggtactagca gtgtttcccg tattgacagg aatacttaac tcaataattc ttttctttc 2641 catttagtaa cagttgtgat gactatgttt ctattctaag taattcctgt attctacagc 2701 agatactttg tcagcaatac taagggaaga aacaaagttg aaccgtttct ttaataa (SEQ ID NO:13)

NM_001252

*Homo sapiens* CD70 molecule (CD70), mRNA 1 ccagagaggg gcaggctggt cccctgacag gttgaagcaa gtagacgccc aggagccccg 61 ggaggggct gcagtttcct tccttccttc tcggcagcgc tccgcgcccc catcgcccct 121 cctgcgctag cggaggtgat cgccgcggcg atgccggagg agggttcggg ctgctcggtg 181 cggcgcaggc cctatgggtg cgtcctgcgg gctgctttgg tcccatggt cgcgggcttg 241 gtgatctgcc tcgtggtgtg catccagcgc ttcgcacagg ctcagcagca gctgccgctc 301 gagtcacttg ggtgggacgt agctgagctg cagctgaatc acacagacc tcagcaggac 361 cccaggctat actggcaggg gggccagca ctgggccgct ccttcctgca tggaccagag 421 ctgacaagg gcagctacg tatccatcgt gatggcatct acatggtaca tccaggtg 481 acgctggcca tctgctccta cacgacggcc tccaggcacc accccaccac cctggccgtg 541 ggaatctgct ctcccgcctc ccgtagcatc agcctgctgc gtctcagctt ccaccaaggt 601 tgtaccattg cctcccagcg cctgacgccc tgggcccgag ggacacact ctgcaccaac 661 ctcactggga cacttttgcc ttcccgaaac actgatgaga ccttctttgg agtgcagtgg
721 gtgcgccct gaccactgct gctgattagg gtttttaaa tttattta tttatttaa
781 gttcaagaga aaaagtgtac acacaggggc cacccggggt tggggtggga gtgtggtggg
841 gcgtagtggt ggcaggacaa gagaaggcat tgagcttttt ctttcatttt cctattaaaa
901 aatacaaaaa tca (SEQ ID NO:14)

NG_012083
*Homo sapiens* intercellular adhesion molecule 1 (ICAM1),

| | | |
|---|---|---|
| gene | 5001 ... 20775 | |
| | /gene = "ICAM1" | |
| | /gene_synonym = "BB2; CD54; P3.58" | |
| | /note = "intercellular adhesion molecule 1" | |
| | / | |
| mRNA | join (5001 ... 5386, 8925 ... 9188, 17641 ... 17946, 18193 ... 18480, 18563 ... 18817, 18943 ... 19188, 19275 ... 20775) | |
| exon | 5001 ... 5386 | |
| CDS | join (5320 ... 5386, 8925 ... 9188, 17641 ... 17946, 18193 ... 18480, 18563 ... 18817, 18943 ... 19188, 19275 ... 19447) | |
| exon | 8925 ... 9188 | |
| exon | 17641 ... 17946 | |
| STS | 17695 ... 18437 | |
| exon | 18193 ... 18480 | |
| STS | 18348 ... 18667 | |
| exon | 18563 ... 18817 | |
| exon | 18943 ... 19188 | |
| STS | 19058 ... 19738 | |
| exon | 19275 ... 20775 | |
| STS | 19458 ... 19682 | |
| STS | 19672 ... 20386 | |
| STS | 19727 ... 19866 | |
| STS | 20472 ... 20606 | |
| gene | 21134 ... 22682 | |
| | gene = "ICAM4" | |
| mRNA | join (21134 ... 21566, 21696 ... 22682) | |
| | gene = "ICAM4" | |
| mRNA | join (21134 ... 21566, 21696 ... 21998, 22146 ... 22682) | |
| | gene = "ICAM4" | |
| mRNA | join (21134 ... 21566, 21773 ... 21998, 22146 ... 22682) | |
| | gene = "ICAM4" | |
| CDS | join (21173 ... 21566, 21773 ... 21998, 22146 ... 22344) | |
| | gene = "ICAM4" | |
| CDS | join (21173 ... 21566, 21696 ... 21998, 22146 ... 22264) | |
| | gene = "ICAM4" | |
| CDS | join (21173 ... 21566, 21696 ... 22015) | |
| | gene = "ICAM4" | |
| STS | 21874 ... 22676 | |
| STS | 22013 ... 22262 | |
| STS | 22047 ... 22240 | |
| STS | 22073 ... 22282 | |

Origin
1 attttatctg ctcgtccagc atggtcagcc ctccactttt taaattttat tttatttatt
61 tttttgagac agagtctcac tctgttgtcc aggttggagt ccagtggcgt gattcggct
121 cactgcaacc tctacttccc aggttcgagc aattctcctg cctcagcttc ccgagtagct
181 gggattacag gcccgcgtcc cacacctag ctaattttg tattttagt agagacaggg
241 ttcaccatg ttggccaggc tggtctcgaa ctcctgacct caggtgattc tcctgccttg
301 gcctcccaaa gtgctgagat tacaggtgtg agccactgca cacggc-ctta aatttattt
361 attatttatt tatttattta tttagagact tagtctcact ctgttgccca ggctggagtg
421 cagtggcatg gtctcggctc actgcactcc acctcctggg ttcacgccat tctcctgcct
481 cagcctcccg agtagctggg actacaggcg cccaccacca ctcccggcta atttttgtat
541 ttttagtaga tatgggggttt cactgtgtta gccaggatag tctcgatctc ctgacctcgt
601 gatccgcctg cctcggcctc ccaaagtgct gggattactt attttgttt ttgtagagac
661 aggttctcac tgtgttgccc aggctggtct tgaactcctg atctcaagtg atcttcccac
721 ctcagtctct caaagggctg ggattacagg ggtgagccac tgcac-cccac cttccctcta
781 cttttttacg gtttccttct gctatgaatg tgcatgtcca gttgtctgct tcttagaact
841 gatatttacc ttcctcatcc atcagccatt ggaggaggac tgggaccgct cagattattg
901 atctgaccca ttctttcggc aggtttcct ggtggctgtc ttccatcacc aaaactggaa
961 tcagaagagt ttccatagcc cttttttttt ccccacatct ttgctgaagc agagttttga
1021 aaaacaaaac cacaaactaa gctattcccc agaagaaatc tgtaat-caaa gataagctct
1081 gccgggcaca gtggctcacg ccttttggag gccaaggcgg gcg-gatcacc tgaggtcagg
1141 agttctagac ctgccaggcc aacatggtaa aacctcatct ctac-taaaaa tacaaaaatt
1201 agctagatgt ggtggtgggt acctgtagtc tcagctacct gggag-gctga ggcaagagaa
1261 tcgcttgaac ctgggaagta gaggttgcag tgagccgaga ttgcac-cact gcactccagc
1321 ctgggcgacg gagtgagacg acctcacaaa aatttacata aataaaatga aaagtaaaat
1381 aaaaatacaa aagttggccg ggtgcgtttg ctcacgcctg taatc-ccagc actttgggag
1441 ggtgaggcag gcagataatg aggtaagaag atcgagacca tcctg-gctaa cacggtgaaa
1501 cccctgtctct actaaaaata caaaaaatta gctgtgcgtg gtga-cacgca cctgtagtcc
1561 cagctatttg ggaggctgag gcaggagaat cacttgaacc tgggag-gtgg aggttgcagt
1621 gagccgagat cgcaccactg cactccagcc tgggccacag agt-gagactc catcttgaaa
1681 aaaaaaaaaa atacaaaagt tagccagggg tgttggtggg tgcct-gtaat cccagctatt
1741 tgggaggcta aggcagaaga atttcttgaa cctaggaaac ggag-gttgca gtgagccgag
1801 atcacacctc tgtactccag cctggacaac agagcgagac tttgtct-caa aaaaaaaaa
1861 aaaaaaaaaa ctaaataggc cgggagcagt ggctcatgcc tataatccca gcccttttggg
1921 aggccaaggc aggtggatca cttgaggtca ggagtttgag accag-gctgg ccaacatggt
1981 gtaacccgt ctctactaaa aacacaaaaa ttagccgggt ctggt-gcgt atgtctgtaa
2041 tcccagctac tcgggaggct gaggcaggag aatcacttaa acctgg-gagg caggggttgc
2101 agtgagctga gatcgtgcca ctgcactcta gccaggtga cagt-gaaa ctctgtctca
2161 aaaaattaaa aagaaattc agcaagtaat gagttaagga attc-gaatat taaggcgagt
2221 gacaaggaac gcccaggatg tggcccagga tggagtaggg gggacactca tttaggagaa
2281 agctcaggcc acaagacagg aggagccagc cttgttgggg ttgaagggaa gagcattcca
2341 ggctgaggga actgcaaggc gtttgcatgg gacactatgg gatg-gcttct gcccttggtg 2401 ggcagcctct ggtctgaggc cattctttgg cctgcctgac tgtctggcaa ccgggaggaa 2461 gccctgccct tcctggagac agaaacaaag gtctaggaaa tatctgcttc ccttttcctt 2521 gaaaaacgct taagggaacg gaggactggg aggtgccgtc tctctctgcc agcctgcccc 2581 ctaccatagc catcccactc ccatctcaga aagtgacccg ccatcctcca aaaggctcgg 2641 accctgatca aggagtcatc ccccttgtcc cagcacctcc agttggccca gcctccaaaa 2701 cggatgtcaa attcagccct ttctccaagg acactgccca gtccaggccc cactatcatt 2761 catctggact agaacagtca cctcctctcc catctcctgg ctgcagctct tgaagcctca 2821 actgggcccc tgtgaacact tgagttaggg caaggtcctt cctctgctca gaaccctcta 2881 tacctcccac ctcgctgggc ataaaagcca aagtcctggc cagcacggt ggctcacatc 2941 tgttatccca gcactttggg aggccaaggg gggcggatca ctagagtca ggagttagag 3001 accaacatgg tgaaacccca tctctactaa aaatacaaaa attagctagg cgtggtgacg 3061 caccoctgta gtaccagcta ctcggtaggc tgaggtggga gaatcgcttg aacctgggag 3121 gcagagtttg cagtgagccg agatcacacc actgtgctcc agcctgggtg acagaacgag 3181 actgggttc agaaacaaac aaacaaaaca acaaagtcct cctcagtga caggaacttg 3241 cacctatctg ccctgtcatc tccctgcccg ctcctctcct cgaatctctc ctttgctaag 3301 cctgctccag ccacactgtt ctcctggctg ttccttttt tttttttttt tttttttttt 3361 tgagtctcac tctcacccag gctggagtgc agtgcctcta tcttgctca ctgcaacctc 3421 cgcctgccgg gttcaagaga ttctcctgca tcagcctccc aagtaggtgg aattacaggt 3481 gtgcaccacc acacccggct aattttgta ttttgcatag agatgggggt ctccctatgt 3541 tgcccaggct ggtcttgaac tcctgggctc aagtgatcct cccatctcgg cctcccaaaa 3601 tgctgggatt acaggtggga gccgcgccca ggtggatttt tgtctgactc tgttcattcc 3661 tgtgtcccca gtacctgaa ggacgccaag cacacagtag gcgcttaaaa aacattgagc 3721 cacatgttga gaaaagaacg gcaccattgt ggctgcaagt gggacttggg ccgcgcgggg 3781 gagctcgcgc acctcgggcc ggggcaagag ctcagtggaa cccgcccgag gaagaacccg 3841 tggcgcagga ttttcccagg ccttctgagg accaggggcg tccccgtcc cacccgtga 3901 ctttgctcag gccgttccgg ggcgggaatt cagaactcct cagccccca agaaaaaaat 3961 atcccgtgg aaattccttg ggaatgaccg aggcggggga aatatgcgtc tctggatggc 4021 cagtgactcg cagcccccttc ccccgataggg aagggcctgc gcgtccgggg acccttcgct 4081 tcccccttctg ctgcgcgacc tccctggccc ctcgagatc tccatggcga cgccgcgcgc 4141 gccccacaac aggaaagcct taggcggcgc ggcttggtgc tcggagactt aagagtaccc 4201 agcctcgacg tggtggatgt cgagtcttgg ggtcacacgc acagcggtg gccaagcaaa 4261 cacccgctca tatttagtgc atgagcctgg gttcgagttg ccggagcctc gcgcgtaggg 4321 caggggttcg agcgccctt ctccctgcct cgcctctgcg cctggggct gctgcctcag 4381 tttcccagcg acaggcaggg atttcgagcg tcccccctccc ctccctcgtc aagatccaag 4441 ctagctgcct cagttcccc gcggagcctg ggacgccagc ggaggggctc ggcgcgtagg 4501 gatcacgcag cttccttcct ttttctggga gctgtaaaga cgcctccgcg gccaaggccg 4561 aaagggggaag cgaggaggcc gccggggtga gtgccctcgg gtgtagagag aggacgccga 4621 tttccccgga cgtggtgaga ccgcgcttcg tcactcccac ggttagcggt cgccgggagg 4681 tgcctggctc tgctctggcc gcttctcgag aaatgcccgt gtcagctagg tgtggacgtg 4741 acctaggggg aggggcatcc ctcagtggag ggagcccggg gaggattcct gggcccccac 4801 ccaggcaggg ggctcatcca ctcgattaaa gaggcctgcg taagctggag agggaggact 4861 tgagttcgga ccccctcgca gcctggagtc tcagtttacc gctttgtgaa atggacacaa 4921 taacagtctc cactctccgg ggaagttggc agtatttaaa agtacttaat aaaccgctta 4981 gcgcggtgta gaccgtgatt caagcttagc ctggccggga aacggaggc gtggaggccg 5041 ggagcagccc ccggggtcat cgccctgcca ccgccgcccg attgctttag cttggaaatt 5101 ccggagctga agcggccagc gagggaggat gaccctctcg gcccgggcac cctgtcagtc 5161 cggaaataac tgcagcattt gttccggagg ggaaggcgcg aggtttccgg gaaagcagca 5221 ccgcccttg gcccccaggt ggctagcgct ataaaggatc acgcgcccca gtcgacgctg 5281 agctcctctg ctactcagag ttgcaacctc agcctcgcta tggctcccag cagccccgg 5341 cccgcgctgc ccgcactcct ggtcctgctc ggggctctgt tccagtgta gtcggggtgg 5401 ggattgccgt cgggccagtt ctccgaagcc ccgggaggac cggctcccgg gtcaggtcat 5461 gcatgcttag gtagctgttt atgggaagga ggggctagag acagcgattg aaaggcaaca 5521 gccagtaggt tcgaatccag accctgcata cctccacgtg tggccttggg ctatagattg 5581 cagctttaaa aaagggtagg gggttggaga tggaggggag gggcgggcct cgttttgttg 5641 cccaggccgg tcttgaactc cggggtcta gccttacctc ctgcctcagc cgccgagta 5701 gctgggatga gaggtgtgaa ccaccgcctt gcttggctag attgcgtctc ttacagtttc 5761 tcagctgtaa aacgggaaac gttatagcgg ccacctggca gggtatcttg gcccagcgca 5821 gcacctggcc ccaggactcg atcatgatgg tttgggaact tggctctgtg ccaacccaac 5881 aaggcttaag ggaccccac ccccctcaag atgtatattc tgttcctcat cctctctgcc 5941 cctggggaag tccagggctg cttctacttg ggggaattcc agagctgact tatccgtggc 6001 ccaaagctga gaagtgggac gccccagcac accctccccc agctccagcc cagctaggga 6061 agagggaagg ggtcagaggg tctttcatgg tggtgtaagt ttgggggaacc aggagggtgg 6121 gagattgaca gcttggttaa cagctcaaca aagcctgaga tccaggccag cacggtagtt 6181 catgccagta atcccaacac tttaggagcc ccaggcgggc gaatcactta aggtcaggag 6241 tttgagacca gcctggccaa catggcaaca tcccgtctct actaaaaata caaaaattag 6301 ctggcatggt ggtgggcgcc tgtgatccca gctgctcggg aggctgaggg aggaaaatcc 6361 cttaagccca cgaggctgag gttgcagtga accaagattg tgccact-
gca ctccagcctg
6421 ggagacatag cgagattctg tctcaaaaaa caaagcgttc tgatccg-
gac tcagacccag
6481 atcgcactgc tttctagctg agtaaccatt tctctctatg aaatgggaat
ggtcccagaa
6541 tctcccttgg agaatgtatg gagccagtgt cctcacaccc ccatc-
caaga tagaacaaat
6601 ctgagacagg aatctttgag tgaggcagtg ctgggctcag
acattttttc ccaccttcgg
6661 aggcagcaga atctgaggga cctgatccaa ataagcccct
tctttctttc ttttcttttc
6721 tttttttttt ttttttttttt ttgagacgga gtctcactct gtcgcccagg ctg-
gagtgca
6781 gtggcgtgat ctcggctcac tgcaacctct gcctcccagg ttcaaac-
gat tctcctgcct
6841 cagcctccct gagtagctgg gactacaggc atgtgccatc acac-
ccggct aatcactgtg
6901 ttagccagga tggtctcgat ttcctgacct catgatctgc ccaccct-
gcc tcccaaagtg
6961 ctgggattac atgcgtgagc cacagtgccc accccgtaag cccct-
tcttt cttacctgca
7021 aggtagccag ttgctaccca tcctgtgctg agttacttgt attag-
caagg gatggggtgg
7081 ctatactcac ccacttaca gatgggaaa ttgaggccca
aagaggggga aactacgtgt
7141 ctcagggagt gaggagccag tctgattcct ggagggctga
ctgtctccac ctgacttctt
7201 aggagggagg agggcaccaa cttcacatta aaatctggtt ggaca-
cagtg gctcacacct
7261 gtaatcctgg cattttggga ggcttaggcg ggaggatcac ttgaggc-
cag gagtttgaga
7321 ccagccttag caacatagtg agaccccatc tctacaaaaa
tgttttttcag ggccaggcgc
7381 ggtggctcac acctataatc ccagcactt gggaggctga
ggcgggcgga ttacctgagg
7441 tcaggagttt gagaccagcc tgaccaacat ggagaaaccc cgtctc-
tact aaaaagtacaa
7501 aattacccgg gcgtggtggc gcatgcctgt aatcccagct actcgg-
gagg ctgaggcagg
7561 agaatcgctt gaacctggga ggcggaggtt gcggtgaact
gagatcgtgc cattgcactc
7621 cagcctgggc aacaagagct aaactccgtc tcaaaaaaaa aaaaat-
gttt ttcaaatatt
7681 agccgggtat ggtggtgtcc tgtagtccca gctacttggg aggct-
gagat gggaggatca
7741 cttgagccca ggagttcaag gttacagtga gctatgattg tgccact-
gta ttccagcctg
7801 ggtaacagag ggagacccgt ttaaaaaaaa aaaagtgatg
gctaaagtcc ttccatggct
7861 ccctattgcc ctcagtataa agaacacatg tggctgggcg tggtggt-
tca cgcctgtaat
7921 cccagcactt tgggaggctg aggcgggcgg atcacttgag gccag-
gagtt tgagagcagg
7981 ctggccgacg tggcgaaacc ccgtctctat aaaaataca aaaatt-
agct gggcgtggtg
8041 gtgcttgcct gtaatcccag atactctgga ggctgaggca ggagaat-
cac ttgaacccgg
8101 gaggcaaagg ttgcagtgag ctgagattgc gccactgcac
tccagtctga gtgacaaagc
8161 gagactccat ctcaaaaaaa aaaaaaataa aagaacacat ctttag-
catg gccttcagtg
8221 ctcacgggat cttcctgaat taatctcccc ctcttcatcc ttgctcactc
agctccagcc
8281 accctgcccc gggacatctg tacttgcctg gaacttattt ccctttttctc
cggacagcca 8341 gcccttctc gtcatttaga tctctgctga aacattaccc tgtcaccaaa
gcactgtcta
8401 ttctatcacc ctgttttgtt tttgtcaaag ctcatattaa catcagttat
taattatctt
8461 gtttgctcat aattttttt tttttttt tggagacaga gtctcgttct
gttgctcagg
8521 ctggagtgca gtggcacaat cttggctcac tgtaacctcc acctc-
ccagg ttcaagtgat
8581 tcttgtgcct cagcctccca aatagctagg actacaggca cgtc-
ccacca tgcccagcta
8641 attttttgtat ttttagtgga gacggggctt tgtcatgttg gccaggctga
tctcaaattc
8701 ctgacctcaa gtgatctgcc cgccttggcc tcccaaagtg ctgggat-
tac aggcgtgagc
8761 caccacaccc ggcctgctca tgaattttct ctttaacttc cacatcgaag
gcaaagtatt
8821 gtcttgttaa ggctgtgcct ccagcaccca gcacaggctg ggcgca-
catt cccttgatga
8881 acctgatttg taatgcctgt cgcctcttcc ctcgtttctt ctaggacctg
gcaatgccca
8941 gacatctgtg tccccctcaa aagtcatcct gccccggggga ggctc-
cgtgc tggtgacatg
9001 cagcacctcc tgtgaccagc ccaagttgtt gggcatagag
accccgttgc ctaaaaagga
9061 gttgctcctg cctgggaaca accggaaggt gtatgaactg agcaat-
gtgc aagaagatag
9121 ccaaccaatg tgctattcaa actgccctga tgggcagtca
acagctaaaa ccttcctcac
9181 cgtgtactgt gagtaactga gcccggaggg ctggactagg cagac-
ccggt gggagagacg
9241 tgcagggggca cctgcagagg cctgggggaa tctttgccac
ttgctcgtag ggtcaaggag
9301 gggctccttg cagggcaggt ggggacatcc ttggaaagtc cctttgt-
gaa tttctttggg
9361 tacaattaaa gtatttacag gctgggtgcg gtggctcatg cctg-
taatcc cagcactttg
9421 agaggctgag gctggcggat cacctgagat caggagttta
agtttcgcca acatggcgaa
9481 accctgtctc tgctgaaaat acaaaaatca gccgggcatg gtgt-
caagcg cctgtaatcc
9541 cagctacttg gaaggctgag gcaggagaac gcttgaacct gagag-
gcaga gattgcagtg
9601 agccgcgatc gtgccagtgc actccagtct ggataacaga gcaa-
gattcc atctcaagaa
9661 aaaaaaaatg ccatctctct atgcctcact ctttgaacat atgacacggt
cctgcttcag
9721 acactttaat aaaagatgca aattaagcca agtgtggtgg cttgtac-
cta taatcccaac
9781 tactccagag gctgaggcag aaggatggtt tgagcccagg
agtttgagac cagcctgggc
9841 aacagagtga gaccctgttt ctttcttttt tttttttttt ttttgagac
ggagtctcac
9901 tctgtcgccc aggctggagt gcagtggtgt gatctcggct cactg-
caagc tccgcctccc
9961 gggttcacgc cattctcctg cctcagcctc ccgagtagct gggacta-
cag gcgcctgcca
10021 ccatgcccgg ctcattttt tgtattttta gtagagacgg ggtttcactg
tgttagccag
10081 gatggtctca atctcctgac ctagtggtcc gcccgcctcg gcctc-
ccaaa gtgctgggat
10141 tacaggtgta agcactgtg cccatccaag accctgtttc taccg-
gaaaa aaaagtaaa
10201 taatttagct gggcatcgtg gtgtgcacct gtaatcccag ctgtc-
ctga ggctgtgatg
10261 ggaggattgc tttaacccag ggggttcgaat cctaggagtt cgaatc-
catc ctaggcaaca 10321 tagcaaaacc ccatttttat ttaaaaaaaa aaaaaaagat atgagttaaa actagccctg 10381 ggatggcatt tttcacatat tggtaacaaa caaaagaatt gatggccgggg cgcagtggct 10441 cacgcctgta atcccagcac tttgggaggc cgaggcgggc ggatcacaag gtcaggagat 10501 cgagaccatc ctggctaaca tggtgaaacc ccgtctctac taaaactaca aaaaattagc 10561 cgggcatggt ggcaggcgcc tgtggtccca gctactcagg aggctgaggc aggagaatgg 10621 catgaacccg ggaggcagag cttgcagtga gccaagatcg tgccactgca ctccagcctg 10681 ggcgacagag caagactcca tctcaaaaaa aaaaaaaaaa aaaagaattg ataacagctg 10741 tgctgccaag gctattggaa cgtaggaggt cctaggacag tgctgttggg agcataaata 10801 agcccaaccc tgtggcggga aattgggcat cagttctcaa aatgtcatgg gctgggcacg 10861 gtggctcacg cctgtaatcc cagcactttg ggaggctgag gcggat cacttgaggt 10921 caggagttcg agaccagcct gaccaccatg gagaaacccc gtctctatta aaaatacaaa 10981 aaaaactagc caggcatagt ggcacatacc tgtaatccca gctactcggg aggctgaggc 11041 aggagaatct cttgaaactg ggaggcagag gttgcggtga gctgagattg cgccactgca 11101 ctccagcttg ggcaacaaga gcaaaactcc atctcaaaaa aaaaaaaaaa agaaataaaa 11161 gaaggtatgt tgaatatgag tggtatgcca ccctcacatt agggaagggc agtttcgggg 11221 aggctgtatt tatgtataaa atagccctaa aaggaagtgg gagaaatgac aatattagct 11281 ggctatgaga agagaggctg ggaggctgtg ggagagggct tgggtgtgga gaattctttt 11341 tgttttttcc tttttttgag acagagtttc actcttgttg cccaggctgg agtgcaatgg 11401 cacgatctca gctcaccgca accttcacct cctgagttta agtgattctc cggcctcagc 11461 ctcccgacta gctgggatta caggcatggg ccactacgcc tggcaaattt tgtatttta 11521 gtagagacag ggttctcca tgttggtcag gctggtcttg aactctgacc tcaggtgatc 11581 cgcccgcctc ggcctcccaa agtgctggga ttacaacgtg agccactttg cctggctgag 11641 aattcttttt ttgttgttgt ctttttgaga tggagttttg ctgtgtcccc agcctggagt 11701 gcaatggtgt aatctcagct cactgcaacc tctccctccc gggttcaagc aattctcctg 11761 cctcagcctc ccaagtagct ggaattacag gcgcccagca ccacgcccgg ctaattttg 11821 tattttagt agagacggga tttcatcatg ttggccaggc tggtcttgat ctcctgacct 11881 tgtgatctgc ccgcctcggc ctcccaaagt gctgggatta caggcgtgag ccactgcccc 11941 cagccgagaa tttctctttg cgtccttcct actttgggga cttcgaatgg tgggaaagag 12001 ttatcaaggc caaaataagg aattcaaatg aaaacaaaac aaaatcaaag aagaaaaaac 12061 agaagagcac tgggcaggct aggcacgtgg ctcatgccta taatcccagt gatttagaag 12121 gccgaagtag aaggatcgct tggaggccag gagttggaca ccagcctggg caacatagca 12181 agacccata tctacaaaaa ataaaaaacc taaccagcg tgctgcata ctagtagtcc 12241 cagctactca ggaggctgag gtgggaggat cacctgagcc tgggaggtcc aggctgtagt 12301 gagccgtgat gacaccactg cactccagcc tgggtgacag agaaagaccc tgtctctaaa 12361 aaataaaaac tggccaagta gctttgggat tagccttggg ttccagtccc agcaaggcct 12421 ttaatagctt gggacatgac ttctgcattt actttgcaat caggtgagac ctcctctgat 12481 ggggaaaatg acacggtgag tgacaaagga tgttctccta tcattgtgtc agggcaagga 12541 agcctctggg taaatgatca aatgatcagc tttgcttctg atttggaggg tgggtgagca 12601 gatgctgacc ttcccaggtg agggaagtcc ccgaacattc ccagcagctt ctggaaaccc 12661 cagggaaacc tctttgaagg tcttttctgc atctctgcct gataggtctt ttttttttt 12721 tttttttttt tcttttttt gacacacagt cttgctctgt cgcccaggct ggatcactgc 12781 aacctccatc tcccgggttc aagcagttct cctgcctcat cctctccagt agctgggatt 12841 acaggcacct ggcaccacgc ctggctaatt tttgtatttt tagtagagac agggtttcgc 12901 caagttggcc aggctggtct cgaactctag acctctggtg atccaccgc ctcagcctcc 12961 cgaagtgctg ggattacagg cttgagccac cacgcgcggc tctgcctgat agctgagagc 13021 atagaactcc aggtttgaga cctggctctg ccacatttct ccctctatga ctgtgggtgc 13081 cccactttgc cttagttttt acctctgtga aatggagcag atggctgca caggtagcaa 13141 aggagtaaaa gttatgtggg agggtggtac ctgagagaga ctctagcttg gtcttgcccc 13201 acccctggtg taaacataaa gaagcctccc tggatggctc aatcttctcc aaaaaggtta 13261 gaggtgtaat tcctagagga ggcgaccact agctgggctt tgaaggatgt gtaggagttc 13321 ataaggacag gcattctggg caggaggaac agcctgggca aaagttggga gcagggagaa 13381 atcttgatgg aggcaggagg aggaggaggt aggttggtgt aggccaggtg cagtggctca 13441 cacctgtaat cccagtgctt tgggaggcca agcaagagg attgtttgag cccaggagtt 13501 cgagaccagc ctgggcaaca tagcgagacc ctgtctctaa gaaaaataa aaaaattagg 13561 gtacagtggc atatgcttgt attctcaact actctggagg ctcaagtggg aggatcactt 13621 gaaccagga atttttttgt tttgttttt gttttttga gatggagtct cactctgtgg 13681 cccaggctgg agtgcagtgg tgccatcttg gctcactgca gcctcctcca cctcctgggt 13741 tcaaccgatt ctgctgcctg agcctcccga gttgctggga ttaaggtgcc caccatcatg 13801 cccagctaat tttttgtat ttttagtaga tagggttt accatgttag ccaggctgg 13861 cttgaacgcc tgaccgcaag agatcctcct gcctcagttt cccaaagtgc tgggattata 13921 ggtgtgagcc actgagcctg gtcaagccca ggaatttgag gttacagtca gctatgattg 13981 caccactgca ttccagccca ggtgacagag agagacactg cccctaaaaa aaaaaaaaa 14041 attgattgat gggaggaagg gtgaggttgg cagagccttg aatgccaggt ggaggagctg 14101 ggacttcct tcttgggggtg atagggagtc atggaggggtt tctgagcagg ccaggggatta 14161 gatagctgaa ggctggattt actggaagcc aatgagcagt ggctatggt ccttgtccac 14221 gcggcccatg ttgtgggcag tgaccgtatt caagaaggga aggacagaca agtatttgaa 14281 tacttcagtg accaggattt ggtaaaggac tgcaggtcag ggtcaagaag aggtgagagc
14341 aggacagact tcctccccgc tgcaccaggc agctgagctg ggtttcctct aggggctgag
14401 gtttgagggt acctcaagtt ctgcaagagt ctataggagg tggtaagaga gaagagctgg
14461 aggtcagagt tttcttgact atatatatat ataltttttt gtttttgttt ttaacagctt
14521 aacagctttc tgttttattt ttagagacag ggtctcaggg tctcactttg tcacccaggc
14581 tggagtgcag tggtacaatc gtagctgact gcagcctcaa actcccaggc tcaagaaatc
14641 ctcctcccac ccttagcctc ctgagtagca gggactacag gtgtgagcca gcaggaagcc
14701 cagctggttt ttttttttc tttggtgttt tttgtttgtt tgtttgagac cggagtttcg
14761 ctcttattgc ccaggctgaa gtgcaatggc aggatcttag ctcaccacaa cctccgaccc
14821 ccaggatcaa gctattctct tgcctcagcc acctgagtag ctggattac aggcatgcga
14881 caccacacaa ggctaatttt gtatttttag taaagacagg gtttctcat gttggtcagg
14941 ctggtctcga actcccaacc tcagatgatc cacctgcctc ggcctccaa agtgctgaga
15001 ttacaggcat gagccaccgt gcccggcctt tttttttttt tttttttt tgagacagag
15061 tctcactctg tcgcccaggc aggagtgcag tggttcgatc tgggctcact gcaagctccg
15121 cctcccgggt tcactccatc ctcctgcctt agcctcctga gtagctggga ctacaggcgc
15181 ccaccaccac gcctggctaa ttttttgtat ttttagtaga gacggggttt caccgtgtta
15241 gccaggatgg tcttgatctc ctgacctcgt gatccgcccg ccttgcctc ccaaagtgct
15301 gggattacag gcgtgagcca ccatgtctgg cctgccagg ctgtcttga actcctgact
15361 tccggtgatc catctgttct ggcctcccaa agtgctggga ttacaggcat aagccaccac
15421 gccatgccga agcccagctt gtttttaatt tttttttttt tttttggaga aatgaggtct
15481 tgcaatgttg cccaagctag ccttgaactc ctggcctcaa atgaccccgc cttggcatcc
15541 caaagtactg gattacaga tgtgagccac catgccccag cctgcttc ttgagatacg
15601 atttagaata ccataagatt catccctttt aagcacataa ttcaatgact tctgtacaaa
15661 caaccatgac tacaatctaa tttaaaata tttcaatcac tctaaaaaag aaacctcctg
15721 cttatgtaca gcgactctgt ctacctctta agtgaattct cctaccttta atagccctat
15781 tttacagttc aggaaactga ggttcagaga gacaaagtca cttacccaca gcaaagaagc
15841 aaggctgggt atcaaatgca ggaccccccc ggtcctgatg ctttttttt tttttttt
15901 ttcctctgag agagactctc actctgtcac tcagtctaga gtacagtggc gcgatctcag
15961 ttcactgcaa tctctgcctc ctgggctgaa gtaatccttt cctcacaagt aaacctcagc
16021 ctctcaagta gctgggacta caggcacaca acaccacgcc tggctaattt ttgtattttt
16081 aggtagagac ggggtttcac tatattggcc aggctggtct tgaactcctg acctcaggtg
16141 atccgcctgc ctcggccccc caaagtgttg ggattacagg cgtgagccac cacacgcagc
16201 cttttgtta ttagactctg tcattactga ctttttttt tttttaatag aaacagggtc
16261 tttctttccc aggctaaagt acagtggcat gatcacagtt cactatagcc ttaaactcct
16321 gggctcaagt gatcctcctg cctcagcctc ccaagtagca gggactacag gtgtgcacca
16381 ccacacccag ttaaccattc attcattcat tcattcattt attttgagat ggagtctcgc
16441 tctgtcacct aggctggagt gcagtggcac gatctcagct cactgcaacc tccacctccc
16501 aggttcaaga gattctcctg cctcagcctc cgagtagct gagactacag gcgtgcacca
16561 ccatgccaga ctaattttg tattttaat agagacgggg tttcactctg ttggtcaggc
16621 ttatctcgaa ctcctgactt cgtggatcca ccctccttgg cctccaaag tgctgggatt
16681 aaaggcgtga gccaccgcgc cctgccaacc ttttttttaat tttcttaga gatggggtc
16741 tcccctatgtt gcccaggctt gtcttgaact cctggcctca agtgaccctc ttgccttggc
16801 ctcacaaagt gctaggatta cagcctgagc catcacacct ggccaacagg tttttttttt
16861 tgttttgttt tgttttttaa agaatgtcta ggccaggctc atttactttc acctgtaatc
16921 ccagcacttt gggaggccgg ggtgggcaga tcacttgagg tcaggaattc gagaccagcc
16981 tgggcaacat gctgaaaccc cgtttctact aaaaatacaa aaattagctg ggtgtggtga
17041 cacgtgcctg taatcccagc tactcaggag gttgaggcag gagaattgct tgaacccagg
17101 aggcagaggt tgcagtgagc caagatcatg ccatcaccct ccagcctggg cgacagaagg
17161 agactcagtc taaaaactta attaattaat taattaaaaa taaaaataca aaaattaacc
17221 tggtgtggtg gtgtgtgcct gtaatctaag ctactcagga ggctgaggca ggagaatccc
17281 ctgaatccca gaggcagagg ttgcagtgag ccaagatcga gccactgttt gcccagtcta
17341 gtgcactggg ctgctgaatt tatttgacca gacacctagc aatagactt gaagttcttt
17401 tccactttc actctaagat gctgctgtca tgaataagga atatttgat ccccttcaca
17461 aacactcggg gccctcttac cagttttcac tgaagatctt gacattccta tctgcttagg
17521 tgtctgggcg tgtttggggg agatactgaa gaggtagggc tcccaggcag gtgcagttcg
17581 tctgttaggc aggcagcaag gtccacttca ccagacaccc ccacctctgt tttcctgcag
17641 ggactccaga acgggtggaa ctggcacccc tcccctcttg gcagccagtg ggcaagaacc
17701 ttaccctacg ctgccaggtg gagggtgggg caccccgggc caacctcacc gtggtgctgc
17761 tccgtgggga gaaggagctg aaacgggagc cagctgtggg ggagcccgct gaggtcacga
17821 ccacggtgct ggtgaggaga gatcaccatg gagccaattt ctcgtgccgc actgaactgg
17881 acctgcggcc ccaagggctg gagctgtttg agaacacctc ggcccctac cagctccaga
17941 cctttggtga ggattgaaga agccagcagg gagaaggtgg gggtggggta tcctgcaatg
18001 cggtgcctgt ggccacagga tcttttgaga tgggtgtggc ccggctaag gggtgcatgt
18061 gttctaggcg tatgtgacct aggctgctga gtgcccctgg aagagatct cgcaggaggg
18121 ggaatgaaat gccccagaga agggcttcgg gacgtccatc cctgtctgct cacaccttc
18181 ttctctccct agtcctgcca gcgactcccc cacaacttgt cagccccgg gtcctagagg 18241 tggacacgca ggggaccgtg gtctgttccc tggacgggct gttcccagtc tcggaggccc 18301 aggtccacct ggcactgggg gaccagaggt tgaacccac agtcacctat ggcaacgact 18361 ccttctcggc caaggcctca gtcagtgtga ccgcagagga cgagggcacc cagcggctga 18421 cgtgtgcagt aatactgggg aaccagagcc aggagacact gcagacagtg accatctaca 18481 gtaagaaggg gcaggggcgg agtggggctt cttggggggtg tgacctgaac ccggggcggg 18541 gctcactgtg tgcctattcc aggctttccg gcgcccaacg tgattctgac gaagccagag 18601 gtctcagaag ggaccgaggt gacagtgaag tgtgaggccc accctagagc caaggtgacg 18661 ctgaatgggg ttccagccca gccactgggc ccgagggccc agctcctgct gaaggccacc 18721 ccagaggaca acgggcgcag cttctcctgc tctgcaaccc tggaggtggc cggccagctt 18781 atacacaaga accagacccg ggagcttcgt gtcctgtgtg agtggggctg ctggtcaatg 18841 gcccctatcc cccaaggccc aatctccctg aaggtccat aagtcttgc ctccaagtcc 18901 tgcccccacc cacctccatg tcatctcatc gtgttttcc agatggcccc cgactggacg 18961 agagggattg tccgggaaac tggacgtggc cagaaaattc ccagcagact ccaatgtgcc 19021 aggcttgggg gaacccattg cccgagctca agtgtctaaa ggatggcact ttcccactgc 19081 ccatcgggga atcagtgact gtcactcgag atcttgaggg cacctacctc tgtcgggcca 19141 ggagcactca aggggaggtc acccgcaagg tgaccgtgaa tgtgctctgt gagtgagccg 19201 gcgggcagag ctggtggggg gcaggggcca tggacctaat gcaatcctca ccgcctgttg 19261 tatcctcccc acagccccc ggtatgagat tgtcatcatc actgtggtag cagccgcagt 19321 cataatgggc actgcaggcc tcagcacgta cctctataac cgccagcgga agatcaagaa 19381 atacagacta caacaggccc aaaaagggac ccccatgaaa ccgaacacac aagccacgcc 19441 tccctgaacc tatcccggga cagggcctct tcctcggcct tcccatattg gtggcagtgg 19501 tgccacactg aacagagtgg aagacatatg ccatgcagct cacctaccg gccctgggac 19561 gccggaggac agggcattgt cctcagtcag atacaacagc atttggggcc atggtacctg 19621 cacacctaaa acactaggcc acgcatctga tctgtagtca catgactaag ccaagaggaa 19681 ggagcaagac tcaagacatg attgatggat gttaaagtct agcctgatga gaggggaagt 19741 ggtgggggag acatagcccc accatgagga catacaactg ggaaatactg aaacttgctg 19801 cctattgggt atgctgaggc cccacagact tacagaagaa gtggccctcc atagacatgt 19861 gtagcatcaa aacacaaagg cccacacttc ctgacggatg ccagcttggg cactgctgtc 19921 tactgacccc aacccttgat gatatgtatt tattcatttg ttattttacc agctatttat 19981 tgagtgtctt ttatgtaggc taaatgaaca taggtctctg gcctcacgga gctcccagtc 20041 ctaatacacat tcaaggtcac caggtacagt tgtacaggtt gtacactgca ggagagtgcc 20101 tggcaaaaag atcaatggg gctgggactt ctcattggcc aacctgcctt tccccagaag 20161 gagtgatttt tctatcggca caaagcact atatggactg gtaatggtta caggttcaga 20221 gattacccag tgaggcctta ttcctcccctt cccccaaaa ctgacaccctt tgttagccaa 20281 ctcccccaccc acatacattt ctgccagtgt tcacaatgac actcagcggt catgtctgga 20341 catgagtgcc cagggaatat gcccaagcta tgccttgtcc tcttgtcctg tttgcatttc 20401 actgggagct tgcactatgc agctccagtt tcctgcagtg atcagggtcc tgcaagcagt 20461 ggggaagggg gccaaggtat tggaggactc cctcccagct ttggaagcct catccgcgtg 20521 tgtgtgtgtg tgtatgtgta gacaagctct cgctctgtca cccagctggg agtgcagtgg 20581 tgcaatcatg gttcactgca gtcttgacct tttgggctca agtgatcctc ccacctcagc 20641 ctcctgagta gctgggacca taggctcaca acaccacacc tggcaaattt gatttttttt 20701 ttttttccag agacgggtc tcgcaacatt gcccagactt cctttgtgtt agtaataaaa 20761 gctttctcaa ctgcctcagc cttgtgtgag ttgaggggag gtgtcacatc cagctggagt 20821 cctttctaag cagccacagc ctgatcctcc cacttcctcc cccaagaaaa cattgtgggt 20881 tgatggccat accctgaggt tctggtccaa atcggacttt ctatgaccctt ctgggtctct 20941 agtgaaaact aaagactcct ctccagaaaa aaacatttgg ttttctaatga ggcctggaat 21001 cttattcttg acctggggag cggaatccct ttttgcagta ctcccgggcc ctctgttggg 21061 gcctccccctt cctctccagg gtggagtcga ggaggcgggg ctgcgggcct ccttatctct 21121 agagccggcc ctggctctct ggcgcgggggc cccttagtcc gggcttttg ccatggggtc 21181 tctgttccct ctgtcgctgc tgtttttttt ggcggccgcc tacccgggag ttgggagcgc 21241 gctgggacgc cggactaagc gggcgcaaag ccccaagggt agccctctcg cgcccctccgg 21301 gacctcagtg cccttctggg tgcgcatgag cccggagttc gtgctgtgc agccggggaa 21361 gtcagtgcag ctcaattgca gcaacagctg tccccagccg cagaattcca gcctccgcac 21421 cccgctgcgg caaggcaaga cgctcagagg gccgggttgg gtgtcttacc agctgctcga 21481 cgtgagggcc tggagctccc tcgcgcactg cctcgtgacc tgcgcaggaa aaacacgctg 21541 ggccacctcc aggatcaccg cctacagtga gggacagggg ctcggtcccg gctgggtga 21601 gggagggg ctggaagagg tgggggaagg gtagttgaca gtcgctctat agggagcgcc 21661 cgcggacctc actcagaggc tccccccttgc cttagaaccg ccccacagcg tgattttgga 21721 gcctccggtc ttaaagggca ggaaatacac tttgcgctgc cacgtgacgc aggtgttccc 21781 ggtgggctac ttggttgtga ccctgaggca tggaagccgg gtcatctatt ccgaaagcct 21841 ggagcgcttc accggcctgg atctggccaa cgtgaccttg acctacgagt ttgctgctgg 21901 accccgcgac ttctggcagc ccgtgatctg ccacgcgcgc ctcaatctcg acggcctggt 21961 ggtccgcaac agctcggcac ccattacact gatgctcggt gaggcacccc tgtaaccctg 22021 gggactagga ggaaggggggc agagagagtt atgaccccga gagggcgcac agaccaagcg 22081 tgagctccac gcgggtcgac agacctccct gtgttccgtt cctaattctc gccttctgct 22141 cccagcttgg agccccgcgc ccacagcttt ggcctccggt tccatcgctg cccttgtagg 22201 gatcctcctc actgtgggcg ctgcgtacct atgcaagtgc ctagc-
tatga agtcccaggc 22261 gtaaaggggg atgttctatg ccggctgagc gagaaaaga
ggaatatgaa acaatctggg 22321 gaaatggcca tacatggtgg ctgacgcctg taatcccagc
actttgggag gccgaggcag 22381 gagaatcgct tgagcccagg agttcgagac cagcctggac
aacatagtga gaccccgtct 22441 atgcaaaaaa tacacaaatt agcctggtgt ggtggcccgc acct-
gtggtc ccagctaccc 22501 gggaggctga gttgggagga tcctttgagc cctgaaagtc gag-
gttgcag tgagccttga 22561 tcgtgccact gcactccagc ctgggggaca gagcacgacc
ctgtctccaa aaataaaata 22621 aaaataaaaa taaatattgg cggggggaacc ctctggaatc
aataaaggct tccttaacca 22681 gcctctgtcc tgtgacctaa gggtccgcat tactgcccctt cttcg-
gagga actggtttgt 22741 ttttgttgtt gttgttgttt ttgcgatcac tttct (SEQ ID NO:15)

BC005930

*Homo sapiens* CD58 molecule, mRNA 1 gtaggcggtg cttgaactta gggctgcttg tggctgggca ctcgcgcaga
ggccggcccg 61 acgagccatg gttgctggga gcgacgcggg gcgggccctg ggggtc-
ctca gcgtggtctg 121 cctgctgcac tgctttggtt tcatcagctg tttttcccaa caaatatatg
gtgttgtgta 181 tgggaatgta actttccatg taccaagcaa tgtgccttta aaagaggtcc
tatggaaaaa 241 acaaaaggat aaagttgcag aactggaaaa ttctgaattc agagctttct
catcttttaa 301 aaatagggtt tatttagaca ctgtgtcagg tagcctcact atctacaact
taacatcatc 361 agatgaagat gagtatgaaa tggaatcgcc aaatattact gatac-
catga agttcttct 421 ttatgtgctt gagtctcttc catctcccac actaacttgt gcattgacta
atggaagcat 481 tgaagtccaa tgcatgatac cagagtatta caacagccat cgag-
gactta taatgtactc 541 atgggattgt cctatggagc aatgtaaacg taactcaacc agtatatatt
ttaagatgga 601 aaatgatctt ccacaaaaaa tacagtgtac tcttagcaat ccattattta
atacaacatc 661 atcaatcatt ttgacaacct gtatcccaag cagcggtcat tcaagacaca
gatatgcact 721 tatacccata ccattagcag taattacaac atgtattgtg ctgtatatga
atggtatgta 781 tgcttttaa aacaaaatag tttgaaaact tgcattgttt tccaaaggtc
agaaaatagt 841 ttaaggatga aaataagtt tgaaatttta gacattcgaa aaaaaaaa
aaaagaaaa 901 aaaaaaa (SEQ ID NO:16)

REFERENCES

Abdel-Wahab et al., *Cell Immunol.*, 224:86 (2003).
Akazawa et al., *Febs. Lett.*, 581:3334 (2007).
An et al., *Hum. Gene Ther.*, 14:1207 (2003).
Annoni et al., *Blood*, 114:5152 (2009).
Ansorge et al., *J. Gene Med.*, 11:868 (2009).
Apolonia et al., *Mol. Ther.*, 15:1947 (2007).
Arce et al., *Mol. Ther.*, 17:1643 (2009).
Bancilereau & Steinman, Nature, 392:245 (1998).
Beignon et al., *J. Virol.*, 83:10963 (2009).
Besche et al., *J. Gene Med.*, 12:231 (2010).
Bonifaz et al., *J. Exp. Med.*, 196:1627 (2002).
Bontkes et al., *Clin. Immunol.*, 127:375 (2008).
Breckpot et al., *Curr. Gene Ther.*, 8:438 (2008).
Breckpot et al., *Gene Ther.*, 14:847 (2007).
Breckpot et al., *J. Immunol.*, 172:2232 (2004).
Breckpot et al., *J. Virol.*, 84:5627 (2010).
Brown et al., *Blood*, 109:2797 (2007).
Brown et al., *Nat. Biotechnol.*, 25:1457 (2007).
Brown et al., *Nat. Med.*, 12:585 (2006).
Carissimi et al., *Autoimmun. Rev.*, 8:520 (2009).
Case et al., *Proc. Natl. Acad. Sci. USA*, 96:2988 (1999).
Chapatte et al., *Cancer Res.*, 66:1155 (2006).
Chen et al., *Retrovirology*, 1:37 (2004).
Coutant et al., *PLoS One*, 3:e3973 (2008).
Creusot et al., *Clin. Immunol.*, 127:176 (2008).
Cui et al., *Blood*, 99:399 (2002).
Dai et al., *Proc. Natl. Acad. Sci. USA*, 106:20382 (2009).
Dresch et al., *J. Immunol.*, 181:4495 (2008).
Dullaers et al., *Gene Ther.*, 13:630 (2006).
Esslinger et al., *J. Clin. Invest.*, 111:1673 (2003).
Felice et al., *PLoS One*, 4: e4571 (2009).
Fire, A., *Trends Genet.*, 15:358 (1999).
Fry et al., *Gene Ther.*, 9:220 (2002).
Fukushima et al., *J. Immunother.*, 32:219 (2009).
Furmanov et al., *J. Immunol.*, 184:4889 (2010).
Gentner et al., *Nat. Methods*, 6:63 (2009).
Gruber et al., *Blood*, 96:1327 (2000).
Gu et al., *Scand. J. Immunol.*, 64:588 (2006).
Haase et al., *Scand. J. Immunol.*, 59:237 (2004).
Han et al., *Mol. Ther.*, 16:269 (2008).
Hannon, Nature, 418:244 (2002).
Hawiger et al., *J. Exp. Med.*, 194:769 (2001).
He and Falo, *Immunol. Res.*, 36:101 (2006).
He et al., *Immunity*, 24:643 (2006).
He et al., *J. Immunol.*, 174:3808 (2005).
Henry et al. *J. Immunol.*, 181:7230 (2008).
Hill et al., *J. Immunol.*, 171:691 (2003).
Hirata et al., *J. Immunol.*, 174:1888 (2005).
Hoeck & Woisetschlager, *J. Immunol.*, 166:4507 (2001).
Hosoya et al., *J. Med. Virol.*, 80:373 (2008).
Huang et al., *Clin. Immunol.*, 119:280 (2006).
Iglesias et al., *J. Gene Med.*, 8:265 (2006).
Iglesias et al., *Mol. Ther.*, 15:1203 (2007).
Inaba et al., *J. Exp. Med.*, 176:1693 (1992).
Jirmo et al. *Vaccine*, 28:922 (2010).
Kafri et al., *Nat. Genet.*, 17:314 (1997).
Kalinski and Moser, *Nat. Rev. Immunol.*, 5:251 (2005).
Kalinski et al., *Methods Mol. Biol.*, 595:117 (2010).
Keller et al., *Blood*, 113:5167 (2009).
Kim et al., *Hum. Gene Ther.*, 16:1255 (2005).
Kim et al., *J. Immunol.*, 179:2242 (2007).
Kim et al., *J. Virol.*, 72:811 (1998).
Kobayashi et al., *Int. J. Hematol.*, 79:377 (2004).
Koya et al., *J. Immunother.*, 26:451 (2003).
Kung et al., *Hum. Gene Ther.*, 16:527 (2005).
Kung et al., *J. Virol.*, 74:3668 (2000).
Kung et al., *Mol. Ther.*, 8:981 (2003).
Kutner et al., *Nat. Protoc.*, 4:495 (2009).
Kyte et al., *Cancer Immunol. Immunother.*, 56:659 (2007).
Laderach et al., *J. Immunol.*, 171:1750 (2003).
Lai et al., *Proc. Natl. Acad. Sci. USA*, 105:14993 (2008).
Li et al., *Immunol. Res.*, 30:215 (2004).
Li et al., *J. Immunol.*, 178:5480 (2007).
Liu et al., *Eur. J. Immunol.*, 34:1680 (2004).
Lopes et al., *Cancer Immunol. Immunother.*, 55:1011 (2006).
Mahnke et al., *Nat. Biotechnol.*, 21:903 (2003).
Metharom et al., *Cell Mol. Immunol.*, 2:281 (2005).
Metharom et al., *Hum. Gene Ther.*, 12:2203 (2001).
Min et al., *J. Immunol.*, 164:161 (2000).

Miyoshi et al., *J. Virol.*, 72:8150 (1998).
Mochizuki et al., *J. Virol.*, 72:8873 (1998).
Morizono et al. (2010, in press. *J. Virol.*).
Morizono et al., *J. Gene Med.*, 11:655 (2009).
Morizono et al., *Nat. Med.*, 11:346 (2005).
Mossoba et al., *Mol. Ther.*, 16:607 (2008).
Naldini et al., *Proc. Natl. Acad. Sci. USA*, 93:11382 (1996).
Naldini et al., *Science*, 272:263 (1996).
Negri et al., *Hum. Gene Ther.*, 21:1029 (2010).
Negri et al., *Mol. Ther.*, 15:1716 (2007).
O'Connell et al., *Nat. Rev. Immunol.*, 10:111 (2010).
Ohmura-Hoshino et al., *J. Immunol.*, 177:341 (2006).
Orabona et al., *J. Immunol.*, 174:6582 (2005).
O'Rourke et al., *Transplantation*, 69:1440 (2000).
O'Sullivan and Thomas, *Crit. Rev. Immunol.*, 23:83 (2003).
Palmowski et al., *J. Immunol.*, 172:1582 (2004).
Pecher et al., *Anticancer Res.*, 21:2591 (2001).
Pecher et al., *Cancer Immunol. Immunother.*, 51:669 (2002).
Perone et al., *J. Immunol.*, 177:5278 (2006).
Pichlmair et al., *J. Virol.*, 81:539 (2007).
Qin et al., *Proc. Natl. Acad. Sci. USA.*, 100:183 (2003).
Rahim et al., *Gene Ther.*, 16:509 (2009).
Reis, *Nat. Rev. Immunol.*, 6:476 (2006).
Reynolds et al., *Nat. Biotechnol.*, (2004).
Robbins & Rossi, *Nat. Med.*, 11:250 (2005).
Robertson et al., *J. Immunol.*, 164:4706 (2000).
Roe et al., *Embo. J.*, 12:2099 (1993).
Rowe et al., *Mol. Ther.*, 13:310 (2006).
Scheinecker et al., *J. Exp. Med.*, 196:1079 (2002).
Sharpe and Freeman, *Nat. Rev. Immunol.*, 2:116 (2002).
Song et al., *Nat. Med.*, 14:258 (2008).
Steinman et al., *Annu. Rev. Immunol.*, 21:685 (2003).
Steinman et al., *J. Exp. Med.*, 191:411 (2000).
Stewart et al., *RNA*, 9:493 (2003).
Strobel et al., *Gene Ther.*, 7:2028 (2000).
Takayama et al., *Transplantation*, 74:112 (2002).
Thomson et al., *J. Immunol.*, 177:2250 (2006).
Thomson et al., *Mol. Ther.*, 15:818 (2007).
Tiao et al., *Transplant Proc.*, 36:1592 (2004).
Toscano et al., *Mol. Ther.*, 18:1035 (2010).
Tran and Kung, *Mol. Ther.*, 15:1331 (2007).
Tsang et al., *Cancer Res.*, 61; 7568 (2001).
Tsao et al., *Arch. Dermatol.*, 138:799 (2002).
Tuyaerts et al. *J. Immunol. Methods*, 264:135 (2002).
Van Gulck et al., *Blood*, 107:1818 (2006).
VandenDriessche et al., *Blood*, 100:813 (2002).
Veron et al., *J. Transl. Med.*, 7:10 (2009).
Wang et al., *Blood*, 113:2906 (2009).
Wang et al., *Immunology*, 128:43 (2009).
Wang et al., *J. Immunol.*, 177:2175 (2006).
Wilson et al., *Blood*, 102:2187 (2003).
Yanagita et al., *Br. J. Haematol.*, 124:454 (2004).
Yang et al., *Clin. Cancer Res.*, 11:5603 (2005).
Yang et al., *Nat. Biotechnol.*, 26:326 (2008).
Yu et al., *J. Transl. Med.*, 6:56 (2008).
Yu et al., *J. Viral. Hepat.*, 15:459 (2008).
Yurkovetsky et al., *J. Gene Med.*, 8:129 (2006).
Zabaleta et al., *Mol. Ther.*, 16:210 (2008).
Zarei et al., *J. Virol.*, 78:7843 (2004).
Zhang et al., *Cancer Gene Ther.*, 15:73 (2008).
Zhang et al., *J. Immunol. Methods*, 344:87 (2009).
Zhang et al., *J. Mol. Med.*, 82:240 (2004).
Zhang et al., *Mol. Immunol.*, 46:657 (2009).
Zhang et al., *Nat. Med.*, 6:782 (2000).
Zhang et al., *Proc. Natl. Acad. Sci. USA*, 100:15101 (2003).
Zhang et al., *Transgenic Res.*, 18:921-931 (2009).
Zufferey et al., *J. Virol.*, 72:9873 (1998).
Zufferey et al., *Nat. Biotechnol.*, 15:871 (1997).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method of making stably transduced mammalian dendritic cells with altered immune properties, comprising providing a population of mammalian dendritic cells; stably transducing the cells with a recombinant helper-free lentivirus comprising a genome having a transcription cassette comprising nucleic acid sequences for CD4, the expression of which sequences in the dendritic cells is capable of inducing RNAi, thereby decreasing cell surface expression of CD40; and selecting transduced dendritic cells with decreased levels of CD40 expression that result in antigen-specific T cell tolerization or Th2 polarization in vivo relative to corresponding dendritic cells that are not transduced with the recombinant helper-free lentivirus, wherein the nucleic acid sequences for CD40 comprise CTGGACAAGCTGTGAGGATAA (SEQ ID NO:6), GCAGGGTACTGGCTAAATAAA (SEQ ID NO:1) or CCAAAGGATAATGAGATGTTA (SEQ ID NO:2).

2. The method of claim 1 wherein the cells are human cells.

3. The method of claim 1 wherein the cells are immature primary cells.

4. The method of claim 1 further comprising contacting the transduced cells with an agent that stimulates expression of one or more co-stimulatory molecules.

5. The method of claim 4 further comprising contacting the transduced cells with an antigen.

6. A stably transduced mammalian dendritic cell prepared by the method of claim 1.

7. A population of isolated stably lentivirus transduced mammalian dendritic cells comprising a recombinant lentivirus comprising a transcription cassette comprising nucleic acid sequences for CD40, the expression of which sequences in the dendritic cells is capable of inducing RNAi, thereby decreasing cell surface expression of CD40, which population is selected to have decreased levels of CD40 expression that result in antigen-specific T cell tolerization or Th2 polarization in vivo relative to corresponding dendritic cells that are not transduced with the recombinant helper-free lentivirus, wherein the nucleic acid sequences for CD40 comprise CTGGACAAGCTGTGAGGATAA (SEQ ID NO:6), GCAGGGTACTGGCTAAATAAA (SEQ ID NO:1) or CCAAAGGATAATGAGATGTTA (SEQ ID NO:2).

8. The dendritic cells of claim 7 wherein the cells are human cells.

9. The dendritic cells of claim 7 wherein the stably transduced dendritic cells have decreased levels of CD40 relative to corresponding cells that are not transduced by the recombinant helper-free lentivirus.

10. The method of claim 1 wherein the nucleic acid sequences for CD40 comprise CTGGACAAGCTGTGAGGATAA (SEQ ID NO:6), GCAGGGTACTG- GCTAAATAAA (SEQ ID NO:1) or CCAAAGGATAAT-GAGATGTTA (SEQ ID NO:2).

11. The dendritic cells of claim 7 wherein the nucleic acid sequences for CD40 comprise GCAGGGTACTG-GCTAAATAAA (SEQ ID NO:1) or CCAAAGGATAAT-GAGATGTTA (SEQ ID NO:2).

\* \* \* \* \*

SEQUENCE LISTING

```
<160> NUMBER OF SEQ ID NOS: 17

<210> SEQ ID NO 1
<211> LENGTH: 21
<212> TYPE: DNA
<213> ORGANISM: Mus musculus

<400> SEQUENCE: 1
gcagggtact ggctaaataa a                                              21

<210> SEQ ID NO 2
<211> LENGTH: 21
<212> TYPE: DNA
<213> ORGANISM: Mus musculus

<400> SEQUENCE: 2
ccaaaggata atgagatgtt a                                              21

<210> SEQ ID NO 3
<211> LENGTH: 21
<212> TYPE: DNA
<213> ORGANISM: Mus musculus

<400> SEQUENCE: 3
```

-continued

```
taccatttag ttcttgaata a                                      21

<210> SEQ ID NO 4
<211> LENGTH: 21
<212> TYPE: DNA
<213> ORGANISM: Mus musculus

<400> SEQUENCE: 4
aaaggtggtc aagaaaccaa a                                      21

<210> SEQ ID NO 5
<211> LENGTH: 21
<212> TYPE: DNA
<213> ORGANISM: Mus musculus

<400> SEQUENCE: 5
gtggtgtatt gtagaaatta t                                      21

<210> SEQ ID NO 6
<211> LENGTH: 21
<212> TYPE: DNA
<213> ORGANISM: Mus musculus

<400> SEQUENCE: 6
ctggacaagc tgtgaggata a                                      21

<210> SEQ ID NO 7
<211> LENGTH: 19
<212> TYPE: DNA
<213> ORGANISM: Mus musculus

<400> SEQUENCE: 7
ttacaactct cctcatgaa                                         19

<210> SEQ ID NO 8
<211> LENGTH: 19
<212> TYPE: DNA
<213> ORGANISM: Mus musculus

<400> SEQUENCE: 8
tctacgactt cacaatgtt                                         19

<210> SEQ ID NO 9
<211> LENGTH: 8
<212> TYPE: PRT
<213> ORGANISM: Mus musculus

<400> SEQUENCE: 9

Ser Ile Ile Asn Phe Glu Lys Leu
 1               5

<210> SEQ ID NO 10
<211> LENGTH: 17
<212> TYPE: PRT
<213> ORGANISM: Mus musculus

<400> SEQUENCE: 10

Ile Ser Gln Ala Val His Ala Ala His Ala Glu Ile Asn Glu Ala Gly
 1               5                  10                  15

Arg

<210> SEQ ID NO 11
<211> LENGTH: 1611
```

```
<212> TYPE: DNA
<213> ORGANISM: Mus musculus

<400> SEQUENCE: 11
atggtgtctt tgcctcggct gtgcgcgcta tggggctgct tgttgacagc ggtccatcta      60
gggcagtgtg ttacgtgcag tgacaaacag tacctccacg atggccagtg ctgtgatttg     120
tgccagccag gaagccgact gacaagccac tgcacagctc ttgagaagac ccaatgccac     180
ccatgtgact caggcgaatt ctcagcccag tggaacaggg agattcgctg tcaccagcac     240
agacactgtg aacccaatca agggcttcgg gttaagaagg agggcaccgc agaatcagac     300
actgtctgta cctgtaagga aggacaacac tgcaccagca aggattgcga ggcatgtgct     360
cagcacacgc cctgtatccc tggctttgga gttatggaga tggccactga gaccactgat     420
accgtctgtc atccctgccc agtcggcttc ttctccaatc agtcatcact tttcgaaaag     480
tgttatccct ggacaagctg tgaggataag aacttggagg tcctacagaa aggaacgagt     540
cagactaatg tcatctgtgg tttaaagtcc cggatgcgag ccctgctggt cattcctgtc     600
gtgatgggca tcctcatcac cattttcggg gtgtttctct atatcaaaaa ggtggtcaag     660
aaaccaaagg ataatgagat cttaccccct gcggctcgac ggcaagatcc ccaggagatg     720
gaagattatc ccggtcataa caccgctgct ccagtgcagg agacgctgca cgggtgtcag     780
cctgtcacac aggaggatgg taaagagagt cgcatctcag tgcaggagcg gcaggtgaca     840
gacagcatag ccttgaggcc cctggtctga accctggaac tgctttggag gcgatggctc     900
ggctcgggag caggggcctg gctctgagga ctgcttgctg acctttgaag tttgagatga     960
gccaagacag agcccagtgc agctaactct catgcctgcc ccctatcatt tctcaacttg    1020
cttttttaagg atggagggag agctcgggca tcggggtcc acagtgatac ctaccaagtg    1080
cagcagtgca ggacccagag tcgtcttgct gcggcgttca ctgtaaggag tcatggacac    1140
aggagtccgt ggcccacagc ttgtgctgct agagggcacc tggttgccca tcagcagggt    1200
actggctaaa taaatctgta attatttata caatgacatc tcagaaactc tagcaggtgg    1260
ggcagaaaac aggtagtaga atgatgggta gagaaatagc ttttaaaaca cattccaagg    1320
caggtaagat ggcttttgtg agtaaaggag cttgctgccc aaacccggtt acctgatttt    1380
gatccctggg acttcatggt aaagggaga gaaccaaatc cagagggttg tcatttgacc    1440
tccatgtgtg ctctgtggta atgtaccccg tgtgtgcaca tgtgcacata tcctaaaatg    1500
gatgtggtgg tgtattgtag aaattattta atcccgccct gggggtttcta cctgtgtgtt    1560
accatttagt tcttgaataa aagacacact caacctttat atttacaata a             1611

<210> SEQ ID NO 12
<211> LENGTH: 1834
<212> TYPE: DNA
<213> ORGANISM: Homo sapiens

<400> SEQUENCE: 12
actttgacag tcttctcatg ctgcctctgc caccttctct gccagaagat accatttcaa      60
ctttaacaca gcatgatcga acatacaac caaacttctc cccgatctgc ggccactgga     120
ctgcccatca gcatgaaaat ttttatgtat ttacttactg ttttttcttat cacccagatg     180
attgggtcag cacttttttgc tgtgtatctt catgaaggt tggacaagat agaagatgaa     240
aggaatcttc atgaagattt tgtattcatg aaaacgatac agagatgcaa cacaggagaa     300
agatccttat ccttactgaa ctgtgaggag attaaaagcc agtttgaagg ctttgtgaag     360
gatataatgt taaacaaaga ggagacgaag aaagaaaaca gctttgaaat gcaaaaaggt     420
```

```
gatcagaatc ctcaaattgc ggcacatgtc ataagtgagg ccagcagtaa aacaacatct    480
gtgttacagt gggctgaaaa aggatactac accatgagca acaacttggt aaccctggaa    540
aatgggaaac agctgaccgt taaaagacaa ggactctatt atatctatgc ccaagtcacc    600
ttctgttcca atcgggaagc ttcgagtcaa gctccattta tagccagcct ctgcctaaag    660
tcccccggta gattcgagag aatcttactc agagctgcaa atacccacag ttccgccaaa    720
ccttgcgggc aacaatccat tcacttggga ggagtatttg aattgcaacc aggtgcttcg    780
gtgtttgtca atgtgactga tccaagccaa gtgagccatg gcactggctt cacgtccttt    840
ggcttactca aactctgaac agtgtcacct tgcaggctgt ggtggagctg acgctgggag    900
tcttcataat acagcacagc ggttaagccc accccctgtt aactgcctat ttataaccct    960
aggatcctcc ttatggagaa ctatttatta tacactccaa ggcatgtaga actgtaataa   1020
gtgaattaca ggtcacatga aaccaaaacg ggccctgctc cataagagct tatatatctg   1080
aagcagcaac cccactgatg cagacatcca gagagtccta tgaaaagaca aggccattat   1140
gcacaggttg aattctgagt aaacagcaga taacttgcca agttcagttt tgtttctttg   1200
cgtgcagtgt ctttccatgg ataatgcatt tgatttatca gtgaagatgc agaagggaaa   1260
tggggagcct cagctcacat tcagttatgg ttgactctgg gttcctatgg ccttgttgga   1320
gggggccagg ctctagaacg tctaacacag tggagaaccg aaacccccccc cccccccccg   1380 ccaccctctc ggacagttat tcattctctt tcaatctctc tctctccatc tctctctttc   1440
agtctctctc tctcaacctc tttcttccaa tctctctttc tcaatctctc tgtttccctt   1500
tgtcagtctc ttccctcccc cagtctctct tctcaatccc cctttctaac acacacacac   1560
acacacacac acacacacac acacacacac acacacacac agagtcaggc cgttgctagt   1620
cagttctctt cttttccaccc tgtccctatc tctaccacta tagatgaggg tgaggagtag   1680
ggagtgcagc cctgagcctg cccactcctc attacgaaat gactgtattt aaaggaaatc   1740
tattgtatct acctgcagtc tccattgttt ccagagtgaa cttgtaatta tcttgttatt   1800
tattttttga ataataaaga cctcttaaca ttaa                               1834

<210> SEQ ID NO 13
<211> LENGTH: 2757
<212> TYPE: DNA
<213> ORGANISM: Homo sapiens

<400> SEQUENCE: 13
gacaagtact gagtgaactc aaaccctctg taaagtaaca gaagttagaa ggggaaatgt     60
cgcctctctg aagattaccc aaagaaaaag tgatttgtca ttgctttata gactgtaaga    120
agagaacatc tcagaagtgg agtcttaccc tgaaatcaaa ggatttaaag aaaaagtgga    180
atttttcttc agcaagctgt gaaactaaat ccacaacctt tggagaccca ggaacaccct    240
ccaatctctg tgtgttttgt aaacatcact ggagggtctt ctacgtgagc aattggattg    300
tcatcagccc tgcctgtttt gcacctggga agtgccctgg tcttacttgg gtccaaattg    360
ttggctttca cttttgaccc taagcatctg aagccatggg ccacacacgg aggcagggaa    420
catcaccatc caagtgtcca tacctcaatt tctttcagct cttggtgctg gctggtcttt    480
ctcacttctg ttcaggtgtt atccacgtga ccaaggaagt gaaagaagtg caacgctgt    540 cctgtggtca caatgtttct gttgaagagc tggcacaaac tcgcatctac tggcaaaagg    600
agaagaaaat ggtgctgact atgatgtctg gggacatgaa tatatggccc gagtacaaga    660
accggaccat ctttgatatc actaataacc tctccattgt gatcctggct ctgcgcccat    720
```

| | |
|---|---:|
| ctgacgaggg cacatacgag tgtgttgttc tgaagtatga aaaagacgct ttcaagcggg | 780 |
| aacacctggc tgaagtgacg ttatcagtca agctgactt ccctacacct agtatatctg | 840 |
| actttgaaat tccaacttct aatattagaa ggataatttg ctcaacctct ggaggttttc | 900 |
| cagagcctca cctctcctgg ttggaaaatg gagaagaatt aaatgccatc aacacaacag | 960 |
| tttcccaaga tcctgaaact gagctctatg ctgttagcag caaactggat ttcaatatga | 1020 |
| caaccaacca cagcttcatg tgtctcatca agtatggaca tttaagagtg aatcagacct | 1080 |
| tcaactggaa tacaaccaag caagagcatt tcctgataaa cctgctccca tcctgggcca | 1140 |
| ttaccttaat ctcagtaaat ggaattttg tgatatgctg cctgacctac tgctttgccc | 1200 |
| caagatgcag agagagaagg aggaatgaga gattgagaag ggaaagtgta cgccctgtat | 1260 |
| aacagtgtcc gcagaagcaa ggggctgaaa agatctgaag gtcccacctc catttgcaat | 1320 |
| tgacctcttc tgggaacttc ctcagatgga caagattacc ccaccttgcc ctttacgtat | 1380 |
| ctgctcttag gtgcttcttc acttcagttg ctttgcagga agtgtctaga ggaatatggt | 1440 |
| gggcacagaa gtagctctgg tgaccttgat caaggtgttt tgaaatgcag aattcttgag | 1500 |
| ttctggaagg gactttagag aataccagtg ttattaatga caaaggcact gaggcccagg | 1560 |
| gaggtgaccc gaattataaa ggccagcgcc agaacccaga tttcctaact ctggtgctct | 1620 |
| ttccctttat cagtttgact gtggcctgtt aactggtata tacatatata tgtcaggcaa | 1680 |
| agtgctgctg gaagtagaat ttgtccaata acaggtcaac ttcagagact atctgatttc | 1740 |
| ctaatgtcag agtagaagat tttatgctgc tgtttacaaa agcccaatgt aatgcatagg | 1800 |
| aagtatggca tgaacatctt taggagacta atggaaatat tattggtgtt tacccagtat | 1860 |
| tccatttttt tcattgtgtt ctctattgct gctctctcac tccccatga ggtacagcag | 1920 |
| aaaggagaac tatccaaaac taatttcctc tgacatgtaa gacgaatgat ttaggtacgt | 1980 |
| caaagcagta gtcaaggagg aaagggatag tccaaagact taactggttc atattggact | 2040 |
| gataatctct ttaaatggct ttatgctagt ttgacctcat ttgtaaaata tttatgagaa | 2100 |
| agttctcatt taaaatgaga tcgttgttta cagtgtatgt actaagcagt aagctatctt | 2160 |
| caaatgtcta aggtagtaac tttccatagg gcctccttag atccctaaga tggcttttc | 2220 |
| tccttggtat ttctgggtct ttctgacatc agcagagaac tggaaagaca tagccaactg | 2280 |
| ctgttcatgt tactcatgac tcctttctct aaaactgcct tccacaattc actagaccag | 2340 |
| aagtggacgc aacttaagct gggataatca cattatcatc tgaaaatctg gagttgaaca | 2400 |
| gcaaaagaag acaacatttc tcaaatgcac atctcatggc agctaagcca catggctggg | 2460 |
| atttaaagcc tttagagcca gcccatggct ttagctacct cactatgctg cttcacaaac | 2520 |
| cttgctcctg tgtaaaacta tattctcagt gtagggcaga gaggtctaac accaacataa | 2580 |
| ggtactagca gtgtttcccg tattgacagg aatacttaac tcaataattc ttttcttttc | 2640 |
| catttagtaa cagttgtgat gactatgttt ctattctaag taattcctgt attctacagc | 2700 |
| agatactttg tcagcaatac taagggaaga aacaaagttg aaccgtttct ttaataa | 2757 |

```
<210> SEQ ID NO 14
<211> LENGTH: 913
<212> TYPE: DNA
<213> ORGANISM: Homo sapiens

<400> SEQUENCE: 14
```

| | |
|---|---:|
| ccagagaggg gcaggctggt cccctgacag gttgaagcaa gtagacgccc aggagccccg | 60 |
| ggaggggggct gcagtttcct tccttccttc tcggcagcgc tccgcgcccc catcgcccct | 120 |

```
cctgcgctag cggaggtgat cgccgcggcg atgccggagg agggttcggg ctgctcggtg      180
cggcgcaggc cctatgggtg cgtcctgcgg gctgctttgg tcccattggt cgcgggcttg      240
gtgatctgcc tcgtggtgtg catccagcgc ttcgcacagg ctcagcagca gctgccgctc      300
gagtcacttg ggtgggacgt agctgagctg cagctgaatc acacaggacc tcagcaggac      360
cccaggctat actggcaggg gggcccagca ctgggccgct ccttcctgca tggaccagag      420
ctggacaagg ggcagctacg tatccatcgt gatggcatct acatggtaca catccaggtg      480
acgctggcca tctgctcctc cacgacggcc tccaggcacc accccaccac cctggccgtg      540
ggaatctgct ctcccgcctc ccgtagcatc agcctgctgc gtctcagctt ccaccaaggt      600
tgtaccattg cctcccagcg cctgacgccc tggcccgag gggacacact ctgcaccaac      660
ctcactggga cacttttgcc ttcccgaaac actgatgaga ccttctttgg agtgcagtgg      720
gtgcgcccct gaccactgct gctgattagg gttttttaaa ttttattta ttttatttaa      780 gttcaagaga aaagtgtac acacaggggc cacccgggg tggggtggga gtgtggtggg      840
gcgtagtggt ggcaggacaa gagaaggcat tgagcttttt ctttcatttt cctattaaaa      900
aatacaaaaa tca                                                         913

<210> SEQ ID NO 15
<211> LENGTH: 22775
<212> TYPE: DNA
<213> ORGANISM: Homo sapiens

<400> SEQUENCE: 15
attttatctg ctcgtccagc atggtcagcc ctccactttt taaatttat tttatttatt        60 tttttgagac agagtctcac tctgttgtcc aggttggagt ccagtggcgt gatttcggct      120
cactgcaacc tctacttccc aggttcgagc aattctcctg cctcagcttc ccgagtagct      180
gggattacag gcccgcgtcc ccacacctag ctaattttg tattttagt agagacaggg      240 tttcaccatg ttggccaggc tggtctcgaa ctcctgacct caggtgattc tcctgccttg      300
gcctcccaaa gtgctgagat tacaggtgtg agccactgca cacggcctta aattttattt      360
attatttatt tatttattta tttagagact tagtctcact ctgttgccca ggctggagtg      420
cagtggcatg tctcggctc actgcactcc acctcctggg ttcacgccat tctcctgcct      480
cagcctcccg agtagctggg actacaggcg cccaccacca ctcccggcta attttgtat      540 ttttagtaga tgggggtttt cactgtgtta gccaggatag tctcgatctc ctgacctcgt      600
gatccgcctg cctcggcctc ccaaagtgct gggattactt attttgtttt ttgtagagac      660
aggttctcac tgtgttgccc aggctggtct tgaactcctg atctcaagtg atcttcccac      720
ctcagtctct caagggctg ggattacagg ggtgagccac tgcaccccac cttccctcta      780 cttttttgacg gtttccttct gctatgaatg tgcatgtcca gttgtctgct tcttagaact      840
gatatttacc ttcctcatcc atcagccatt ggaggaggac tgggaccgct cagattattg      900
atctgaccca ttctttcggc agggtttcct ggtggctgtc ttccatcacc aaaactggaa      960
tcagaagagt ttccatagcc ctttttttttt ccccacatct ttgctgaagc agagttttga     1020
aaaacaaaac cacaaactaa gctattcccc agaagaaatc tgtaatcaaa gataagctct     1080
gccgggcaca gtggctcacg ccttttggag gccaggcgg gcggatcacc tgaggtcagg     1140
agttctagac ctgccaggcc aacatggtaa aacctcatct ctactaaaaa tacaaaaatt     1200
agctagatgt ggtggtgggt acctgtagtc tcagctacct gggaggctga ggcaagaaa     1260 tcgcttgaac ctgggaagta gaggttgcag tgagccgaga ttgcaccact gcactccagc     1320
```

```
ctgggcgacg gagtgagacg acctcacaaa aatttacata aataaaatga aaagtaaaat    1380
aaaaatacaa aagttggccg ggtgcgtttg ctcacgcctg taatcccagc actttgggag    1440
ggtgaggcag gcagataatg aggtaagaag atcgagacca tcctggctaa cacggtgaaa    1500
ccctgtctct actaaaaata caaaaaatta gctgtgcgtg gtgacacgca cctgtagtcc    1560
cagctatttg ggaggctgag gcaggagaat cacttgaacc tgggaggtgg aggttgcagt    1620
gagccgagat cgcaccactg cactccagcc tgggccacag agtgagactc catcttgaaa    1680
aaaaaaaaaa atacaaaagt tagccagggg tgttggtggg tgcctgtaat cccagctatt    1740
tgggaggcta aggcagaaga atttcttgaa cctaggaaac ggaggttgca gtgagccgag    1800
atcacacctc tgtactccag cctggacaac agagcgagac tttgtctcaa aaaaaaaaa    1860
aaaaaaaaaa ctaaataggc cgggagcagt ggctcatgcc tataatccca gccctttggg    1920
aggccaaggc aggtggatca cttgaggtca ggagtttgag accaggctgg ccaacatggt    1980
gtaaccccgt ctctactaaa aacacaaaaa ttagccgggt ctggtggcgt atgtctgtaa    2040
tcccagctac tcgggaggct gaggcaggag aatcacttaa acctgggagg caggggttgc    2100
agtgagctga gatcgtgcca ctgcactcta gccagggtga cagagtgaaa ctctgtctca    2160
aaaaattaaa aaagaaattc agcaagtaat gagttaagga attcgaatat taaggcgagt    2220
gacaaggaac gcccaggatg tggcccagga tggagtaggg gggacactca tttaggagaa    2280
agctcaggcc acaagacagg aggagccagc cttgttgggg ttgaagggaa gagcattcca    2340
ggctgaggga actgcaaggc gtttgcatgg gacactatgg gatggcttct gcccttggtg    2400
ggcagcctct ggtctgaggc cattctttgg cctgcctgac tgtctggcaa ccgggaggaa    2460
gccctgccct tcctggagac agaaacaaag gtctaggaaa tatctgcttc ccttttcctt    2520
gaaaaacgct taagggaacg gaggactggg aggtgccgtc tctctctgcc agcctgcccc    2580
ctaccatagc catcccactc ccatctcaga aagtgacccg ccatcctcca aaaggctcgg    2640
accctgatca aggagtcatc ccccttgtcc cagcacctcc agttggccca gcctccaaaa    2700
cggatgtcaa attcagccct ttctccaagg acactgccca gtccaggccc cactatcatt    2760
catctggact agaacagtca cctcctctcc catctcctgg ctgcagctct tgaagcctca    2820
actgggcccc tgtgaacact tgagttaggg caaggtcctt cctctgctca gaaccctcta    2880
tacctcccac ctcgctgggc ataaaagcca aagtcctggc caggcacggt ggctcacatc    2940
tgttatccca gcactttggg aggccaaggg gggcggatca ctagaggtca ggagttagag    3000
accaacatgg tgaaacccca tctctactaa aaatacaaaa attagctagg cgtggtgacg    3060
caccctgta gtaccagcta ctcggtaggc tgaggtggga gaatcgcttg aacctgggag    3120
gcagagtttg cagtgagccg agatcacacc actgtgctcc agcctgggtg acagaacgag    3180
actggggttc agaaacaaac aaacaaaaca acaaagtcct cctcaggtga caggaacttg    3240
cacctatctg ccctgtcatc tccctgcccg ctcctctcct cgaatctctc ctttgctaag    3300
cctgctccag ccacactgtt ctcctggctg ttccttttt ttttttttt tttttttt       3360
tgagtctcac tctcacccag gctggagtgc agtgcctcta tcttggctca ctgcaacctc    3420
cgcctgccgg gttcaagaga ttctcctgca tcagcctccc aagtaggtgg aattacaggt    3480
gtgcaccacc acacccggct aattttgta ttttgcatag atgggggt ctccctatgt       3540
tgcccaggct ggtcttgaac tcctgggctc aagtgatcct cccatctcgg cctcccaaaa    3600
tgctgggatt acaggtggga gccgcgccca ggtggatttt tgtctgactc tgttcattcc    3660
tgtgtcccca gtacctggaa ggacgccaag cacacagtag gcgcttaaaa aacattgagc    3720
```

```
cacatgttga gaaaagaacg gcaccattgt ggctgcaagt gggacttggg ccgcgcgggg    3780
gagctcgcgc acctcgggcc ggggcaagag ctcagtggaa cccgcccgag gaagaacccg    3840
tggcgcagga ttttcccagg ccttctgagg accaggggcg tcccccgtcc caccctgtga    3900
ctttgctcag gccgttccgg ggcgggaatt cagaactcct cagcccccca agaaaaaaat    3960
atccccgtgg aaattccttg ggaatgaccg aggcggggga aatatgcgtc tctggatggc    4020
cagtgactcg cagccccctt ccccgatagg aagggcctgc gcgtccgggg acccttcgct    4080
tcccccttctg ctgcgcgacc tccctggccc ctcggagatc tccatggcga cgccgcgcgc    4140
gccccacaac aggaaagcct taggcggcgc ggcttggtgc tcggagactt aagagtaccc    4200
agcctcgacg tggtggatgt cgagtcttgg ggtcacacgc acaggcggtg gccaagcaaa    4260
cacccgctca tatttagtgc atgagcctgg gttcgagttg ccggagcctc gcgcgtaggg    4320
caggggttcg agcgcccctt ctccctgcct cgcctctgcg cctggggggct gctgcctcag    4380
tttcccagcg acaggcaggg atttcgagcg tccccctccc ctccctcgtc aagatccaag    4440
ctagctgcct cagtttcccc gcggagcctg ggacgccagc ggagggggctc ggcgcgtagg    4500
gatcacgcag cttccttcct ttttctggga gctgtaaaga cgcctccgcg gccaaggccg    4560
aaaggggaag cgaggaggcc gccggggtga gtgccctcgg gtgtagagag aggacgccga    4620
tttccccgga cgtggtgaga ccgcgcttcg tcactccac ggttagcggt cgccgggagg    4680
tgcctggctc tgctctggcc gcttctcgag aaatgcccgt gtcagctagg tgtggacgtg    4740
acctaggggg aggggcatcc ctcagtggag ggagcccggg gaggattcct gggccccac    4800
ccaggcaggg ggctcatcca ctcgattaaa gaggcctgcg taagctggag agggaggact    4860
tgagttcgga ccccctcgca gcctggagtc tcagtttacc gctttgtgaa atggacacaa    4920
taacagtctc cactctccgg ggaagttggc agtatttaaa agtacttaat aaaccgctta    4980
gcgcggtgta gaccgtgatt caagcttagc ctggccggga acgggaggc gtggaggccg    5040
ggagcagccc ccggggtcat cgccctgcca ccgccgcccg attgctttag cttggaaatt    5100
ccggagctga agcggccagc gagggaggat gaccctctcg gcccgggcac cctgtcagtc    5160
cggaaataac tgcagcattt gttccggagg ggaaggcgcg aggtttccgg gaaagcagca    5220
ccgccccttg gccccaggt ggctagcgct ataaaggatc acgcgcccca gtcgacgctg    5280
agctcctctg ctactcagag ttgcaacctc agcctcgcta tggctcccag cagccccgg    5340
cccgcgctgc ccgcactcct ggtcctgctc ggggctctgt tcccaggtga gtcggggtgg    5400
ggattgccgt cgggccagtt ctccgaagcc ccgggaggac cggctcccgg gtcaggtcat    5460
gcatgcttag gtagctgttt atgggaagga ggggctagag acagcgattg aaaggcaaca    5520
gccagtaggt tcgaatccag accctgcata cctccacgtg tggccttggg ctatagattg    5580
cagcttaaaa aaagggtagg gggttggaga tggagggggag gggcgggcct cgttttgttg    5640
cccaggccgg tcttgaactc cggggtctag gccttacctc ctgcctcagc ctcccgagta    5700
gctgggatga gaggtgtgaa ccaccgcctt gcttggctag attgcgtctc ttacagtttc    5760
tcagctgtaa aacgggaaac gttatagcgg ccacctggca gggtatcttg gcccagcgca    5820
gcacctggcc ccaggactcg atcatgatgg tttgggaact tggctctgtg ccaacccaac    5880
aaggcttaag ggaccccac cccctcaag atgtatattc tgttcctcat cctctctgcc    5940
cctggggaag tccagggctg cttctacttg ggggaattcc agagctgact tatccgtggc    6000
ccaaagctga gaagtgggac gccccagcac acctccccc agctccagcc cagctaggga    6060
agagggaagg ggtcagaggg tctttcatgg tggtgtaagt ttggggaacc aggagggtgg    6120
```

```
gagattgaca gcttggttaa cagctcaaca aagcctgaga tccaggccag cacggtagtt    6180
catgccagta atcccaacac tttaggagcc ccaggcgggc gaatcactta aggtcaggag    6240
tttgagacca gcctggccaa catggcaaca tcccgtctct actaaaaata caaaaattag    6300
ctggcatggt ggtgggcgcc tgtgatccca gctgctcggg aggctgaggg aggaaaatcc    6360
cttaagccca cgaggctgag gttgcagtga accaagattg tgccactgca ctccagcctg    6420
ggagacatag cgagattctg tctcaaaaaa caaagcgttc tgatccggac tcagacccag    6480
atcgcactgc tttctagctg agtaaccatt tctctctatg aaatgggaat ggtcccagaa    6540
tctcccttgg agaatgtatg gagccagtgt cctcacaccc ccatccaaga tagaacaaat    6600
ctgagacagg aatctttgag tgaggcagtg ctgggctcag acattttttc ccaccttcgg    6660
aggcagcaga atctgaggga cctgatccaa ataagcccct tctttctttc ttttcttttc    6720
tttttttttt ttttttttttt ttgagacgga gtctcactct gtcgcccagg ctggagtgca    6780
gtggcgtgat ctcggctcac tgcaacctct gcctcccagg ttcaaacgat tctcctgcct    6840
cagcctccct gagtagctgg gactacaggc atgtgccatc acacccggct aatcactgtg    6900
ttagccagga tggtctcgat ttcctgacct catgatctgc ccaccctgcc tcccaaagtg    6960
ctgggattac atgcgtgagc cacagtgccc accccgtaag ccccttcttt cttacctgca    7020
aggtagccag ttgctaccca tcctgtgctg agttacttgt attagcaagg gatggggtgg    7080
ctatactcac ccaccttaca gatggggaaa ttgaggccca agaggggga aactacgtgt    7140 ctcagggagt gaggagccag tctgattcct ggagggctga ctgtctccac ctgacttctt    7200
aggagggagg agggcaccaa cttcacatta aaatctggtt ggacacagtg gctcacacct    7260
gtaatcctgg cattttggga ggcttaggcg ggaggatcac ttgaggccag gagtttgaga    7320
ccagccttag caacatagtg agaccccatc tctacaaaaa tgttttttcag gccaggcgc    7380 ggtggctcac acctataatc ccagcacttt gggaggctga ggcgggcgga ttacctgagg    7440
tcaggagttt gagaccagcc tgaccaacat ggagaaaccc cgtctctact aaaagtacaa    7500
aattacccgg gcgtggtggc gcatgcctgt aatcccagct actcgggagg ctgaggcagg    7560
agaatcgctt gaacctggga ggcggaggtt gcggtgaact gagatcgtgc cattgcactc    7620
cagcctgggc aacaagagct aaactccgtc tcaaaaaaaa aaaatgtttt ttcaaatatt    7680
agccgggtat ggtggtgtcc tgtagtccca gctacttggg aggctgagat gggaggatca    7740
cttgagccca ggagttcaag gttacagtga gctatgattg tgccactgta ttccagcctg    7800
ggtaacagag ggagacccgt ttaaaaaaaa aaaagtgatg gctaaagtcc ttccatggct    7860
ccctattgcc ctcagtataa agaacacatg tggctgggcg tggtggttca cgcctgtaat    7920
cccagcactt tgggaggctg aggcgggcgg atcacttgag gccaggagtt tgagagcagg    7980
ctggccgacg tggcgaaacc ccgtctctat aaaaatacaa aaattagct gggcgtggtg    8040 gtgcttgcct gtaatcccag atactctgga ggctgaggca ggagaatcac ttgaacccgg    8100
gaggcaaagg ttgcagtgag ctgagattgc gccactgcac tccagtctga gtgacaaagc    8160
gagactccat ctcaaaaaaa aaaaaaataa agaacacat ctttagcatg gccttcagtg    8220
ctcacgggat cttcctgaat taatctcccc ctcttcatcc ttgctcactc agctccagcc    8280
accctgcccc gggacatctg tacttgcctg gaacttattt ccctttttctc cggacagcca    8340 gcccttcctc gtcatttaga tctctgctga aacattaccc tgtcaccaaa gcactgtcta    8400
ttctatcacc ctgttttgtt tttgtcaaag ctcatattaa catcagttat taattatctt    8460
gtttgctcat aatttttttt tttttttttt tggagacaga gtctcgttct gttgctcagg    8520
```

```
ctggagtgca gtggcacaat cttggctcac tgtaacctcc acctcccagg ttcaagtgat    8580
tcttgtgcct cagcctccca aatagctagg actacaggca cgtcccacca tgcccagcta    8640 attttttgtat ttttagtgga gacggggctt tgtcatgttg gccaggctga tctcaaattc    8700
ctgacctcaa gtgatctgcc cgccttggcc tcccaaagtg ctgggattac aggcgtgagc    8760
caccacaccc ggcctgctca tgaattttct ctttaacttc cacatcgaag caaagtatt    8820 gtcttgttaa ggctgtgcct ccagcaccca gcacaggctg ggcgcacatt cccttgatga    8880
acctgatttg taatgcctgt cgcctcttcc ctcgtttctt ctaggacctg caatgccca    8940 gacatctgtg tcccctcaa aagtcatcct gccccgggga ggctccgtgc tggtgacatg    9000
cagcacctcc tgtgaccagc ccaagttgtt gggcatagag accccgttgc ctaaaaagga    9060
gttgctcctg cctgggaaca accggaaggt gtatgaactg agcaatgtgc aagaagatag    9120
ccaaccaatg tgctattcaa actgccctga tgggcagtca acagctaaaa ccttcctcac    9180
cgtgtactgt gagtaactga gcccgagggg ctggactagg cagacccggt gggagagacg    9240
tgcaggggca cctgcagagg cctgggggaa tctttgccac ttgctcgtag ggtcaaggag    9300
gggctccttg cagggcaggt ggggacatcc ttggaaagtc cctttgtgaa tttcttttggg   9360 tacaattaaa gtatttacag gctgggtgcg gtggctcatg cctgtaatcc cagcactttg    9420
agaggctgag gctggcggat cacctgagat caggagttta gtttcgcca acatggcgaa    9480 accctgtctc tgctgaaaat acaaaaatca gccgggcatg gtgtcaagcg cctgtaatcc    9540
cagctacttg gaaggctgag gcaggagaac gcttgaacct gagaggcaga gattgcagtg    9600
agccgcgatc gtgccagtgc actccagtct ggataacaga gcaagattcc atctcaagaa    9660
aaaaaaaatg ccatctctct atgcctcact cttttgaacat atgacacggt cctgcttcag    9720
acactttaat aaaagatgca aattaagcca agtgtggtgg cttgtaccta taatcccaac    9780
tactccagag gctgaggcag aaggatggtt tgagcccagg agtttgagac cagcctgggc    9840
aacagagtga ccctgtttt ctttcttttt tttttttttt ttttttgagac ggagtctcac    9900 tctgtcgccc aggctggagt gcagtggtgt gatctcggct cactgcaagc tccgcctccc    9960
gggttcacgc cattctcctg cctcagcctc ccgagtagct gggactacag gcgcctgcca   10020
ccatgcccgg ctcatttttt tgtattttta gtagagacgg ggtttcactg tgttagccag   10080
gatggtctca atctcctgac ctagtggtcc gcccgcctcg gcctcccaaa gtgctgggat   10140
tacaggtgta agccactgtg cccatccaag accctgtttc taccggaaaa aaaaagtaaa   10200
taatttagct gggcatcgtg gtgtgcacct gtaatcccag ctgctcctga ggctgtgatg   10260
ggaggattgc tttaacccag gggttcgaat cctaggagtt cgaatccatc ctaggcaaca   10320
tagcaaaacc ccattttttat ttaaaaaaaa aaaaaagat atgagttaaa actagccctg   10380
ggatggcatt tttcacatat tggtaacaaa caaaagaatt gatggccggg cgcagtggct   10440
cacgcctgta atcccagcac tttgggaggc cgaggcgggc ggatcacaag gtcaggagat   10500
cgagaccatc ctggctaaca tggtgaaacc ccgtctctac taaaactaca aaaaattagc   10560
cgggcatggt ggcaggcgcc tgtggtccca gctactcagg aggctgaggc aggagaatgg   10620
catgaacccg ggaggcagag cttgcagtga gccaagatcg tgccactgca ctccagcctg   10680
ggcgacagag caagactcca tctcaaaaaa aaaaaaaaa aaagaattg ataacagctg    10740 tgctgccaag gctattggaa cgtaggaggt cctaggacag tgctgttggg agcataaata   10800
agcccaaccc tgtggcggga aattgggcat cagttctcaa aatgtcatgg gctgggcacg   10860
gtggctcacg cctgtaatcc cagcactttg ggaggctgag ggaggcggat cacttgaggt   10920
```

```
caggagttcg agaccagcct gaccaccatg gagaaacccc gtctctatta aaaatacaaa   10980
aaaaactagc caggcatagt ggcacatacc tgtaatccca gctactcggg aggctgaggc   11040
aggagaatct cttgaaactg ggaggcagag gttgcggtga gctgagattg cgccactgca   11100
ctccagcttg ggcaacaaga gcaaaactcc atctcaaaaa aaaaaaaaaa agaaataaaa   11160
gaaggtatgt tgaatatgag tggtatgcca ccctcacatt agggaagggc agtttcgggg   11220
aggctgtatt tatgtataaa atagccctaa aaggaagtgg gagaaatgac aatattagct   11280
ggctatgaga agagaggctg ggaggctgtg ggagagggct tgggtgtgga gaattctttt   11340
tgttttttcc ttttttttgag acagagtttc actcttgttg cccaggctgg agtgcaatgg   11400
cacgatctca gctcaccgca accttcacct cctgagttta agtgattctc cggcctcagc   11460
ctcccgacta gctgggatta caggcatggg ccactacgcc tggcaaattt tgtattttta   11520
gtagagacag ggtttctcca tgttggtcag gctggtcttg aactctgacc tcaggtgatc   11580
cgcccgcctc ggcctcccaa agtgctggga ttacaacgtg agccactttg cctggctgag   11640 aattctttt tgttgttgt cttttgaga tggagttttg ctgtgtcccc agcctggagt   11700
gcaatggtgt aatctcagct cactgcaacc tctccctccc gggttcaagc aattctcctg   11760
cctcagcctc ccaagtagct ggaattacag gcgcccagca ccacgcccgg ctaattttg   11820 tattttagt agagacggga tttcatcatg ttggccaggc tggtcttgat ctcctgacct   11880
tgtgatctgc ccgcctcggc ctcccaaagt gctgggatta caggcgtgag ccactgcccc   11940
cagccgagaa tttctctttg cgtccttcct actttgggga cttcgaatgg tgggaaagag   12000
ttatcaaggc caaaataagg aattcaaatg aaaacaaaac aaaatcaaag aagaaaaaac   12060
agaagagcac tgggcaggct aggcacgtgg ctcatgccta taatcccagt gatttagaag   12120
gccgaagtag aaggatcgct tggaggccag gagttggaca ccagcctggg caacatagca   12180
agaccccata tctacaaaaa ataaaaaacc taaccaagcg tgctggcata ctagtagtcc   12240
cagctactca ggaggctgag gtgggaggat cacctgagcc tgggaggtcc aggctgtagt   12300
gagccgtgat gacaccactg cactccagcc tgggtgacag agaaagaccc tgtctctaaa   12360
aaataaaaac tggccaagta gctttgggat tagccttggg ttccagtccc agcaaggcct   12420
ttaatagctt gggacatgac ttctgcattt actttgcaat caggtgagac ctcctctgat   12480
ggggaaaatg acacggtgag tgacaaagga tgttctccta tcattgtgtc agggcaagga   12540
agcctctggg taaatgatca aatgatcagc tttgcttctg atttggaggg tgggtgagca   12600
gatgctgacc ttcccaggtg agggaagtcc ccgaacattc ccagcagctt ctggaaaccc   12660
cagggaaacc tctttgaagg tcttttctgc atctctgcct gataggtctt ttttttttt   12720 tttttttttt tctttttttt gacacacagt cttgctctgt cgcccaggct ggatcactgc   12780
aacctccatc tcccgggttc aagcagttct cctgcctcat cctctccagt agctgggatt   12840
acaggcacct ggcaccacgc ctggctaatt tttgtatttt tagtagagac agggtttcgc   12900
caagttggcc aggctggtct cgaactctag acctctggtg atccaccgc ctcagcctcc   12960 cgaagtgctg ggattacagg cttgagccac cacgcgcggc tctgcctgat agctgagagc   13020
atagaactcc aggtttgaga cctggctctg ccacatttct ccctctatga ctgtgggtgc   13080
cccactttgc cttagttttt acctctgtga aatggagcag atggctggca caggtagcaa   13140
aggagtaaaa gttatgtggg agggtggtac ctgagagaga ctctagcttg gtcttgcccc   13200
acccctggtg taaacataaa gaagcctccc tggatggctc aatcttctcc aaaaaggtta   13260
gaggtgtaat tcctagagga ggcgaccact agctgggctt tgaaggatgt gtaggagttc   13320
```

```
ataaggacag gcattctggg caggaggaac agcctgggca aaagttggga gcagggagaa    13380
atcttgatgg aggcaggagg aggaggaggt aggttggtgt aggccaggtg cagtggctca    13440
cacctgtaat cccagtgctt tgggaggcca aagcaagagg attgtttgag cccaggagtt    13500
cgagaccagc ctgggcaaca tagcgagacc ctgtctctaa gaaaaaataa aaaaattagg    13560
gtacagtggc atatgcttgt attctcaact actctggagg ctcaagtggg aggatcactt    13620
gaacccagga attttttgt ttttgttttt gttttttga gatggagtct cactctgtgg       13680
cccaggctgg agtgcagtgg tgccatcttg gctcactgca gcctcctcca cctcctgggt    13740
tcaaccgatt ctgctgcctg agcctcccga gttgctggga ttaaggtgcc caccatcatg    13800
cccagctaat ttttttgtat ttttagtaga gatagggttt accatgttag ccaggctggt    13860
cttgaacgcc tgaccgcaag agatcctcct gcctcagttt cccaaagtgc tgggattata    13920
ggtgtgagcc actgagcctg gtcaagccca ggaatttgag gttacagtca gctatgattg     13980
caccactgca ttccagccca ggtgacagag agagacactg cccctaaaaa aaaaaaaaaa    14040
attgattgat gggaggaagg gtgaggttgg cagagccttg aatgccaggt ggaggagctg    14100
ggactttcct tcttggggtg atagggagtc atggagggtt tctgagcagg ccagggatta    14160
gatagctgaa ggctggattt actggaagcc aatgagcagt tggctatggt ccttgtccac    14220
gcggcccatg ttgtgggcag tgaccgtatt caagaaggga aggacagaca agtatttgaa    14280
tacttcagtg accaggattt ggtaaaggac tgcaggtcag ggtcaagaag aggtgagagc    14340
aggacagact tcctccccgc tgcaccaggc agctgagctg ggtttcctct aggggctgag    14400
gtttgagggt acctcaagtt ctgcaagagt ctataggagg tggtaagaga aagagctgg     14460 aggtcagagt tttcttgact atatatatat atatttttt gttttgttt ttaacagctt      14520 aacagctttc tgttttattt ttagagacag ggtctcaggg tctcactttg tcacccaggc    14580
tggagtgcag tggtacaatc gtagctgact gcagcctcaa actcccaggc tcaagaaatc    14640
ctcctcccac ccttagcctc ctgagtagca gggactacag gtgtgagcca gcaggaagcc    14700
cagctggttt ttttttttc tttggtgttt tttgtttgtt tgtttgagac cggagtttcg      14760
ctcttattgc ccaggctgaa gtgcaatggc aggatcttag ctcaccacaa cctccgaccc    14820
ccaggatcaa gctattctct tgcctcagcc acctgagtag ctgggattac aggcatgcga    14880
caccacacaa ggctaatttt gtattttag taaagacagg gtttctccat gttggtcagg       14940
ctggtctcga actcccaacc tcagatgatc cacctgcctc ggcctcccaa agtgctgaga    15000
ttacaggcat gagccaccgt gcccggcctt ttttttttt tttttttttt tgagacagag       15060
tctcactctg tcgcccaggc aggagtgcag tggttcgatc tgggctcact gcaagctccg    15120
cctcccgggt tcactccatc ctcctgcctt agcctcctga gtagctggga ctacaggcgc    15180
ccaccaccac gcctggctaa ttttttgtat ttttagtaga cggggttt caccgtgtta       15240 gccaggatgg tcttgatctc ctgacctcgt gatccgcccg ccttggcctc ccaaagtgct    15300
gggattacag gcgtgagcca ccatgtctgg cctggccagg ctggtcttga actcctgact    15360
tccggtgatc catctgttct ggcctcccaa agtgctggga ttacaggcat aagccaccac    15420
gccatgccga agcccagctt gttttaatt ttttttttt ttttggaga aatgaggtct         15480 tgcaatgttg cccaagctag ccttgaactc ctggcctcaa atgacccgc cttggcatcc      15540 caaagtactg ggattacaga tgtgagccac catgccccag ccttgctttc ttgagatacg    15600
atttagaata cctaaagatt catccctttt aagcacataa ttcaatgact tctgtacaaa    15660
caaccatgac tacaatctaa ttttaaaata tttcaatcac tctaaaaaag aaacctcctg    15720
```

```
cttatgtaca gcgactctgt ctacctctta agtgaattct cctacccttta atagccctat   15780 tttacagttc aggaaactga ggttcagaga gacaaagtca cttacccaca gcaaagaagc   15840
aaggctgggt atcaaatgca ggaccccccc ggtcctgatg ctttttttt tttttttt     15900 ttcctctgag agagactctc actctgtcac tcagtctaga gtacagtggc gcgatctcag   15960
ttcactgcaa tctctgcctc ctgggctgaa gtaatccttt cctcacaagt aaacctcagc   16020
ctctcaagta gctgggacta caggcacaca acaccacgcc tggctaattt ttgtattttt   16080
aggtagagac ggggtttcac tatattggcc aggctggtct tgaactcctg acctcaggtg   16140
atccgcctgc ctcggccccc caaagtgttg ggattacagg cgtgagccac cacacgcagc   16200 cttttttgtta ttagactctg tcattactga ctttttttt tttttaatag aaacagggtc    16260
tttctttccc aggctaaagt acagtggcat gatcacagtt cactatagcc ttaaactcct   16320
gggctcaagt gatcctcctg cctcagcctc caagtagca gggactacag gtgtgcacca   16380
ccacacccag ttaaccattc attcattcat tcattcattt attttgagat ggagtctcgc   16440
tctgtcacct aggctggagt gcagtggcac gatctcagct cactgcaacc tccacctccc   16500
aggttcaaga gattctcctg cctcagcctc ccgagtagct gagactacag gcgtgcacca   16560
ccatgccaga ctaattttg tattttaat agagacgggg tttcactctg ttggtcaggc     16620
ttatctcgaa ctcctgactt cgtggatcca ccctccttgg cctcccaaag tgctgggatt   16680
aaaggcgtga gccaccgcgc cctgccaacc ttttttttaat ttttcttaga gatgggggtc   16740
tccctatgtt gcccaggctt gtcttgaact cctggcctca agtgaccctc ttgccttggc   16800
ctcacaaagt gctaggatta cagcctgagc catcacacct ggccaacagg tttttttttt   16860
tgttttgttt tgtttttaa agaatgtcta ggccaggctc atttactttc acctgtaatc    16920
ccagcacttt gggaggccgg ggtgggcaga tcacttgagg tcaggaattc gagaccagcc   16980
tgggcaacat gctgaaaccc cgtttctact aaaaatacaa aaattagctg ggtgtggtga   17040
cacgtgcctg taatcccagc tactcaggag gttgaggcag gagaattgct tgaacccagg   17100
aggcagaggt tgcagtgagc caagatcatg ccatcaccct ccagcctggg cgacagaagg   17160
agactcagtc taaaaactta attaattaat taattaaaaa taaaaataca aaaattaacc    17220
tggtgtggtg gtgtgtgcct gtaatctaag ctactcagga ggctgaggca ggagaatccc   17280
ctgaatccca gaggcagagg ttgcagtgag ccaagatcga gccactgttt gcccagtcta   17340
gtgcactggg ctgctgaatt tatttgacca gacacctagc aatagacttt gaagttcttt   17400 tccactttc actctaagat gctgctgtca tgaataagga atattttgat ccccttcaca    17460
aacactcggg gccctcttac cagttttcac tgaagatctt gacattccta tctgcttagg   17520
tgtctgggcg tgtttggggg agatactgaa gaggtagggc tcccaggcag gtgcagttcg   17580
tctgttaggc aggcagcaag gtccacttca ccagacaccc ccacctctgt tttcctgcag   17640
ggactccaga acgggtggaa ctggcaccccc tccctcttg gcagccagtg ggcaagaacc    17700 ttacccctacg ctgccaggtg gagggtgggg caccccgggc caacctcacc gtggtgctgc   17760
tccgtgggga gaaggagctg aaacgggagc cagctgtggg ggagcccgct gaggtcacga   17820
ccacggtgct ggtgaggaga gatcaccatg gagccaattt ctcgtgccgc actgaactgg   17880
acctgcggcc ccaagggctg gagctgtttg agaacacctc ggccccctac cagctccaga   17940
cctttggtga ggattgaaga agccagcagg gagaaggtgg gggtggggta tcctgcaatg   18000
cggtgcctgt ggccacagga tcttttgaga tgggtgtggc cccggctaag gggtgcatgt   18060
gttctaggcg tatgtgacct aggctgctga gtggccctgg aagaggatct cgcaggaggg   18120
```

```
ggaatgaaat gccccagaga agggcttcgg gacgtccatc cctgtctgct cacacctttc   18180
ttctctccct agtcctgcca gcgactcccc cacaacttgt cagccccgg gtcctagagg    18240 tggacacgca ggggaccgtg gtctgttccc tggacgggct gttcccagtc tcggaggccc   18300
aggtccacct ggcactgggg gaccagaggt tgaaccccac agtcacctat ggcaacgact   18360
ccttctcggc caaggcctca gtcagtgtga ccgcagagga cgagggcacc cagcggctga   18420
cgtgtgcagt aatactgggg aaccagagcc aggagacact gcagacagtg accatctaca   18480
gtaagaaggg gcaggggcgg agtgggggctt cttgggggtg tgacctgaac ccggggcggg   18540
gctcactgtg tgcctattcc aggctttccg gcgcccaacg tgattctgac gaagccagag   18600
gtctcagaag ggaccgaggt gacagtgaag tgtgaggccc accctagagc caaggtgacg   18660
ctgaatgggg ttccagccca gccactgggc ccgagggccc agctcctgct gaaggccacc   18720
ccagaggaca acgggcgcag cttctcctgc tctgcaaccc tggaggtggc cggccagctt   18780
atacacaaga accagacccg ggagcttcgt gtcctgtgtg agtggggctg ctggtcaatg   18840
gcccctatcc cccaaggccc aatctccctg aaggtcccat aaggtcttgc ctccaagtcc   18900
tgcccccacc cacctccatg tcatctcatc gtgttttcc agatggcccc cgactggacg    18960
agagggattg tccgggaaac tggacgtggc cagaaaattc ccagcagact ccaatgtgcc   19020
aggcttgggg gaaccattg cccgagctca agtgtctaaa ggatggcact ttcccactgc    19080
ccatcgggga atcagtgact gtcactcgag atcttgaggg cacctacctc tgtcgggcca   19140
ggagcactca aggggaggtc acccgcaagg tgaccgtgaa tgtgctctgt gagtgagccg   19200
gcgggcagag ctgggtgggg gcaggggcca tggacctaat gcaatcctca ccgcctgttg   19260
tatcctcccc acagcccccc ggtatgagat tgtcatcatc actgtggtag cagccgcagt   19320
cataatgggc actgcaggcc tcagcacgta cctctataac cgccagcgga agatcaagaa   19380
atacagacta caacaggccc aaaaagggac cccatgaaa ccgaacacac aagccacgcc    19440
tccctgaacc tatcccggga cagggcctct tcctcggcct tccatattg gtggcagtgg    19500 tgccacactg aacagagtgg aagacatatg ccatgcagct acacctaccg gccctgggac   19560
gccggaggac agggcattgt cctcagtcag atacaacagc atttgggggcc atggtacctg   19620 cacacctaaa acactaggcc acgcatctga tctgtagtca catgactaag ccaagaggaa   19680
ggagcaagac tcaagacatg attgatggat gttaaagtct agcctgatga gagggaagt    19740 ggtgggggag acatagcccc accatgagga catacaactg gaaatactg aaacttgctg    19800 cctattgggt atgctgaggc cccacagact tacagaagaa gtggccctcc atagacatgt   19860
gtagcatcaa aacacaaagg cccacacttc ctgacggatg ccagcttggg cactgctgtc   19920
tactgacccc aaccccttgat gatatgtatt tattcatttg ttatttttacc agctatttat   19980 tgagtgtctt ttatgtaggc taaatgaaca taggtctctg gcctcacgga gctcccagtc   20040
ctaatcacat tcaaggtcac caggtacagt tgtacaggtt gtacactgca ggagagtgcc   20100
tggcaaaaag atcaaatggg gctgggactt ctcattggcc aacctgcctt tccccagaag   20160
gagtgatttt tctatcggca caaaagcact atatggactg gtaatggtta caggttcaga   20220
gattacccag tgaggcctta ttcctcccctt ccccccaaaa ctgacacctt tgttagccac   20280
ctccccaccc acatacattt ctgccagtgt tcacaatgac actcagcggt catgtctgga   20340
catgagtgcc cagggaatat gcccaagcta tgccttgtcc tcttgtcctg tttgcatttc   20400
actgggagct tgcactatgc agctccagtt tcctgcagtg atcagggtcc tgcaagcagt   20460
ggggaagggg gccaaggtat tggaggactc cctcccagct ttggaagcct catccgcgtg   20520
```

```
tgtgtgtgtg tgtatgtgta gacaagctct cgctctgtca cccaggctgg agtgcagtgg   20580
tgcaatcatg gttcactgca gtcttgacct tttgggctca agtgatcctc ccacctcagc   20640
ctcctgagta gctgggacca taggctcaca acaccacacc tggcaaattt gattttttt    20700 ttttttccag agacggggtc tcgcaacatt gcccagactt cctttgtgtt agttaataaa   20760
gctttctcaa ctgcctcagc cttgtgtgag ttgaggggag gtgtcacatc cagctggagt   20820
cctttctaag cagccacagc ctgatcctcc cacttcctcc cccaagaaaa cattgtgggt   20880
tgatggccat accctgaggt tctggtccaa atcggactt ctatgacctt ctgggtctct    20940
agtgaaaact aaagactcct ctccagaaaa aaacatttgg tttctaatga ggcctggaat   21000
cttattcttg acctggggag cggaatccct ttttgcagta ctcccgggcc ctctgttggg   21060 gcctccctt cctctccagg gtggagtcga ggaggcgggg ctgcgggcct ccttatctct    21120
agagccggcc ctggctctct ggcgcggggc cccttagtcc gggctttttg ccatggggtc   21180
tctgttccct ctgtcgctgc tgtttttttt ggcggccgcc tacccgggag ttgggagcgc   21240
gctgggacgc cggactaagc gggcgcaaag ccccaagggt agccctctcg cgccctccgg   21300
gacctcagtg cccttctggg tgcgcatgag cccgagttc gtggctgtgc agccggggaa    21360
gtcagtgcag ctcaattgca gcaacagctg tccccagccg cagaattcca gcctccgcac   21420
cccgctgcga caaggcaaga cgctcagagg gccgggttgg gtgtcttacc agctgctcga   21480
cgtgagggcc tggagctccc tcgcgcactg cctcgtgacc tgcgcaggaa aaacacgctg   21540
ggccacctcc aggatcaccg cctacagtga gggacagggg ctcggtcccg gctgggtga    21600 ggggagggg ctggaagagg tgggggaagg gtagttgaca gtcgctctat agggagcgcc    21660
cgcggacctc actcagaggc tcccccttgc cttagaaccg ccccacagcg tgattttgga   21720
gcctccggtc ttaaagggca ggaaatacac tttgcgctgc cacgtgacgc aggtgttccc   21780
ggtgggctac ttggtggtga ccctgaggca tggaagccgg gtcatctatt ccgaaagcct   21840
ggagcgcttc accggcctgg atctggccaa cgtgaccttg acctacgagt ttgctgctgg   21900
accccgcgac ttctggcagc ccgtgatctg ccacgcgcgc ctcaatctcg acggcctggt   21960
ggtccgcaac agctcggcac ccattacact gatgctcggt gaggcacccc tgtaaccctg   22020
gggactagga ggaaggggc agagagagtt atgaccccga gagggcgcac agaccaagcg    22080
tgagctccac gcgggtcgac agacctccct gtgttccgtt cctaattctc gccttctgct   22140
cccagcttgg agccccgcgc ccacagcttt ggcctccggt tccatcgctg cccttgtagg   22200
gatcctcctc actgtgggcg ctgcgtacct atgcaagtgc ctagctatga agtcccaggc   22260 gtaaagggg atgttctatg ccggctgagc gagaaaaaga ggaatatgaa acaatctggg    22320
gaaatggcca tacatggtgg ctgacgcctg taatcccagc actttgggag gccgaggcag   22380
gagaatcgct tgagcccagg agttcgagac cagcctggac aacatagtga ccccgtct     22440 atgcaaaaaa tacacaaatt agcctggtgt ggtggcccgc acctgtggtc ccagctaccc   22500
gggaggctga gttgggagga tcctttgagc cctgaaagtc gaggttgcag tgagccttga   22560
tcgtgccact gcactccagc ctgggggaca gagcacgacc ctgtctccaa aaataaaata   22620 aaataaaaa taaatattgg cggggggaacc ctctggaatc aataaaggct tccttaacca   22680
gcctctgtcc tgtgacctaa gggtccgcat tactgccctt cttcggagga actggtttgt   22740
ttttgttgtt gttgttgttt ttgcgatcac tttct                              22775
```

<210> SEQ ID NO 16
<211> LENGTH: 907

```
<212> TYPE: DNA
<213> ORGANISM: Homo sapiens

<400> SEQUENCE: 16
gtaggcggtg cttgaactta gggctgcttg tggctgggca ctcgcgcaga ggccggcccg      60
acgagccatg gttgctggga gcgacgcggg gcgggccctg ggggtcctca gcgtggtctg     120
cctgctgcac tgctttggtt tcatcagctg tttttcccaa caaatatatg gtgttgtgta     180
tgggaatgta actttccatg taccaagcaa tgtgccttta aaagaggtcc tatggaaaaa     240
acaaaaggat aaagttgcag aactggaaaa ttctgaattc agagctttct catcttttaa     300
aaatagggtt tatttagaca ctgtgtcagg tagcctcact atctacaact taacatcatc     360
agatgaagat gagtatgaaa tggaatcgcc aaatattact gataccatga agttctttct     420
ttatgtgctt gagtctcttc catctcccac actaacttgt gcattgacta atggaagcat     480
tgaagtccaa tgcatgatac cagagtatta caacagccat cgaggactta taatgtactc     540
atgggattgt cctatggagc aatgtaaacg taactcaacc agtatatatt ttaagatgga     600
aaatgatctt ccacaaaaaa tacagtgtac tcttagcaat ccattattta atacaacatc     660
atcaatcatt ttgacaacct gtatcccaag cagcggtcat tcaagacaca gatatgcact     720
tatacccata ccattagcag taattacaac atgtattgtg ctgtatatga atggtatgta     780
tgcttcttaa aacaaaatag tttgaaaact tgcattgttt tccaaaggtc agaaaatagt     840
ttaaggatga aaataaagtt tgaaatttta gacattcgaa aaaaaaaaaa aaaaagaaaa     900
aaaaaaa                                                               907

<210> SEQ ID NO 17
<211> LENGTH: 7
<212> TYPE: PRT
<213> ORGANISM: Mus musculus

<400> SEQUENCE: 17

Ser Ile Ile Phe Glu Lys Leu
  1               5
```